United States Patent
Finn et al.

(10) Patent No.: US 10,517,952 B2
(45) Date of Patent: Dec. 31, 2019

(54) NUCLEOPHILE-TRIGGERED DEGRADABLE MATERIALS AND METHODS OF MAKING AND USING THE SAME

(71) Applicant: GEORGIA TECH RESEARCH CORPORATION, Atlanta, GA (US)

(72) Inventors: M. G. Finn, Atlanta, GA (US); Cody James Higginson, Union City, CA (US)

(73) Assignee: Georgia Tech Research Corporation, Atlanta, GA (US)

( * ) Notice: Subject to any disclaimer, the term of this patent is extended or adjusted under 35 U.S.C. 154(b) by 146 days.

(21) Appl. No.: 15/532,911

(22) PCT Filed: Dec. 2, 2015

(86) PCT No.: PCT/US2015/063551
§ 371 (c)(1),
(2) Date: Jun. 2, 2017

(87) PCT Pub. No.: WO2016/090060
PCT Pub. Date: Jun. 9, 2016

(65) Prior Publication Data
US 2017/0360940 A1    Dec. 21, 2017

Related U.S. Application Data

(60) Provisional application No. 62/261,328, filed on Dec. 1, 2015, provisional application No. 62/086,438, filed on Dec. 2, 2014.

(51) Int. Cl.
| | | |
|---|---|---|
| C08G 75/04 | (2016.01) | |
| C08G 73/02 | (2006.01) | |
| A61K 47/34 | (2017.01) | |
| C08G 75/045 | (2016.01) | |
| A61L 27/58 | (2006.01) | |
| A61L 15/62 | (2006.01) | |
| C08J 3/24 | (2006.01) | |
| A61K 9/00 | (2006.01) | |
| A61K 9/06 | (2006.01) | |

(52) U.S. Cl.
CPC .............. *A61K 47/34* (2013.01); *A61L 15/62* (2013.01); *A61L 27/58* (2013.01); *C08G 73/0273* (2013.01); *C08G 75/045* (2013.01); *C08J 3/24* (2013.01); *A61K 9/0019* (2013.01); *A61K 9/0024* (2013.01); *A61K 9/06* (2013.01); *C08G 2210/00* (2013.01); *C08G 2230/00* (2013.01)

(58) Field of Classification Search
None
See application file for complete search history.

(56) References Cited

U.S. PATENT DOCUMENTS

2011/0142886 A1    6/2011   Mirosevich

FOREIGN PATENT DOCUMENTS

EP              448148    *   9/1991

OTHER PUBLICATIONS

International Preliminary Report on Patentability from related PCT Application No. PCT/US2015/063551 dated Jun. 15, 2017 (8 pages).
Aimetti, AA et al. "Poly (ethylene glycol) hydrogels formed by thiol-ene photopolymerization for enzyme-responsive protein delivery." Biomaterials. 2009, vol. 30, No. 30, abstract; p. 6049; figure 1.
Hong, V et al. "Thiol-selective fluorogenic probes for labeling and release." Journal of the American Chemical Society, 2009, vol. 131, No. 29, pp. 9986-9994.
Kislukhin, AA et al. "Degradable conjugates from oxanorbornadiene reagents." Journal of the American Chemical Society. 2012, vol. 134, No. 14, pp. 6491-6497 and S1-327; abstract; pp. 6491-6492, 6495-6496, S20-S21, S26.
Shin, H et al. "Cross-linking and degradation of step-growth hydrogels formed by thiol-ene photoclick chemistry." Biomacromolecules, 2012, vol. 13, No. 7, pp. 2003-2012.
Van Berkel, SS, et al. "Metal-Free Triazole Formation as a Tool for Bioconjugation." ChemBioChem, 2007, vol. 8, No. 13, pp. 1504-1508.
International Search Report issued by the International Searching Authority dated Feb. 12, 2016.
Written Opinion issued by the International Searching Authority dated Feb. 12, 2016.

* cited by examiner

*Primary Examiner* — David J Buttner
(74) *Attorney, Agent, or Firm* — Troutman Sanders LLP; Ryan A. Schneider

(57) ABSTRACT

Disclosed herein are degradable materials comprising the reaction product of an oxanorbornadiene crosslinker or derivative thereof and a multivalent nucleophile-terminated compound, wherein the reaction product is a degradable elastic solid capable of entraining cargo. Also disclosed herein are degradable materials comprising a polymeric and hyperbranched crosslinked material made with oxanorbornadiene linkage that can be activated for cleavage at a predetermined rate by addition of a nucleophile. Also disclosed herein are methods of making and using the same.

16 Claims, 46 Drawing Sheets

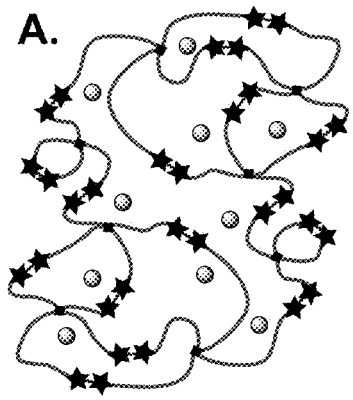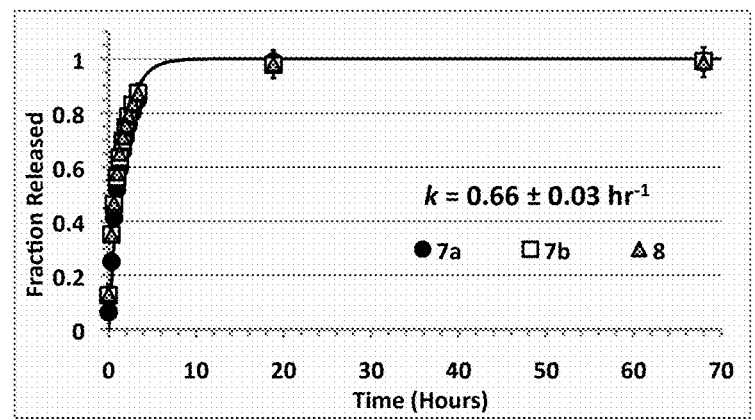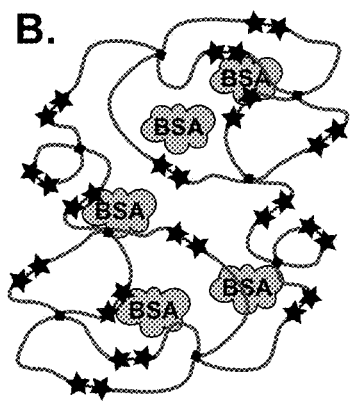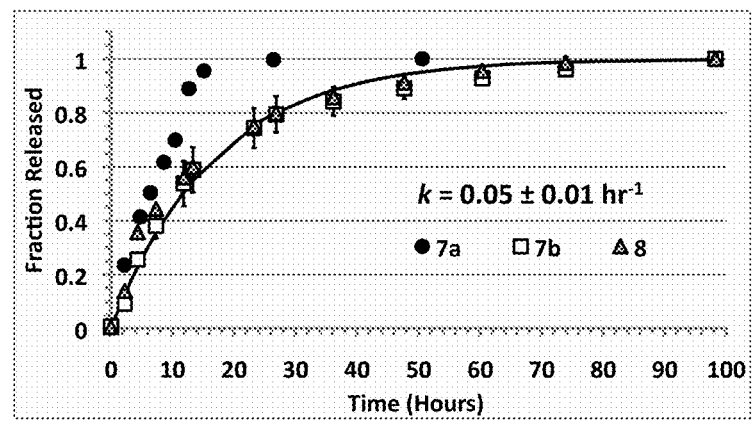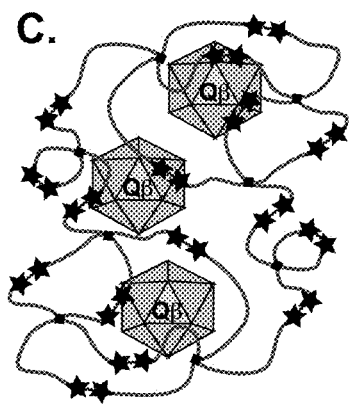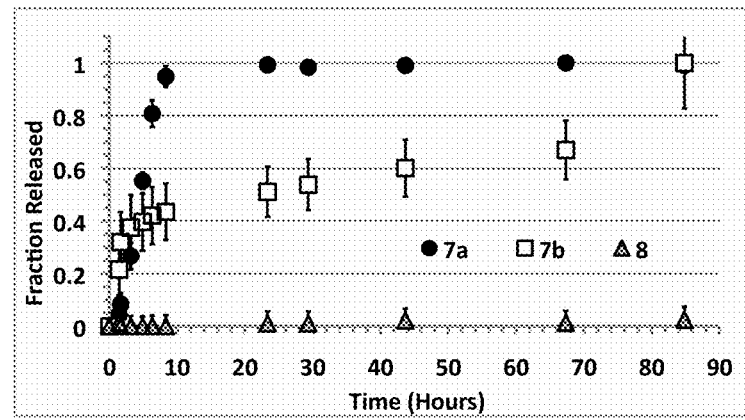
FIG. 3A–3C (a) 1 equiv furfurylamine, 1.4 eq DCC, $CH_2Cl_2$, 6 h; (b) 1.3 equiv ethyl 4,4,4-trifluoro-2-butynoate, toluene, 60°C, 40 h.

NUCLEOPHILE-TRIGGERED DEGRADABLE MATERIALS AND METHODS OF MAKING AND USING THE SAME

CROSS REFERENCE TO RELATED APPLICATIONS

This application is a U.S. National Stage Application of, and claims benefit of priority pursuant to 35 U.S.C. § 371 of International Patent Application No. PCT/US2015/063551 filed on 2 Dec. 2015, which claims priority to, U.S. Provisional Patent Application No. 62/086,438, filed 2 Dec. 2014, and U.S. Provisional Patent Application No. 62/261,328 filed 1 Dec. 2015, each of which is incorporated by reference herein in its entirety.

STATEMENT REGARDING FEDERALLY SPONSORED RESEARCH

This invention was made with government support under grant numbers 1342648 and 1011796 awarded by the National Science Foundation. The government has certain rights to this invention.

BACKGROUND

Degradable materials are can be used in a variety of applications, including but not limited to medical applications. Improved degradable materials and methods of making the same are desired.

SUMMARY

Disclosed herein are degradable materials, for instance, polymeric and hyperbranched crosslinked materials that can be made with oxanorbornadiene (OND) linkages. Each OND linkage can be activated for cleavage at a predetermined rate by the addition of a nucleophile (e.g., a thiol or amine) to the OND structure. While a variety of other degradable materials are known, none use OND connections, and all have different properties. The degradable materials disclosed herein can comprise fragmentation technology that can be triggered by a molecular binding event, followed by decomposition at predetermined rates.

Disclosed herein are, for instance, degradable materials comprising the reaction product of an oxanorbornadiene crosslinker or derivative thereof and a multivalent nucleophile-terminated compound, wherein the reaction product is a degradable elastic solid capable of entraining cargo. In some embodiments, the oxanorbornadiene crosslinker or derivative thereof is multivalent, and the multivalent nucleophile-terminated compound is a multivalent nucleophile-terminated monomer. In some embodiments, the multivalent nucleophile-terminated compound is a multivalent nucleophile-terminated macromer.

In some embodiments, the reaction between the multivalent nucleophile-terminated compound and oxanorbornadiene crosslinker or derivative thereof trigger programmed fragmentation of adducts that causes the material to degrade. In some embodiments, the oxanorbornadiene crosslinker comprises at least one of the following:

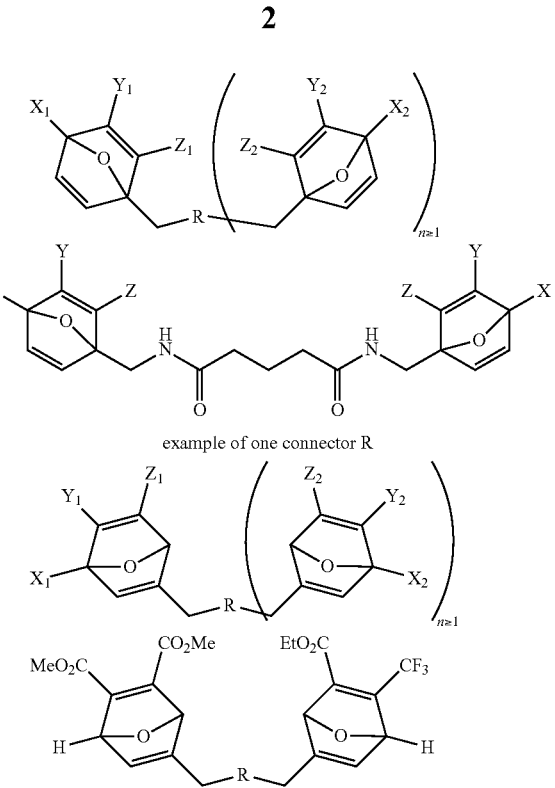

example of one connector R $X_{1,2}$ = e.g. H, Me, Ph
$Y_{1,2}$ = e.g. alkyl ester, $CF_3$, CN, Cl
$Z_{1,2}$ = e.g. alkyl ester, $CF_3$, CN, Cl R = alkyl, diamide, diester, linear and branched polymers and biopolymers. Other examples include core connectors derived from citric acid and pentraerythritol.

Note: $X_1$ and $X_2$, $Y_1$ and $Y_2$, and $Z_1$ and $Z_2$, respectively, need not be equivalent, as shown in the structure above.

In some embodiments, the degradable material further comprises a divalent chain propagator. In some embodiments, the divalent chain propagator comprises at least one of the following:

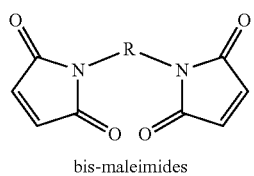

bis-maleimides

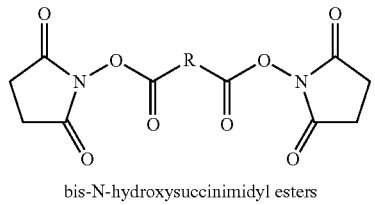

bis-N-hydroxysuccinimidyl esters

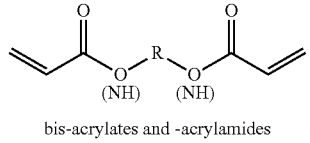

bis-acrylates and -acrylamides

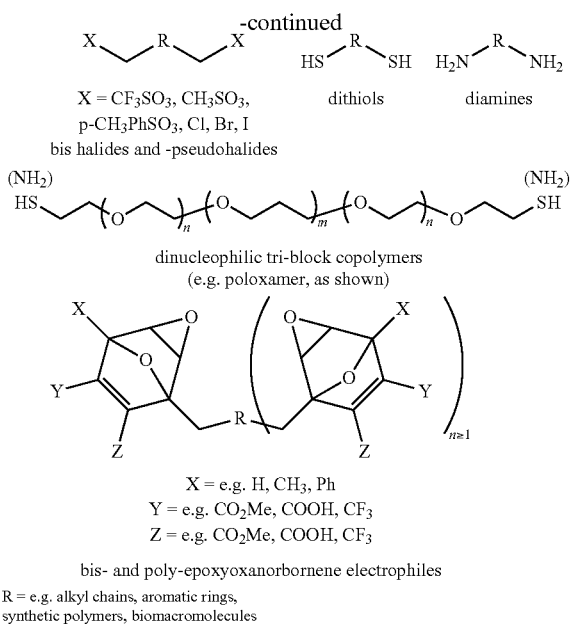

X = CF₃SO₃, CH₃SO₃, p-CH₃PhSO₃, Cl, Br, I
bis halides and -pseudohalides dithiols diamines dinucleophilic tri-block copolymers (e.g. poloxamer, as shown)

X = e.g. H, CH₃, Ph
Y = e.g. CO₂Me, COOH, CF₃
Z = e.g. CO₂Me, COOH, CF₃ bis- and poly-epoxyoxanorbornene electrophiles
R = e.g. alkyl chains, aromatic rings, synthetic polymers, biomacromolecules In some embodiments, the nucleophile comprises a thiol, phosphine, or amine. In some embodiments, the multivalent nucleophile-terminated compound comprises a thiol-terminated multivalent polyethylene glycol. In some embodiments, the multivalent nucleophile-terminated compound has a valency of 4, 5, 6, or 8.

In some embodiments, the multivalent nucleophile-terminated compound is also comprises endgroups pre-labeled and/or post-labeled with a probe or cargo. In some embodiments, the degradable material further comprises a second compound comprising end groups pre-labeled and/or post-labeled with a probe or cargo. In some embodiments, the compound is pre-labeled and/or post-labeled with a probe or cargo to achieve added functionality (e.g., recruiting a cell, releasing a molecule, tuning a material property (e.g., hydrophobicity, hydrophilicity, charge state, polarity or a combination thereof), or a combination thereof). In some embodiments, the molecule comprises a pharmaceutical agent (e.g., chemotherapeutic agent, anti-inflammatory agent, cytotoxic molecule, antimicrobial agent, immunological adjuvant, antibody, protein, peptide, or combination thereof), antimicrobial, nanoparticle, imaging agent, protein, or a combination thereof. In some embodiments, the protein is covalently tethered or physically entrained. In some embodiments, the probe comprises a fluorescent dye, an imaging agent, a radioactive label, or a combination thereof. In some embodiments, the cargo comprises a small molecule, a protein, a nanoparticle, or a combination thereof.

In some embodiments, the degradable material has a tunable cargo release half-life (e.g., 30 seconds to 1 year, 12 hours to 1 month). In some embodiments, the degradable material further comprises an additive (e.g., a buffer, catalytic base, or combination thereof).

In some embodiments, the multivalent nucleophile-terminated compound is present in a concentration of 2.5 wt % to 80 wt % in a solution that becomes a gel. In some embodiments, the reaction product is post-functionalized with a second oxanorbornadiene crosslinker or derivative thereof. In some embodiments, the degradable material is a hyperbranched crosslinked and polymeric material. In some embodiments, the degradable material is an elastic hydrogel. In some embodiments, the degradable material is an organogel.

Degradable materials comprising a polymeric and hyperbranched crosslinked material made with oxanorbornadiene linkage that can be activated for cleavage at a predetermined rate by addition of a nucleophile are also disclosed herein. Also disclosed herein are uses of the degradable materials disclosed herein in applications such as wound dressing, injectable drug device, implantable drug device, tissue engineering substrate, 3D cell culture, or combination thereof.

Disclosed herein are methods for producing a degradable material, the methods comprising: combining a solution of a multivalent nucleophile-terminated compound and an oxanorbornadiene crosslinker to yield elastic solids capable of entraining cargo, wherein the reaction between the multivalent nucleophile-terminated compound and oxanorbornadiene trigger programmed fragmentation of adducts, and wherein the programmed fragmentation of adducts causes the material to degrade.

In some embodiments, the combining takes place at room temperature. In some embodiments, the combining takes place at physiological temperature. In some embodiments, the combining takes place at a temperature from 20° C. to 40° C.

In some embodiments, the combining takes place and at a pH that leads to gelation in less than a minute. In some embodiments, the combining takes place at a pH from 6 to 8. In some embodiments, the combining takes place at a pH of 7.4.

In some embodiments, the half-life of fragmentation of adducts is programmed by the choice of oxanorbomadiene crosslinker or derivative thereof and choice of valence thereof. In some embodiments, the programmed fragmentation of adducts takes place at a half-life of adduct fragmentation of 30 seconds to 4 months. In some embodiments, the half-life of adduct fragmentation is from 12 hours to 1 month.

In some embodiments, the cargo is entrained. In some embodiments, the cargo comprises a small molecule, a protein, a nanoparticles, or a combination thereof. In some embodiments, the reaction between the multivalent nucleophile-terminated compound and oxanorbornadiene crosslinker or derivative thereof trigger programmed fragmentation of adducts that causes the material to degrade.

Also disclosed herein are methods of using the disclosed degradable materials to make, for instance, an enteric coating, wound dressing, injectable drug device, implantable drug device, tissue engineering substrate, 3D cell culture, or combination thereof.

Other embodiments, features, and aspects of the disclosed technology are described in detail herein and are considered a part of the claimed disclosed technology. Other embodiments, features, and aspects can be understood with reference to the following detailed description, accompanying drawings, and claims.

BRIEF DESCRIPTION OF THE FIGURES

Reference will now be made to the accompanying figures and flow diagrams, which are not necessarily drawn to scale, and wherein:

FIG. 3A depicts the release of entrained carboxyfluorescein cargos from PEG-OND hydrogels. Dotted lines represent fit for diffusion of cargo from PEG-OND gel 8.

FIG. 3B depicts the release of entrained bovine serum albumin cargos from PEG-OND hydrogels. Dotted lines represent fit for diffusion of cargo from PEG-OND gel 8.

FIG. 3C depicts the release of entrained bacteriophage Qb virus-like particle cargos from PEG-OND hydrogels.

FIG. 22 depicts $^1$H NMR spectra of 5a.
FIG. 24 depicts $^1$H NMR spectra of 6a.
FIG. 26 depicts $^1$H NMR spectra of 7a.

DETAILED DESCRIPTION

Figures 1A, 1B, 1C, 1D:
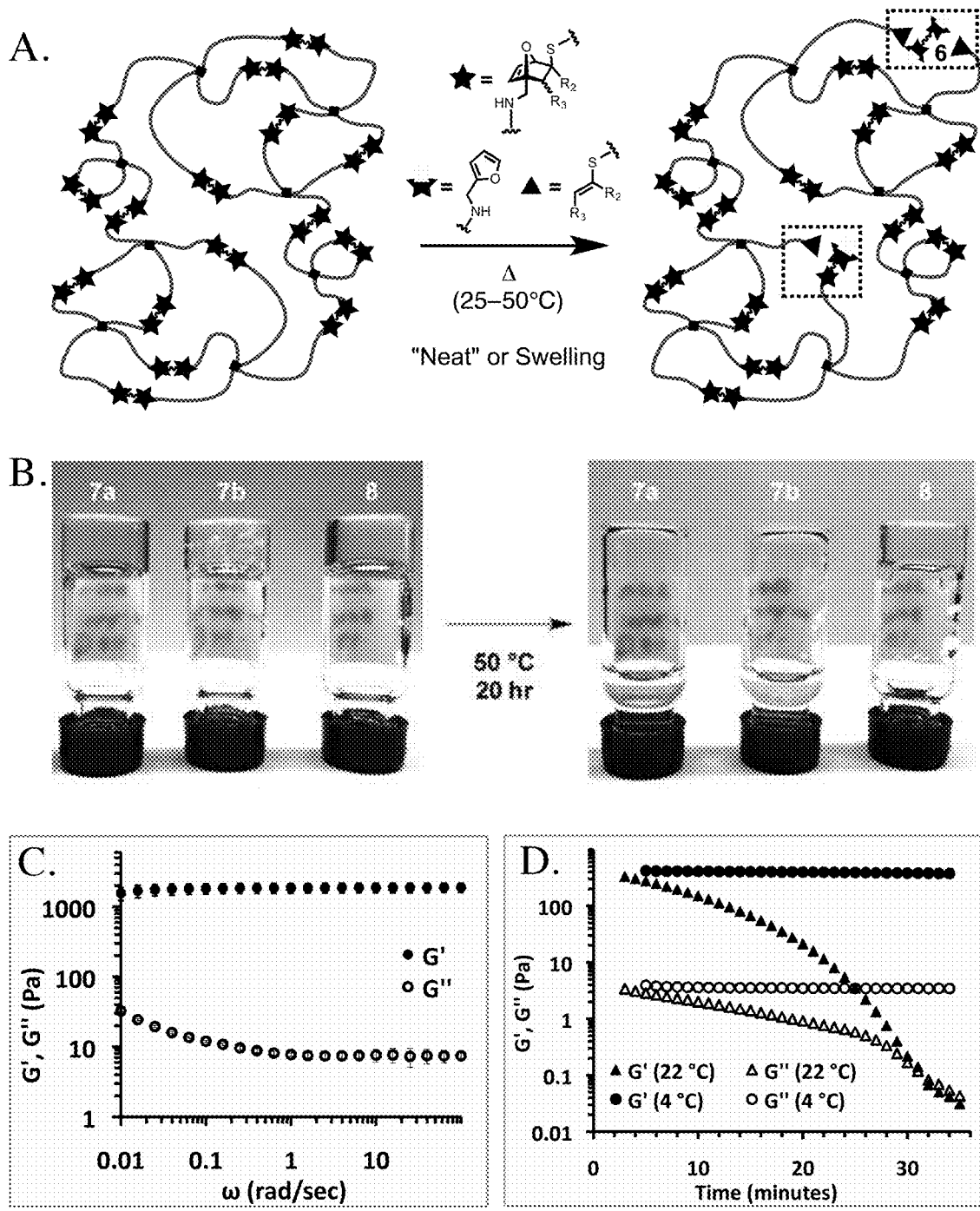
FIG. 1A depicts species formed during degradation of PEG-OND hydrogels.
FIG. 1B depicts an inversion test for hydrogel degradation; gels derived from 8 were stable indefinitely.
FIG. 1C depicts angular frequency dependence of G' and G" at a fixed strain of 1% at 22° C. for gel formed with 8.
FIG. 1D depicts time dependence of G' and G" for gel formed with linker 7c at a constant strain of 5% and an angular frequency of 1 rad/sec, at 4° C. and 22° C.

Disclosed herein are degradable materials, for instance, polymeric and hyperbranched crosslinked materials that can be made with oxanorbornadiene (OND) linkages. Each OND linkage can be activated for cleavage at a predetermined rate by the addition of a nucleophile (e.g., a thiol, phosphine, or amine) to the OND structure. While a variety of other degradable materials are known, none use OND connections, and all have different properties. The degradable materials disclosed herein can comprise fragmentation technology that can be triggered by a molecular binding event, followed by decomposition at predetermined rates.

Disclosed herein are degradable materials, for instance, polymeric and hyperbranched crosslinked materials that can be made with oxanorbornadiene (OND) linkages. Each OND linkage can be activated for cleavage at a predetermined rate by the addition of a nucleophile (e.g., a thiol or amine) to the OND structure. While a variety of other degradable materials are known, none use OND connections, and all have different properties. The degradable materials disclosed herein can comprise fragmentation technology that can be triggered by a molecular binding event, followed by decomposition at predetermined rates.

Disclosed herein are, for instance, degradable materials comprising the reaction product of an oxanorbornadiene crosslinker or derivative thereof and a multivalent nucleophile-terminated compound, wherein the reaction product is a degradable elastic solid capable of entraining cargo. In some embodiments, the oxanorbomadiene crosslinker or derivative thereof is multivalent, and the multivalent nucleophile-terminated compound is a multivalent nucleophile-terminated monomer. In some embodiments, the multivalent nucleophile-terminated compound is a multivalent nucleophile-terminated macromer.

In some embodiments, the reaction between the multivalent nucleophile-terminated compound and oxanorbornadiene crosslinker or derivative thereof trigger programmed fragmentation of adducts that causes the material to degrade. In some embodiments, the oxanorbomadiene crosslinker comprises at least one of the following:

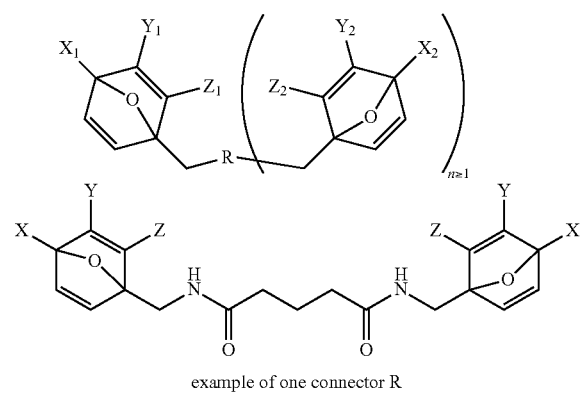

example of one connector R

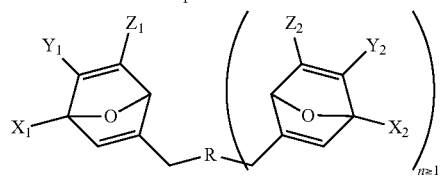

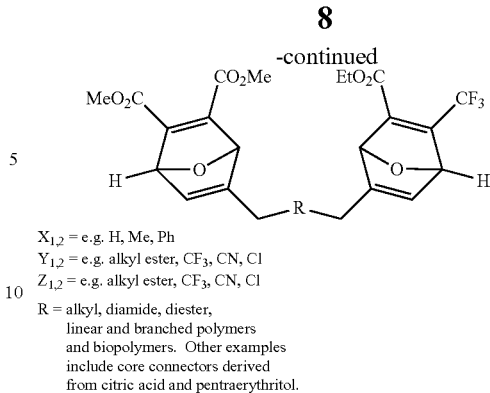

$X_{1,2}$ = e.g. H, Me, Ph
$Y_{1,2}$ = e.g. alkyl ester, $CF_3$, CN, Cl
$Z_{1,2}$ = e.g. alkyl ester, $CF_3$, CN, Cl
R = alkyl, diamide, diester,
   linear and branched polymers
   and biopolymers. Other examples
   include core connectors derived
   from citric acid and pentaerythritol.

Note:
$X_1$ and $X_2$, $Y_1$ and $Y_2$, and $Z_1$ and $Z_2$, respectively, need not be equivalent, as shown in the structure above.

In some embodiments disclosed herein, the degradable materials that can be programmed for a desired level of stability and degradation rate. The fundamental chemistry of oxanorbornadiene (OND) linkages can be found in, for instance, Hong et al., *Thiol-Selective Fluorogenic Probes for Labeling and Release,* 131 J. AM. CHEM. SOC'Y 9986, 9986-94 (2009), and Kislukhin et al., *Degradable Conjugates from Oxanorbornadiene Reagents,* 134 J. AM. CHEM. SOC'Y 64914, 64914-91 (2012), each of which is incorporated by reference herein in its entirety. The oxanorbornadiene crosslinker or derivative thereof can comprise any multivalent substituted 7-oxanorborandiene derivative, as exemplified in the structures above. Polyvalent core molecules can also be derived from other multivalent precursors (e.g., citric acid, pentaerythritol, amine-terminated multivalent polyethyleneglycol). Other possible substitutions of the 7-oxanorbornadiene scaffold are described in Kislunkhin et al., *Degradable Conjugates from Oxanorbornadiene Reagents,* 134 J. Am. Chem. Soc'y 64914, 64914-91 (2012).

In some embodiments, the degradable material further comprises a divalent chain propagator. In some embodiments, the divalent chain propagator comprises a divalent nucleophilic species or divalent electrophilic species. Examples of divalent nucleophilic species include compounds such as substituted dithioalkanes (for example, dithiothreitol), substituted diaminoalkanes (for example, 1,3-diaminopropane), telechelic amine- or thiol-terminated polymers and copolymers (for example, amine- or thiol-terminated linear polyethylene glycols and tri-block polyethylene glycol-polypropylene glycol-polyethylene glycol or poloxamer linkers). Examples of divalent electrophilic species include bis-maleimides, bis-N-hydroxysuccinimidyl esters, bis-acrylate or acyrlamide, bis-haloalkanes, and substituted bis-epoxyoxanorbornenes derived from substituted bis-oxanorbornadiene crosslinkers. Higher valence epoxyoxanorbornenes (i.e. valence >2) may also be employed as chain propagators and non-degradable crosslinkers. Many of these divalent chain propagators are commercially available chemicals. Chemical structures of representative examples of these species are below:

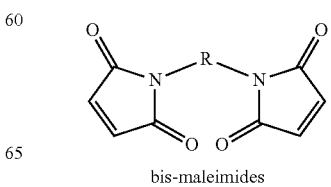

bis-maleimides

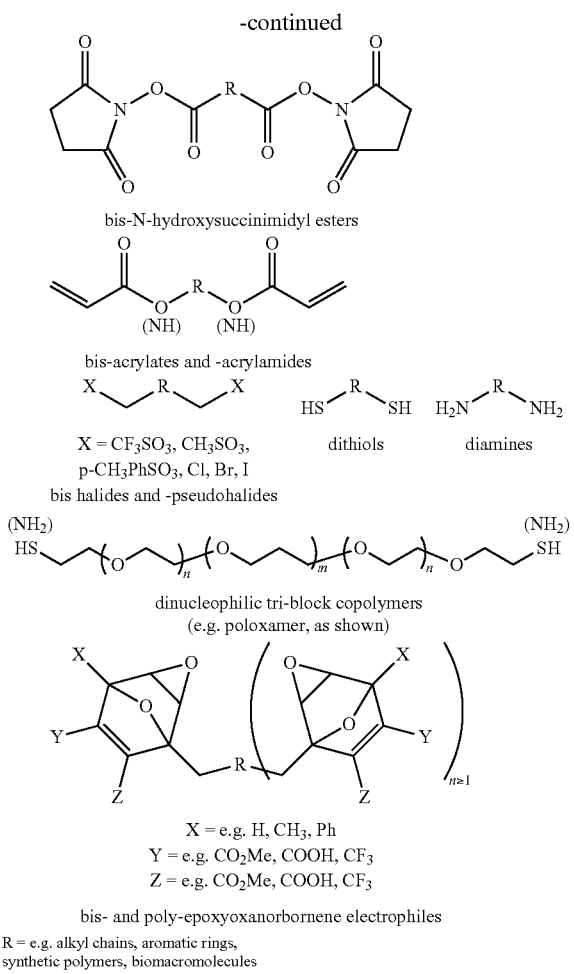

bis-N-hydroxysuccinimidyl esters bis-acrylates and -acrylamides

X = CF$_3$SO$_3$, CH$_3$SO$_3$, p-CH$_3$PhSO$_3$, Cl, Br, I
bis halides and -pseudohalides dithiols   diamines dinucleophilic tri-block copolymers
(e.g. poloxamer, as shown)

X = e.g. H, CH$_3$, Ph
Y = e.g. CO$_2$Me, COOH, CF$_3$
Z = e.g. CO$_2$Me, COOH, CF$_3$ bis- and poly-epoxyoxanorbornene electrophiles
R = e.g. alkyl chains, aromatic rings, synthetic polymers, biomacromolecules In some embodiments, the nucleophile comprises a thiol, phosphine, or amine. In some embodiments, the multivalent nucleophile-terminated compound comprises a thiol-terminated multivalent polyethylene glycol. In some embodiments, the multivalent nucleophile-terminated compound has a valency of 4, 5, 6, or 8.

In some embodiments, the multivalent nucleophile-terminated compound is also comprises endgroups pre-labeled and/or post-labeled with a probe or cargo. In some embodiments, the degradable material further comprises a second compound comprising end groups pre-labeled and/or post-labeled with a probe or cargo. In some embodiments, the compound is pre-labeled and/or post-labeled with a probe or cargo to achieve added functionality (e.g., recruiting a cell, releasing a molecule, tuning a material property (e.g., hydrophobicity, hydrophilicity, charge state, polarity or a combination thereof), or a combination thereof). In some embodiments, the molecule comprises a pharmaceutical agent (e.g., chemotherapeutic agent, anti-inflammatory agent, cytotoxic molecule, antimicrobial agent, immunological adjuvant, antibody, protein, peptide, or combination thereof), antimicrobial, nanoparticle, imaging agent, protein, or a combination thereof. Examples of cytotoxic molecules include doxorubicin or camptothecin. Examples of anti-inflammatory agents include, for instance, salicylic acid or ibuprofen. Examples of antimicrobial compound pharmaceutical agents include erythromycin A. Any pharmaceutical agent or biologic capable of entrainment in the degradable material can be used. In some embodiments, the protein is covalently tethered or physically entrained. In some embodiments, the probe comprises fluorescent dye (such as BODIPY-FL, fluorescein, rhodamine, and cyanine dyes), or other imaging agent (for example, magnetic resonance imaging contrast agents such as gadolinium DOTA and related derivatives), or radioactive label (such as $^{31}$P-labeled DNA or oligonucleotide), or a combination thereof. In some embodiments, the cargo comprises a small molecule, a protein, a nanoparticle, or a combination thereof. In some embodiments, the degradable material further comprises an additive (e.g., a buffer, catalytic base, or combination thereof).

In some embodiments, the multivalent nucleophile-terminated compound is present in a concentration of 2.5 wt % to 80 wt % (e.g., 2.5 wt % to 5 wt %, 5 wt % to 10 wt %, 10 wt % to 20 wt %, 20 wt % to 30 wt %, 30 wt % to 40 wt %, 40 wt % to 50 wt %, 50 wt % to 60 wt %, 60 wt % to 70 wt %, 70 wt % to 80 wt %, 2.5 wt % to 20 wt %, 20 wt % to 40 wt %, 40 wt % to 60 wt %, 60 wt % to 80 wt %, 2.5 wt % to 45 wt %, 45 wt % to 80 wt %) in a solution that becomes a gel. In some embodiments, the reaction product is post-functionalized with a second oxanorbornadiene crosslinker or derivative thereof. In some embodiments, the degradable material is a hyperbranched crosslinked and polymeric material. In some embodiments, the degradable material is an elastic hydrogel. In some embodiments, the degradable material is an organogel.

Degradable materials comprising a polymeric and hyperbranched crosslinked material made with oxanorbornadiene linkage that can be activated for cleavage at a predetermined rate by addition of a nucleophile are also disclosed herein. Also disclosed herein are uses of the degradable materials disclosed herein in applications such as wound dressing, injectable drug device, implantable drug device, tissue engineering substrate, 3D cell culture, or combination thereof.

Disclosed herein are methods for producing a degradable material, the methods comprising: combining a solution of a multivalent nucleophile-terminated compound and an oxanorbornadiene crosslinker to yield elastic solids capable of entraining cargo, wherein the reaction between the multivalent nucleophile-terminated compound and oxanorbornadiene trigger programmed fragmentation of adducts, and wherein the programmed fragmentation of adducts causes the material to degrade.

In some embodiments, the combining takes place at room temperature. In some embodiments, the combining takes place at physiological temperature. In some embodiments, the combining takes place at a temperature from 20° C. to 40° C. (e.g., 20° C. to 22° C., 22° C. to 24° C., 24° C. to 26° C., 26° C. to 28° C., 28° C. to 30° C., 30° C. to 32° C., 32° C. to 34° C., 34° C. to 36° C., 36° C. to 38° C., 38° C. to 40° C.).

In some embodiments, the combining takes place and at a pH that leads to gelation in less than a minute. In some embodiments, the combining takes place at a pH from 6 to 8 (e.g., 6 to 6.5, 6.5 to 7, 7 to 7.5, 7.5 to 8, 6 to 7, 7 to 8, 6.5 to 7.5, 7.2 to 7.6). In some embodiments, the combining takes place at a pH of 7.4.

In some embodiments, the half-life of fragmentation of adducts is programmed by the choice of oxanorbornadiene crosslinker or derivative thereof and choice of valence thereof. In some embodiments, the programmed fragmentation of adducts takes place at a half-life of adduct fragmentation of 30 seconds to 4 months. In some embodiments, the half-life of adduct fragmentation is from 12 hours to 1 month. In some embodiments, the reaction of nucleophiles (e.g., thiol and amine) with ONDs can serve as a mechanism for gelation. In some embodiments, the reaction of nucleophiles (e.g., thiol and amine) with ONDs can trigger for the programmed fragmentation of the adducts by a retro-Diels-Alder mechanism to liberate a thiomaleate or aminomaleate and a furan. This can provide a method of generating degradable hyperbranched materials and elastic hydrogels. In some embodiments, the half-life of adduct fragmentation is tunable, and varies with features present on the parent OND linker. Half-life of adduct fragmentation can vary from minutes to months at physiologically relevant temperatures (e.g., 35° C. to 40° C., 36.5° C. to 37.5° C.) and pH (e.g., 7 to 8, 7.2 to 7.6, 7.4). In some embodiments, the half-life of adduct fragmentation is 30 seconds or greater (e.g., 1 minute or greater, 2 minutes or greater, 3 minutes or greater, 4 minutes or greater, 5 minutes or greater, 10 minutes or greater, 15 minutes or greater, 30 minutes or greater, 45 minutes or greater, 1 hour or greater, 2 hours or greater, 5 hours or greater, 8 hours or greater, 12 hours or greater, 16 hours or greater, 20 hours or greater, 1 day or greater, 3 days or greater, 5 days or greater, 1 week or greater, 2 weeks or greater, 1 month or greater, 2 months or greater, 3 months or greater) at physiological relevant temperatures and pH. In some embodiments, the half-life of adduct fragmentation is 4 months or less (e.g., 2 minutes or less, 3 minutes or less, 4 minutes or less, 5 minutes or less, 10 minutes or less, 15 minutes or less, 30 minutes or less, 45 minutes or less, 1 hour or less, 2 hours or less, 5 hours or less, 8 hours or less, 12 hours or less, 16 hours or less, 20 hours or less, 1 day or less, 3 days or less, 5 days or less, 1 week or less, 2 weeks or less, 1 month or less, 2 months or less, 3 months or less, or 4 months or less) at physiological relevant temperatures and pH. In some embodiments, the half-life of adduct fragmentation is from 30 seconds to 4 months (e.g. 30 seconds to 1 minute, 1 minute to 5 minutes, 5 minutes to 10 minutes, 10 minutes to 15 minutes, 15 minutes to 30 minutes, 30 minutes to 1 hour, 1 hour to 2 hours, 2 hours to 4 hours, 4 hours to 8 hours, 8 hours to 16 hours, 16 hours to 24 hours, 1 day to 2 days, 2 days to 4 days, 4 days to 7 days, 1 week to 2 weeks, 2 weeks to 4 weeks, 1 month to 2 months, 2 months to 4 months, 30 seconds to 8 hours, 8 hours to 1 day, 1 day to 1 week, 1 week to 1 month, 1 month to 4 months, 30 seconds to 1 week, 1 week to 2 months, 2 months to 4 months) at physiological relevant temperatures and pH.

In some embodiments, a unique feature of the OND linkers can be that the fragmentation of thiol adducts can be pH insensitive. This contrasts existing cleavable linker technologies where rate of fragmentation varies greatly with changes in pH. The disclosed embodiments herein show almost invariant degradation rates in a pH range of 1.2-9.0. Accordingly, degradable hyperbranched polymers and hydrogels disclosed herein have a wide range of potential specialty applications in biomedicine and bioengineering. For instance, the disclosed materials and methods can be used in applications in, for instance, wound dressings, injectable/implantable drug eluting depots, 3D cell culture and tissue engineering substrates, degradable sutures, biomaterials, therapeutic drug release, vaccine delivery, and enteric coatings for drug delivery in the stomach and gut. Indeed, the degradable materials and methods disclosed herein can be used for any application in which degradation (e.g., biodegradability) is important.

In some embodiments, the degradable materials comprise cargo. In some embodiments, the cargo is entrained in the degradable material. In some embodiments, the cargo comprises a small molecule, a protein, a nanoparticles, or a combination thereof. In some embodiments, the material can be tuned to have a particular cargo release rate and/or material degradation rates in a pH-independent fashion. In some embodiments, the half-life of cargo release can vary from minutes to months at physiologically relevant temperatures (e.g., 35° C. to 40° C., 36.5° C. to 37.5° C.) and pH (e.g., 7 to 8, 7.2 to 7.6, 7.4). In some embodiments, the half-life of cargo release is 30 seconds or greater (e.g., 1 minute or greater, 2 minutes or greater, 3 minutes or greater, 4 minutes or greater, 5 minutes or greater, 10 minutes or greater, 15 minutes or greater, 30 minutes or greater, 45 minutes or greater, 1 hour or greater, 2 hours or greater, 5 hours or greater, 8 hours or greater, 12 hours or greater, 16 hours or greater, 20 hours or greater, 1 day or greater, 3 days or greater, 5 days or greater, 1 week or greater, 2 weeks or greater, 1 month or greater, 2 months or greater, 3 months or greater, 6 months or greater, 9 months or greater, 11 months or greater) at physiological relevant temperatures and pH. In some embodiments, the half-life of cargo release is 1 year or less (e.g., 2 minutes or less, 3 minutes or less, 4 minutes or less, 5 minutes or less, 10 minutes or less, 15 minutes or less, 30 minutes or less, 45 minutes or less, 1 hour or less, 2 hours or less, 5 hours or less, 8 hours or less, 12 hours or less, 16 hours or less, 20 hours or less, 1 day or less, 3 days or less, 5 days or less, 1 week or less, 2 weeks or less, 1 month or less, 2 months or less, 3 months or less, 4 months or less, 6 months or less, 9 months or less, or 11 months or less) at physiological relevant temperatures and pH. In some embodiments, the half-life of cargo release is from 30 seconds to 1 year (e.g., 1 day to 1 week, 30 seconds to 1 minute, 1 minute to 5 minutes, 5 minutes to 10 minutes, 10 minutes to 15 minutes, 15 minutes to 30 minutes, 30 minutes to 1 hour, 1 hour to 2 hours, 2 hours to 4 hours, 4 hours to 8 hours, 8 hours to 16 hours, 16 hours to 24 hours, 1 day to 2 days, 2 days to 4 days, 4 days to 7 days, 1 week to 2 weeks, 2 weeks to 4 weeks, 1 month to 2 months, 2 months to 4 months, 30 seconds to 8 hours, 8 hours to 1 day, 1 day to 1 week, 1 week to 1 month, 1 month to 4 months, 30 seconds to 1 week, 1 week to 2 months, 2 months to 4 months) at physiological relevant temperatures and pH.

In some embodiments, the time for full cargo release can vary from minutes to months at physiologically relevant temperatures (e.g., 35° C. to 40° C., 36.5° C. to 37.5° C.) and pH (e.g., 7 to 8, 7.2 to 7.6, 7.4). In some embodiments, the full cargo release time is 30 seconds or greater (e.g., 1 minute or greater, 2 minutes or greater, 3 minutes or greater, 4 minutes or greater, 5 minutes or greater, 10 minutes or greater, 15 minutes or greater, 30 minutes or greater, 45 minutes or greater, 1 hour or greater, 2 hours or greater, 5 hours or greater, 8 hours or greater, 12 hours or greater, 16 hours or greater, 20 hours or greater, 1 day or greater, 3 days or greater, 5 days or greater, 1 week or greater, 2 weeks or greater, 1 month or greater, 2 months or greater, 3 months or greater, 6 months or greater, 9 months or greater, 11 months or greater) at physiological relevant temperatures and pH. In some embodiments, the full cargo release time is 1 year or less (e.g., 2 minutes or less, 3 minutes or less, 4 minutes or less, 5 minutes or less, 10 minutes or less, 15 minutes or less, 30 minutes or less, 45 minutes or less, 1 hour or less, 2 hours or less, 5 hours or less, 8 hours or less, 12 hours or less, 16 hours or less, 20 hours or less, 1 day or less, 3 days or less, 5 days or less, 1 week or less, 2 weeks or less, 1 month or less, 2 months or less, 3 months or less, 4 months or less, 6 months or less, 9 months or less, or 11 months or less) at physiological relevant temperatures and pH. In some embodiments, the full cargo release time is from 30 seconds to 1 year (e.g., 1 day to 1 week, 30 seconds to 1 minute, 1 minute to 5 minutes, 5 minutes to 10 minutes, 10 minutes to 15 minutes, 15 minutes to 30 minutes, 30 minutes to 1 hour, 1 hour to 2 hours, 2 hours to 4 hours, 4 hours to 8 hours, 8 hours to 16 hours, 16 hours to 24 hours, 1 day to 2 days, 2 days to 4 days, 4 days to 7 days, 1 week to 2 weeks, 2 weeks to 4 weeks, 1 month to 2 months, 2 months to 4 months, 30 seconds to 8 hours, 8 hours to 1 day, 1 day to 1 week, 1 week to 1 month, 1 month to 4 months, 30 seconds to 1 week, 1 week to 2 months, 2 months to 4 months) at physiological relevant temperatures and pH. When the degradable material finally fully degrades, the entrained cargo remaining in the degradable material can fully release in a final burst.

In some embodiments, the reaction between the multivalent nucleophile-terminated compound and oxanorbornadiene crosslinker or derivative thereof trigger programmed fragmentation of adducts that causes the material to degrade.

Also disclosed herein are methods of using the disclosed degradable materials to make, for instance, an enteric coating, wound dressing, injectable drug device, implantable drug device, tissue engineering substrate, 3D cell culture, or combination thereof.

The degradable materials disclosed herein can be formed by conjugate addition of multivalent amine- or thiol-terminated compound and multivalent oxanorbornadiene crosslinkers or divalent chain propagators. OND linkers present an internal maleate moiety, which can be a potent electrophile with good chemoselectivity toward soft nucleophiles such as thiols. The combination of a solution of thiol-labeled compounds and OND linkers at room temperature (20° C. to 22° C.) and physiological pH (7.4) leads to gelation in less than a minute and can yield elastic solids that are capable of entraining cargos (e.g., small molecules, proteins, nanoparticles, or combinations thereof). In some embodiments, the compound endgroups can be pre-labeled with probes, or other molecular cargos, to achieve added functionality (e.g., recruiting cells or releasing drug molecules).

The OND linkage can be easily prepared from cheap starting materials, and divalent chain propagators can be prepared in sufficient purity for gelation reactions without need for chromatographic purification. This can be desirable for applications that require larger scales where chromatographic purification may be cost-prohibitive.

Without wishing to be bound to theory, the concerted nature of the retro-Diels-Alder fragmentation is likely responsible for the pH-insensitive degradation behavior of the materials disclosed in some embodiments herein. In some embodiments disclosed herein, a range of degradation rates are accessible at physiologically compatible solvent, pH and temperature without greatly affecting material composition (e.g., ratio of macromers to chain propagators or crosslinkers), or physical properties or the network materials.

The degradable materials disclosed herein can be, for instance, hydrogels, elastic hydrogels, degradable hyperbranched materials, or combinations thereof. Hydrogels are water-swollen polymer networks that have found widespread use in a variety of fields, including tissue engineering, three-dimensional cell culture, and the controlled or sustained delivery of biologically active molecules. Polyethylene glycol (PEG) hydrogels, for instance, have received much attention, particularly for biomedical applications, due to their low toxicity and relative lack of immunogenicity. Additionally, PEG hydrogels can be readily permeable to diffusion by both proteins and small molecules. A wide range of linear and branched PEG reagents are commercially available, and facile installation of different functional groups at chain ends enables the exploration of a number of bioorthogonal chemistries to form, for instance, PEG networks, including strain promoted azide-alkyne cycloaddition, Diels-Alder reaction, Michael addition, and thiol-ene reactions. It is desirable to generate degradable hydrogel matrices, with breakdown mediated by various mechanisms including, but not limited to, enzymatic degradation, ester bond hydrolysis, photocleavage, β-elimination, retro-Diels-Alder (rDA), and retro-Michael reactions.

While certain embodiments of the disclosed technology have been described in connection with what is presently considered to be the most practical embodiments, it is to be understood that the disclosed technology is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the disclosed technology, including the best mode, and also to enable any person skilled in the art to practice certain embodiments of the disclosed technology, including making and using any devices or systems and performing any incorporated methods. The patentable scope of certain embodiments of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In addition, supporting time-lapse videos titled "ja5b02708_si_002.mpg" (hereinafter S1 video) and "ja5b02708_si_003.mpeg" (hereinafter S2 video) are incorporated herein by reference in their entirety and are available online under the Supporting Information for the article titled Modular Degradable Hydrogels Based on Thiol-Reactive Oxanorbornadiene Linkers (see http://pubs.acs.org/doi/suppl10.1021/jacs.5b02708 (accessed 1 Dec. 2015)).

EXAMPLES

Summary

A class of 7-oxanorbornadiene dicarboxylate (OND) linkers were examined in which the OND moiety provides for both the connecting (conjugate addition) and cleavage (retro-Diels-Alder, rDA) reactions, building from reports of the chemistry of small-molecule variants (Scheme 1, below). As shown below, the resulting modular OND-based hydrogels exhibited predictable and widely varying stabilities, with little sensitivity of decomposition rate to variations in pH.

Scheme 1. Reaction of ONDs with thiols and fragmentation of adducts.

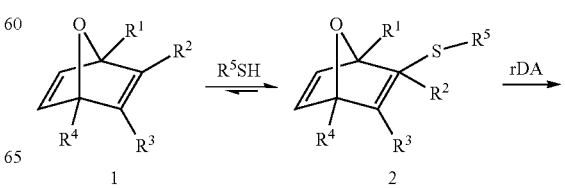

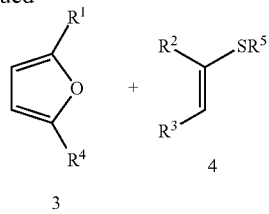

While rDA fragmentation has previously been used to promote degradation in network materials, it has typically required elevated temperatures or high organic solvent content to break them down on practical timescales, and tuning degradation rates yields gels with highly variable physical properties. The more rapid and tunable rDA reactions of OND adducts make them more likely to produce hydrogels with predictable and physiologically-relevant erosion properties.

Figure 41:
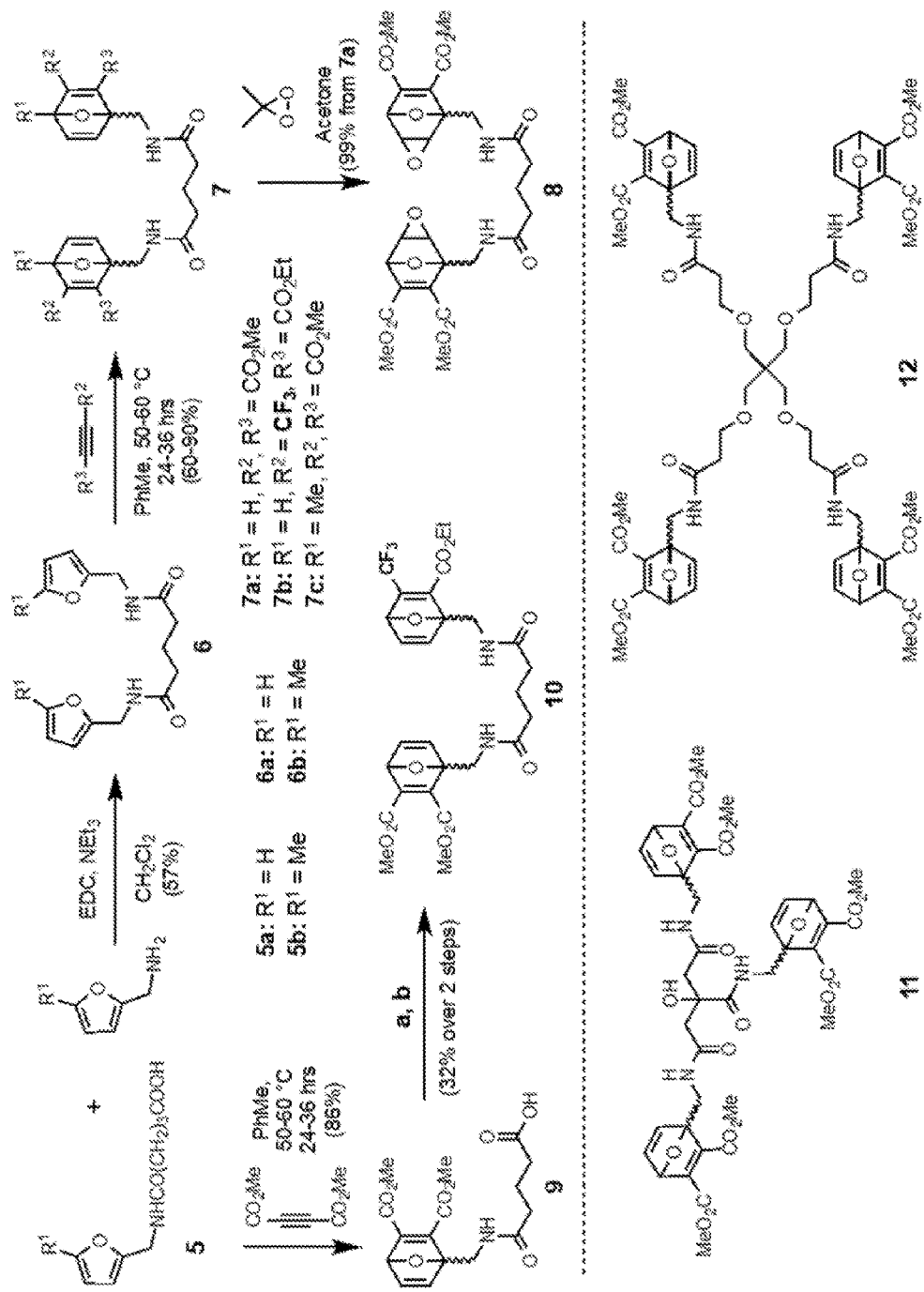
FIG. 41 depicts synthesis of symmetric and asymmetric bis-ONDs, and structures of tris- and tetra-ONDs.

To test this, divalent OND linkers by Diels-Alder reaction were prepared from readily accessible furan derivatives and electron deficient acetylenes, as shown in FIG. 41. Three OND moieties were incorporated into multivalent-OND compounds 7, 10, 11, and 12, designed to yield thiol adducts with varying stabilities to rDA fragmentation. To generate analogous non-degradable gels for comparison, the cleavage-resistant linker 8 was prepared by epoxidation of 7a with dimethyldioxirane (DMDO). While epoxyoxanorbornene linkers exhibit similar rates of Michael addition as ONDs, their adducts are incapable of rDA fragmentation.

Figure 42:
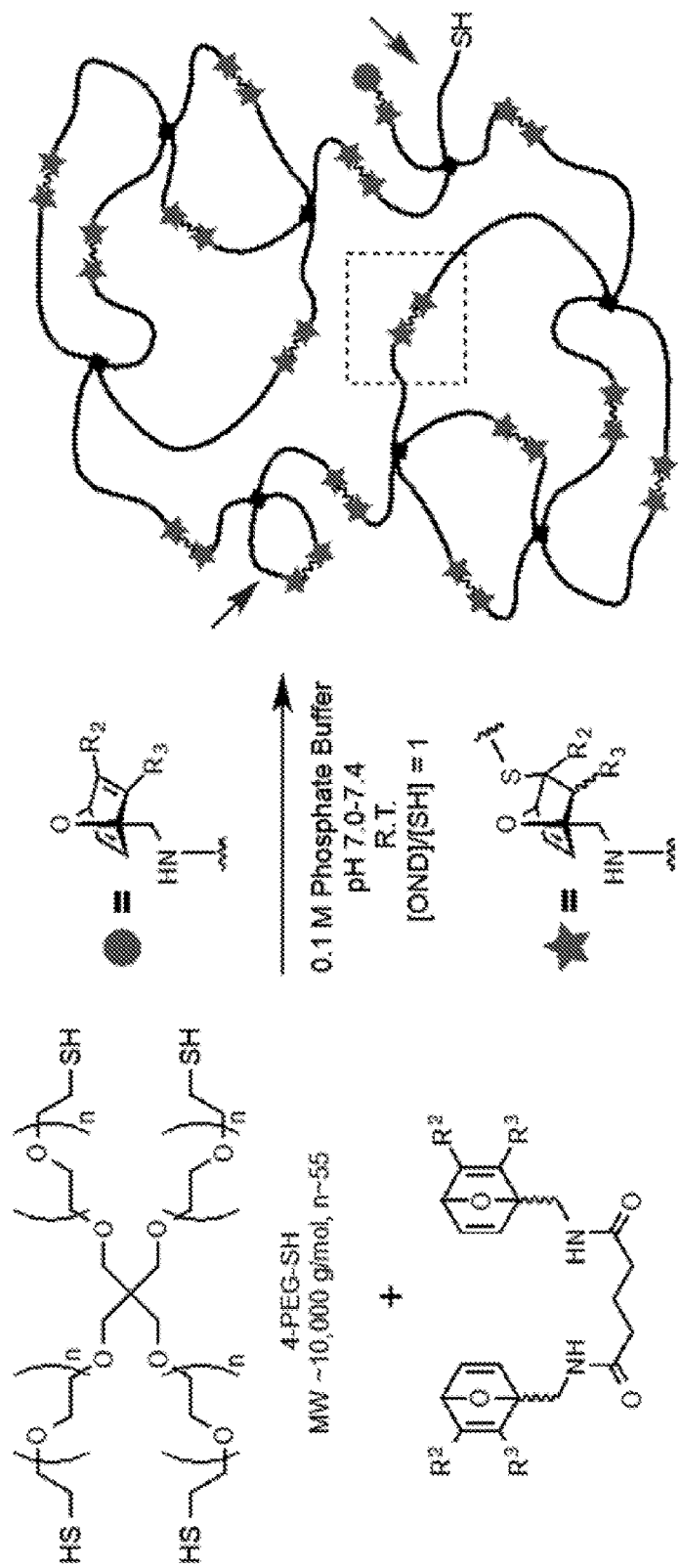
FIG. 42 depicts formation of PEG-OND hydrogels.

PEG-OND hydrogels were prepared by mixing tetravalent thiol-terminated PEG (4-PEG-SH, $M_w$~2,500 Da for each arm) at 3.5 weight percent and multivalent OND linkers at equimolar concentration of thiol and electrophile in phosphate buffer containing 7% DMSO by volume (FIG. 42). The reactions were mixed briefly and the gel was allowed to cure at temperature or 37° C. Gelation time was recorded as the point at which the sample no longer flowed upon inversion of the reaction vessel. For all linkers except 7c, self-supporting gels were observed in less than 90 seconds at pH 7.2 and room temperature, and in approximately 30 seconds at pH 7.4 and 37° C.

In the representation above, the left arrow marks a loop defect, the right arrow indicates an unreacted chain end, and the dotted-line box highlights a productive linkage.

Figure 5:
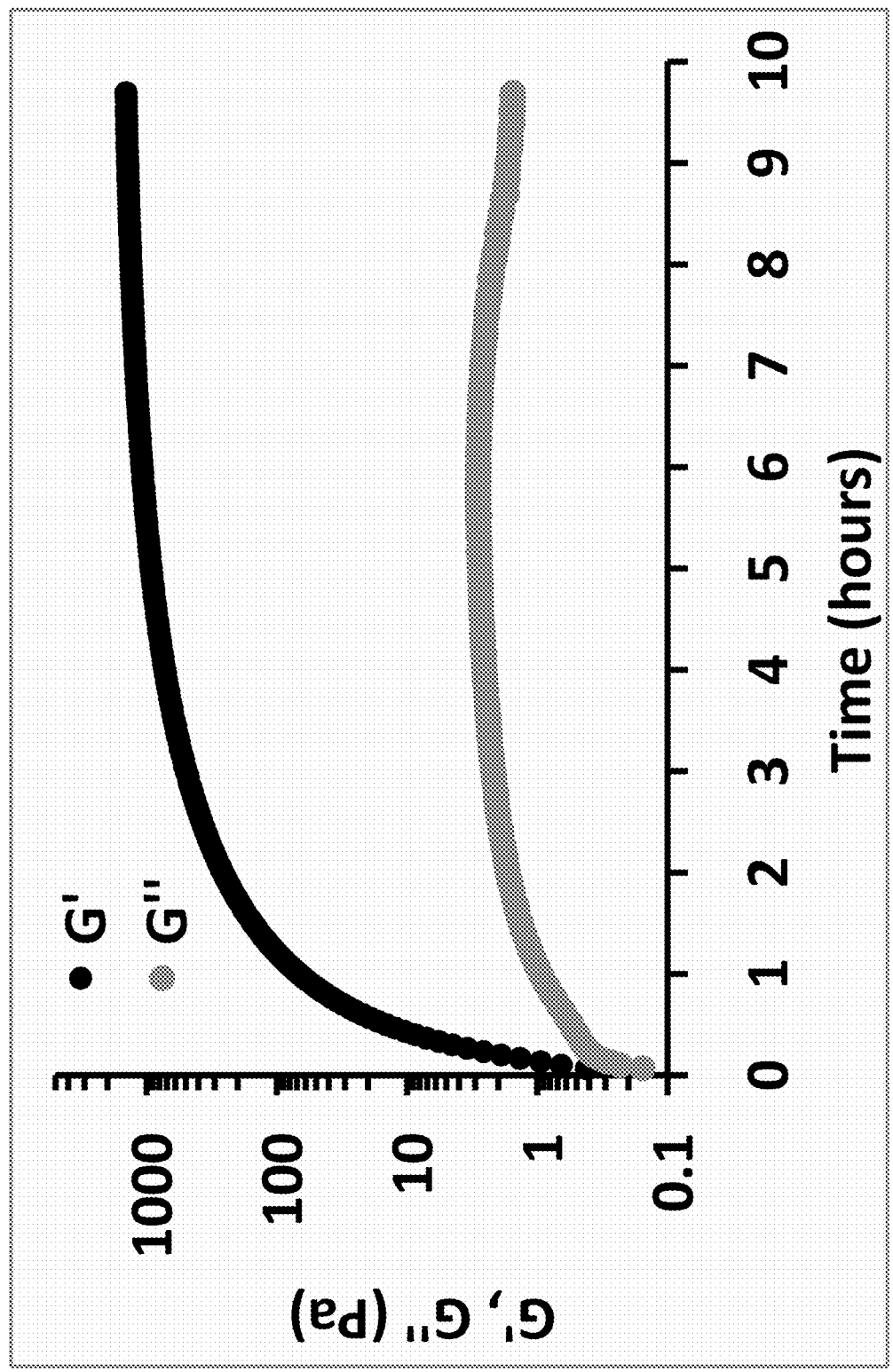
FIG. 5 depicts oscillatory time sweep of the gel derived from bis-EONB 8 and 4-PEG-SH (1:1 ratio of reactive groups) at 37° C.
Figure 6:
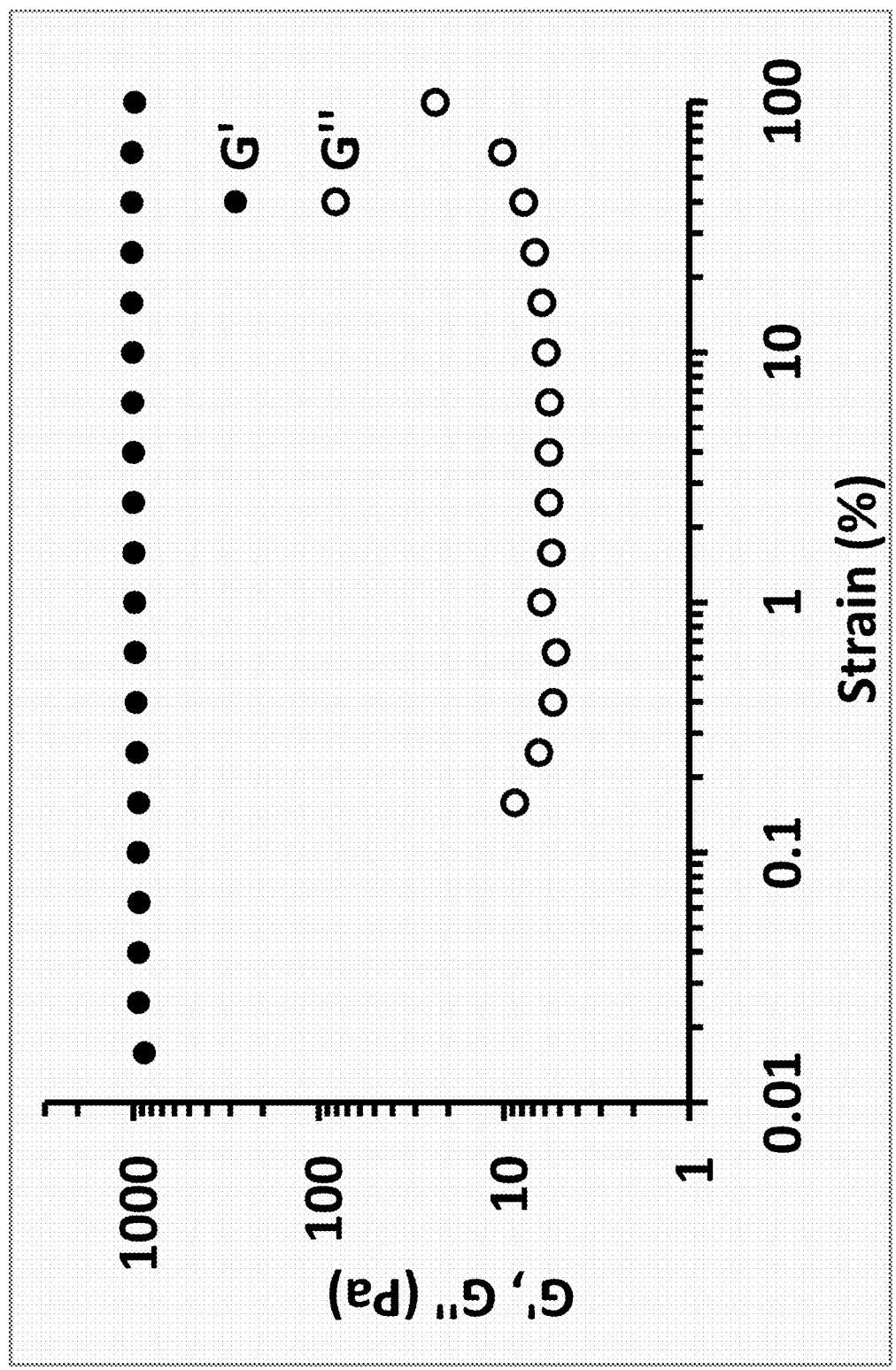
FIG. 6 depicts oscillatory strain sweep of gel derived from bis-EONB 8 and 4-PEG-SH (1:1) at 37° C. and ω=1 rad/s.
Figure 10:
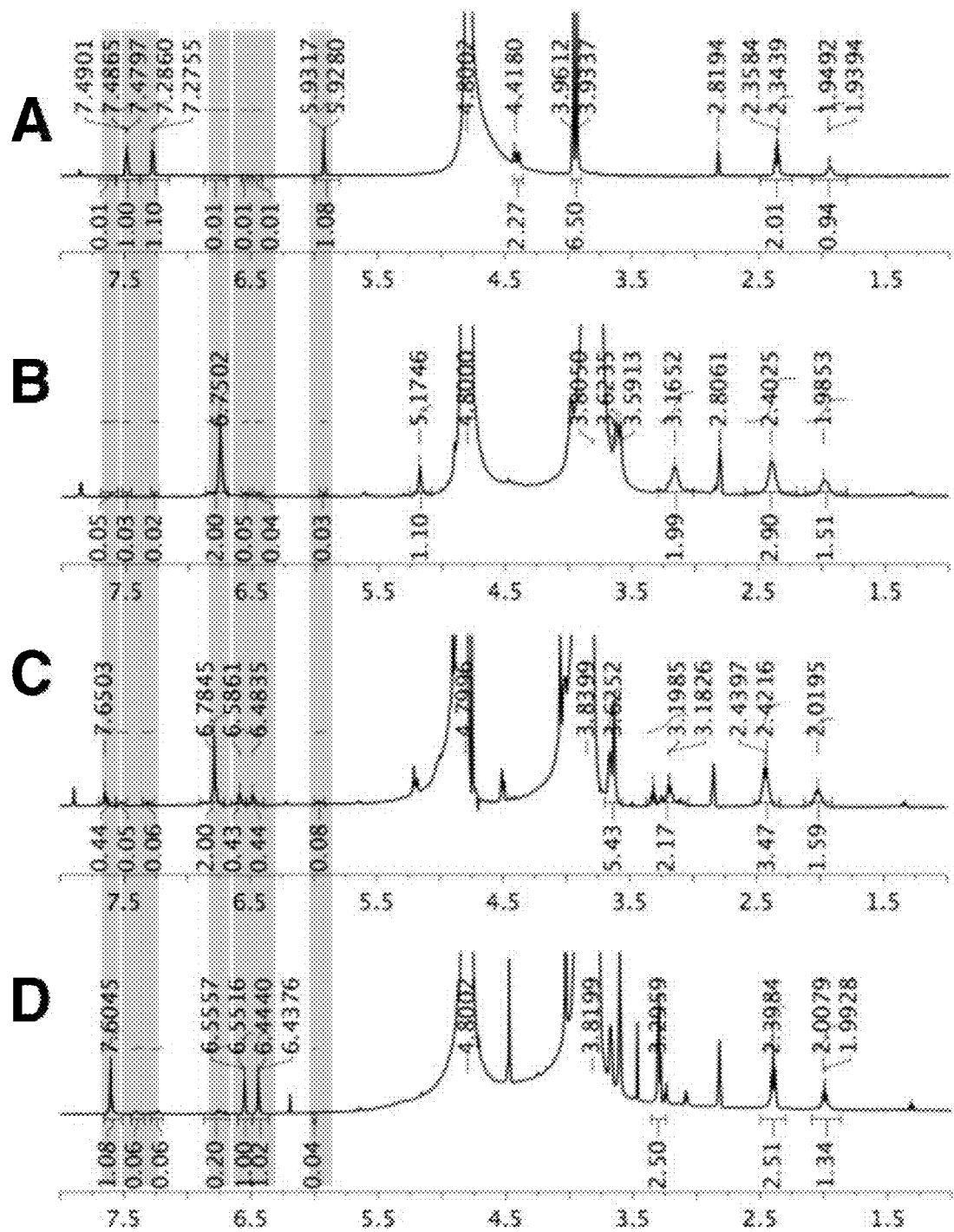
FIG. 10 depicts $^1$H NMR spectra of PEG-OND Hydrogel formed with 4-PEG-SH macromer and bis-ONDs 7a. (A) bis-OND 7a in KDPO$_4$/K$_2$PO$_4$ buffer (pH 7.4), (B) PEG-OND hydrogel from 4-PEG-SH and 7a, 10 mins after mixing at 22° C., (C) Sample at reverse-gelation point, (D) Sample after complete degradation. Second and fifth highlighted vertical band=distinctive OND peaks, third highlighted vertical band=distinctive OND-thiol adduct peaks, first and fourth highlighted vertical band=distinctive furan peaks.

Oscillatory rheology in the linear regime at 37° C. showed the storage modulus (G') to be larger than the loss modulus (G") throughout the gelation process (FIG. 5). G' was found to be frequency-independent and much larger than G" at all frequencies, confirming the solid-like character of these gels (FIG. 1C). No remaining OND linker was observed by $^1$H-NMR after 10 minutes of curing at room temperature (FIG. 10). At pH 6.5, gelation was much slower, with self-supporting gels observed after 20 minutes. The 1,4-disubstituted linker 7c formed only viscous solutions at pH 6.5-7.4. Increasing the buffer pH to 8.0 gave gels with 7c within 1.5 minutes at room temperature. These were fairly stable at a temperature of 4° C., but reverted to the liquid state within 30 minutes at room temperature, as indicated by the crossover between G' and G" in FIG. 1D. This behavior is consistent with the slower rate of conjugate addition, and the faster rate of fragmentation, of the thiol adduct of this 1,4-dialkyl substituted OND electrophile. Gels derived from cleavable OND linkers 7a and 7b collapsed with extended heating at 50° C. (assessed by periodically inverting samples during incubation), while the gel formed using epoxide linker 8 remained intact (FIG. 1B). $^1$H-NMR analysis of representative hydrogels confirmed the conversion of OND-thiol adducts to furan and thiomaleate fragments with the expected first-order kinetic behavior at 37° C. (FIGS. 10-13). Thus, breakdown of the PEG-OND gels occurred by rDA fragmentation of the OND-thiol adducts rather than an alternative process such as amide hydrolysis (FIG. 1A).

Degradation rates of the PEG-OND hydrogels in the absence of swelling buffer varied with temperature and with the identity of OND used to form the gel. Gels derived from OND 7a were stable for more than two weeks at 4° C. by the inversion test, but collapsed after 12 hours at 37° C., and within 3 hours at 50° C. In comparison, gels formed using 7b were stable for more than 60 hours at 37° C., and approximately 13 hours at 50° C. The same trend was observed by time-lapse photography, in which gels were subjected to heating while supporting a glass bead (see S1 video): gels derived from 8 remained intact, and gels derived from 7b were more stable than those made with 7a.

Figure 7:
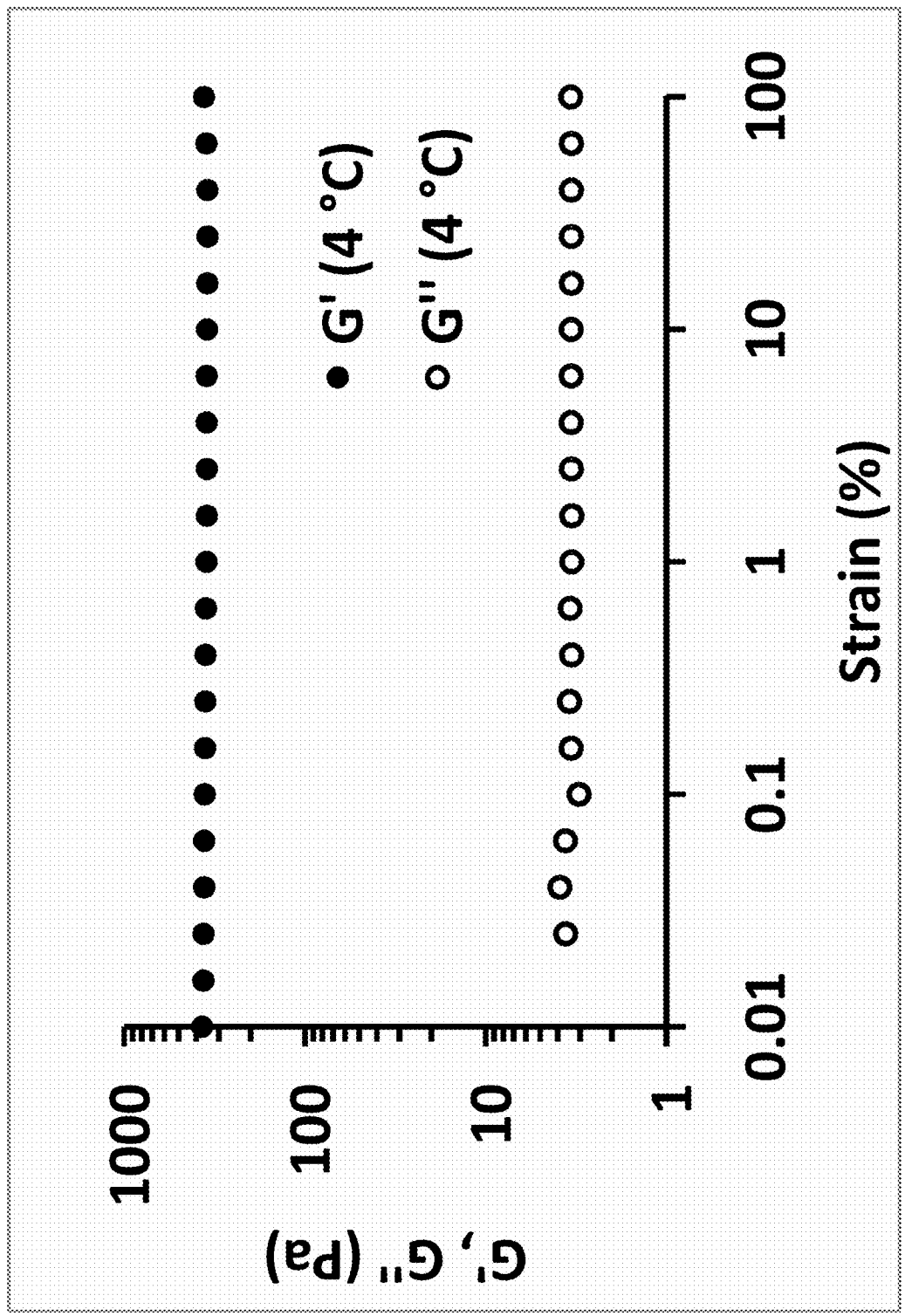
FIG. 7 depicts oscillatory strain sweep of the gel derived from bis-OND 7c and 4-PEG-SH at 4° C. and ω=1 rad/s.

FIG. 1A depicts species formed during degradation of PEG-OND hydrogels. FIG. 1B depicts an inversion test for hydrogel degradation; gels derived from 8 were stable indefinitely. FIG. 1C depicts angular frequency dependence of G' and G" at a fixed strain of 1% at 22° C. for gel formed with 8. Similar data for gels from 7a and 7c are shown in FIGS. 7 and 10. FIG. 1D depicts time dependence of G' and G" for gel formed with linker 7c at a constant strain of 5% and an angular frequency of 1 rad/sec, at 4° C. and 22° C.

Figure 15:
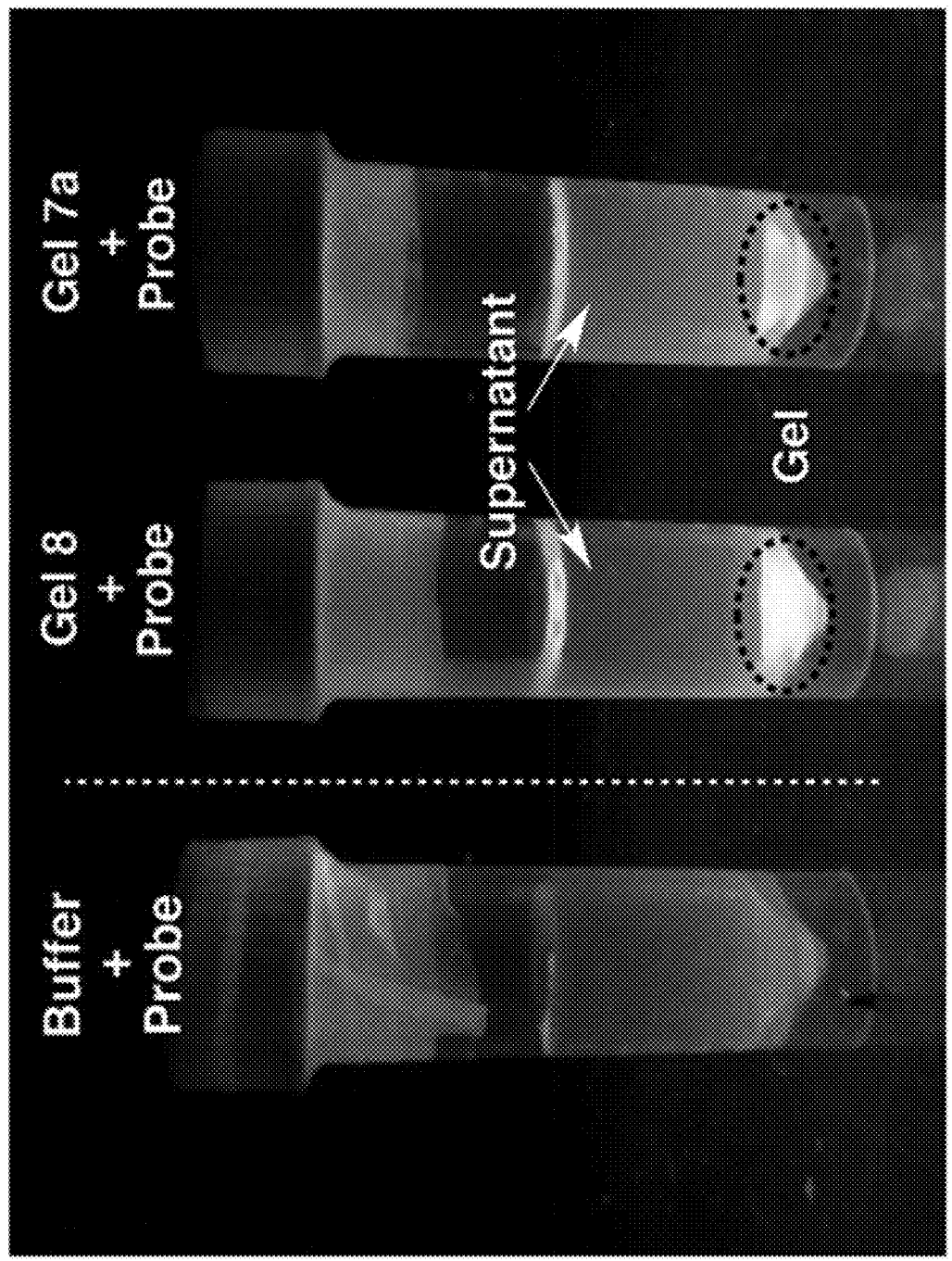
FIG. 15 depicts probe S-6 in pH 7.4 PBS incubated for 18 hours at 4° C. in buffer alone (left), or in the presence of a 60 µL PEG-OND hydrogels formed with linker 8 (middle), and 7a (right). Fluorescent gel and supernatant indicate residual 4-PEG-SH thiols are accessible post-gelation for further modification.

The swelling of the PEG-OND hydrogels in deionized water was measured at 4° C. to prevent significant fragmentation during the experiment. The swollen mass of the gel after 24 hours was compared to the mass at curing to obtain the equilibrium swelling ratio, and residual mass of the gel components after lyophilization was used to calculate the gel fraction, which was found to be >90% for all formulations examined. An independent experiment measuring soluble fraction thiol content yielded results complementing those obtained gravimetrically (Table S3, and related discussion below). With the knowledge that small molecules can readily permeate swollen PEG-OND hydrogels (see below), detecting and modifying residual thiols in gels prepared from divalent linkers 7a and 8 by swelling in the presence of a fluorogenic OND derivative was attempted (FIG. 15, and related discussion below). This treatment yielded fluorescently labeled hydrogels, revealing the presence of residual thiols in the gel network equal to 11.8±3.3% of input macromer thiol content. This result suggests that residual thiols in these materials can be modified post-gelation for the attachment of functional cargo.

Apparent molecular weights between elastic crosslinks ($M_c$) between 3700-4100 g/mol were determined using Flory-Rehner theory (Table 1) from swelling results. These $M_c$ values for gels formed with divalent ONDs (entries 1-5) are lower than the ideal $M_c$ expected for network polymers formed by step-growth polymerization. Similar behavior has been described previously for networks with low chemical crosslinking density, where molecular weight between crosslinks exceeds the entanglement molecular weight for the macromer (~4,400 for PEG). In contrast, the observed $M_c$ values for gels made with ONDs 11 and 12 are greater than the theoretical $M_c$, indicating a lower crosslink density than expected in an ideal network. This may be due to the formation of network defects, such as loops, or incomplete conversion of reactive end groups, as depicted in FIG. 42, made more likely by the increasing valency of these linkers.

TABLE 1

Comparative Hydrogel Swelling Results

| Entry | Linker | Equilibrium Swelling Ratio[a] | Gel Fraction[b] | $M_c$ (g/mol)[c] |
|---|---|---|---|---|
| 1 | 7a | 1.70 ± 0.04[d] | 0.91 ± 0.03 | 4080 ± 57 |
| 2 | 7b | 1.40 ± 0.02 | 0.96 ± 0.02 | 3698 ± 16 |
| 3 | 8 | 1.60 ± 0.10 | 0.97 ± 0.01 | 3900 ± 93 |
| 4 | 10 | 1.87 ± 0.12 | 0.98 ± 0.04 | 4112 ± 94 |
| 5 | 7a + 7b | 1.71 ± 0.04 | 0.99 ± 0.04 | 3981 ± 36 |
| 6 | 11 | 1.54 ± 0.07 | 0.98 ± 0.08 | 3846 ± 102 |
| 7 | 12 | 1.44 ± 0.08 | 0.96 ± 0.05 | 3740 ± 95 |

[a]Mass post-swelling/mass pre-swelling,
[b]Mass of dry residue post-swelling/input mass of OND and 4-PEG-SH,
[c]Calculated using the Flory-Rehner equation, see Supporting Information.
[d]Error represents standard deviation for n = 3 separate gels.

Figures 2A, 2B, 2C:
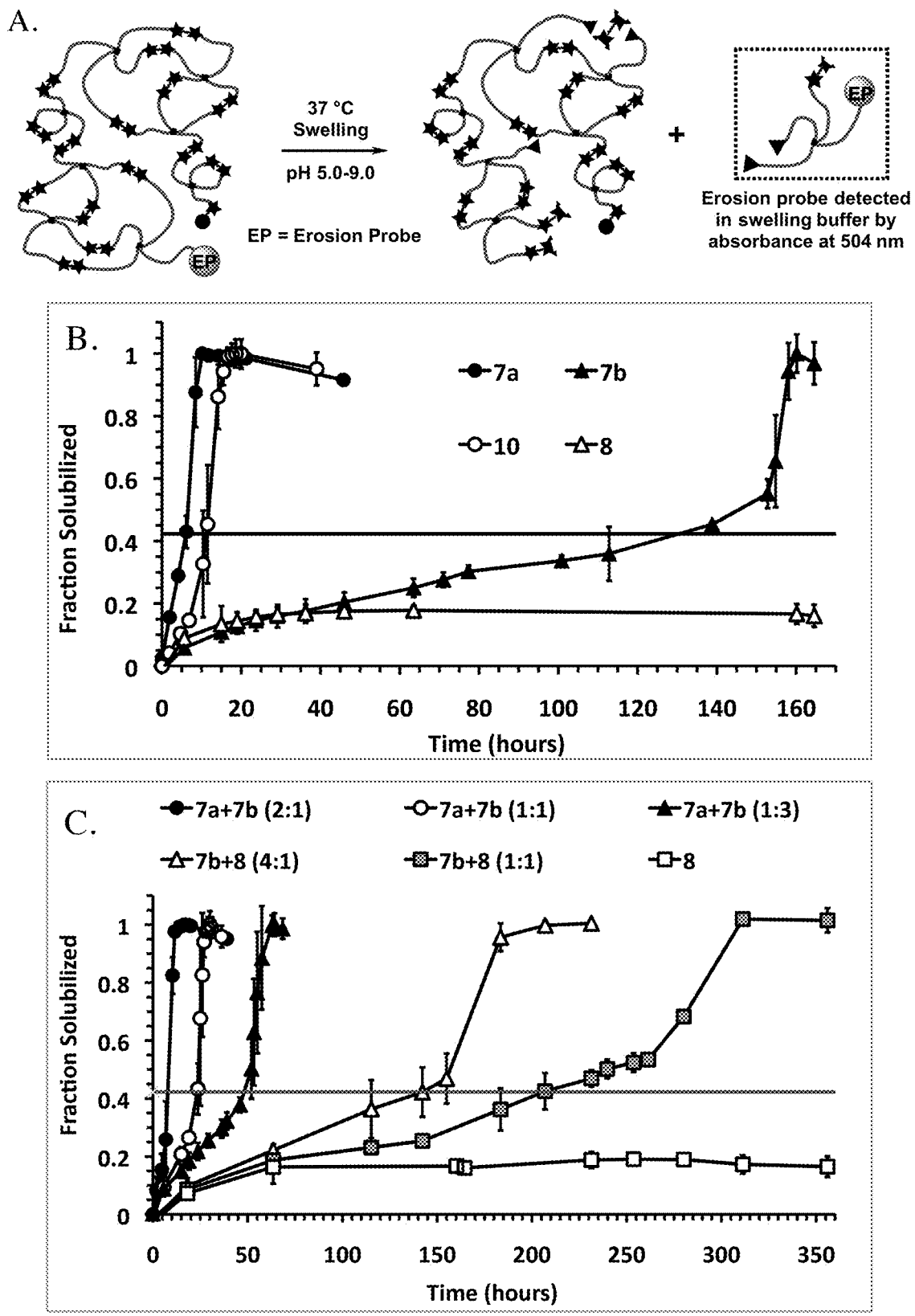
FIG. 2A depicts a schematic of release of erosion probe (EP) during gel degradation.
FIG. 2B depicts erosion profiles resulting from varying OND linker identity.
FIG. 2C depicts erosion profiles resulting from ratios of linkers.
Figure 17:
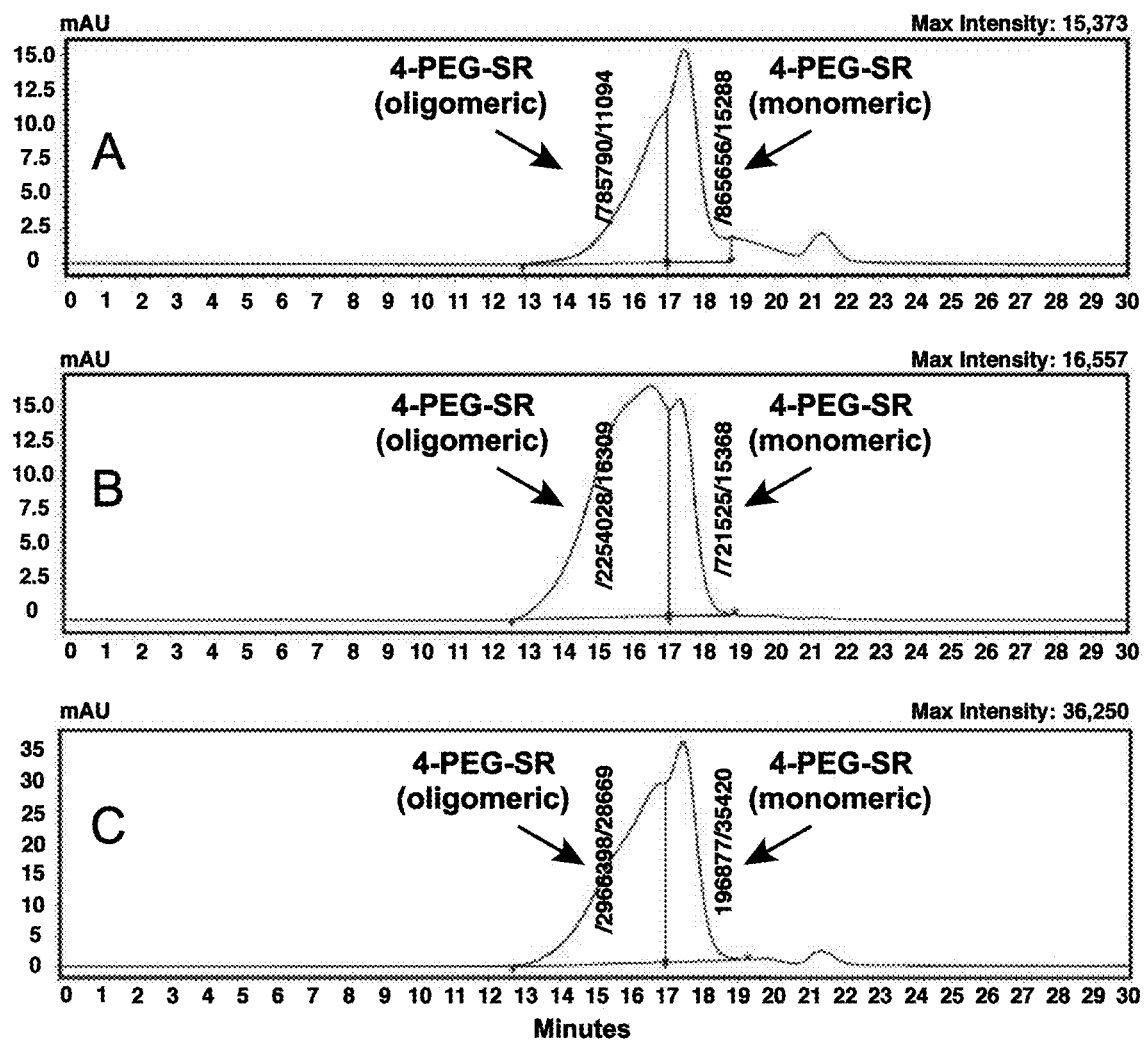
FIG. 17 depicts GPC analysis of supernatant (swelling buffer) of BODIPY-labeled 3.5 wt % hydrogel formed with linker 7b. (A) 64 hours of incubation at 37° C., gel still intact; (B) Sample from A after 180 hours at 37° C., post-disintegration of gel. (C) Sample after 180 hours at 37° C., post-disintegration of gel, no buffer exchanges.
Figure 19:
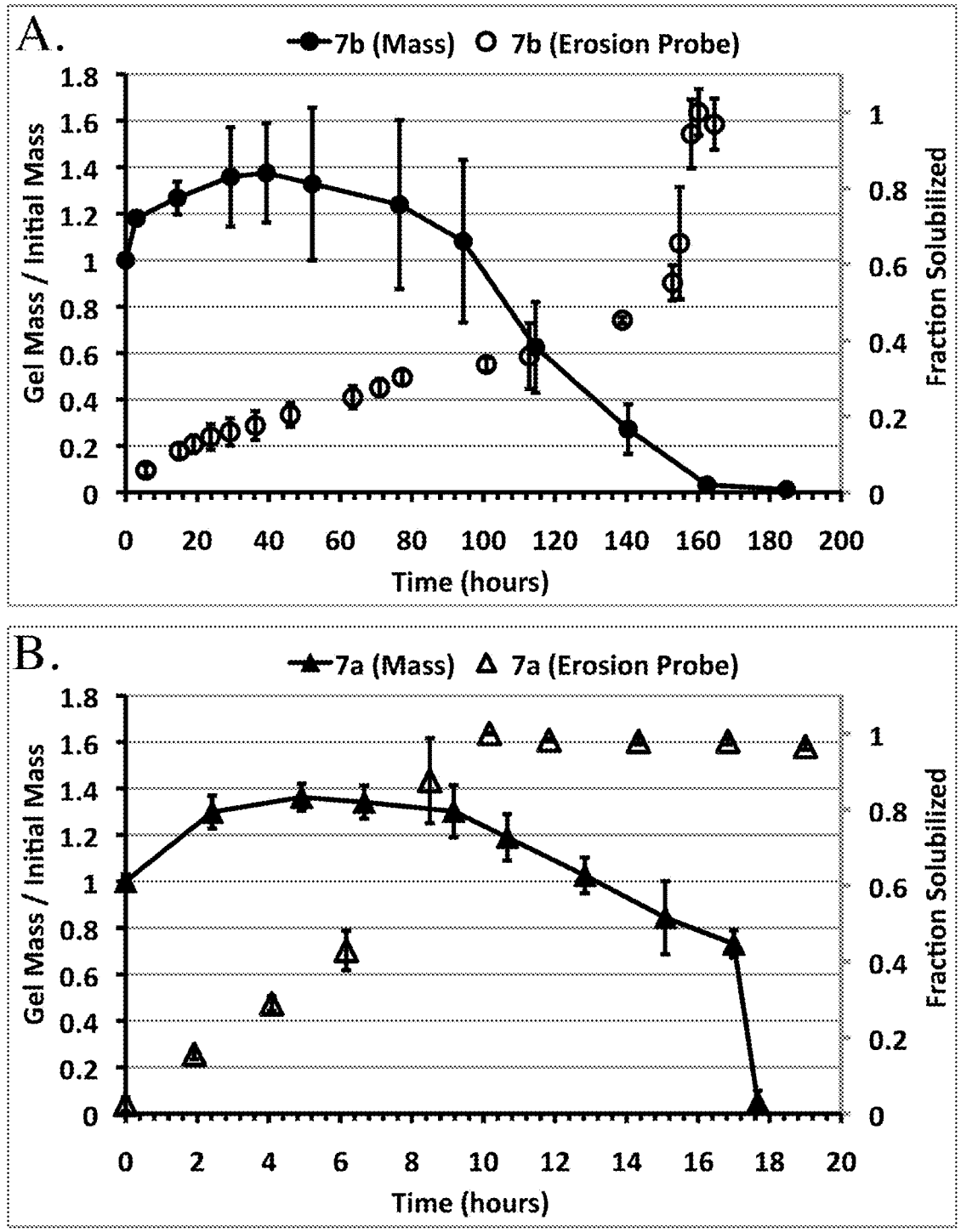
FIG. 19 depicts a comparison of hydrogel erosion for gels prepared with unmodified 4-PEG-SH macromer, or 4-PEG-SH with 3% of end groups modified with a BODIPY-FL erosion probe and bis-OND linkers 7b or 7a (A and B, respectively).

Degradation behavior of PEG-OND hydrogels under swelling conditions was investigated by labeling 3% of the 4-PEG-SH thiols with a BODIPY fluorophore via maleimide coupling before gelation. Gels prepared from this material are expected to have slightly lower crosslink densities and to degrade sooner when compared to gels formed without the erosion probe (FIG. 19). However, the probe-labeled macromer allowed convenient monitoring and comparison of erosion behavior under conditions relevant for biological applications. An increase in absorbance (504 nm) of the swelling buffer was observed as pieces containing the labeled PEG-thiol components were detached from the gel by rDA fragmentation (FIG. 2). Slow release of the BODIPY-labeled PEG was observed, followed by rapid solubilization at the reverse gelation point, which was reached at later times for gels formed with more stable OND adducts, consistent with the relative stabilities observed in unswelled gels (FIG. 2B). Using combinations of linkers, it was possible to produce hydrogels with release profiles tuned between those of gels prepared from a single linker (FIG. 2C). Analysis of supernatants collected during erosion by gel permeation chromatography revealed the presence of monomeric macromer species before reverse gelation, and a larger number of oligomeric macromer species after gel collapse (FIG. 17).

Figures 2D, 2E:
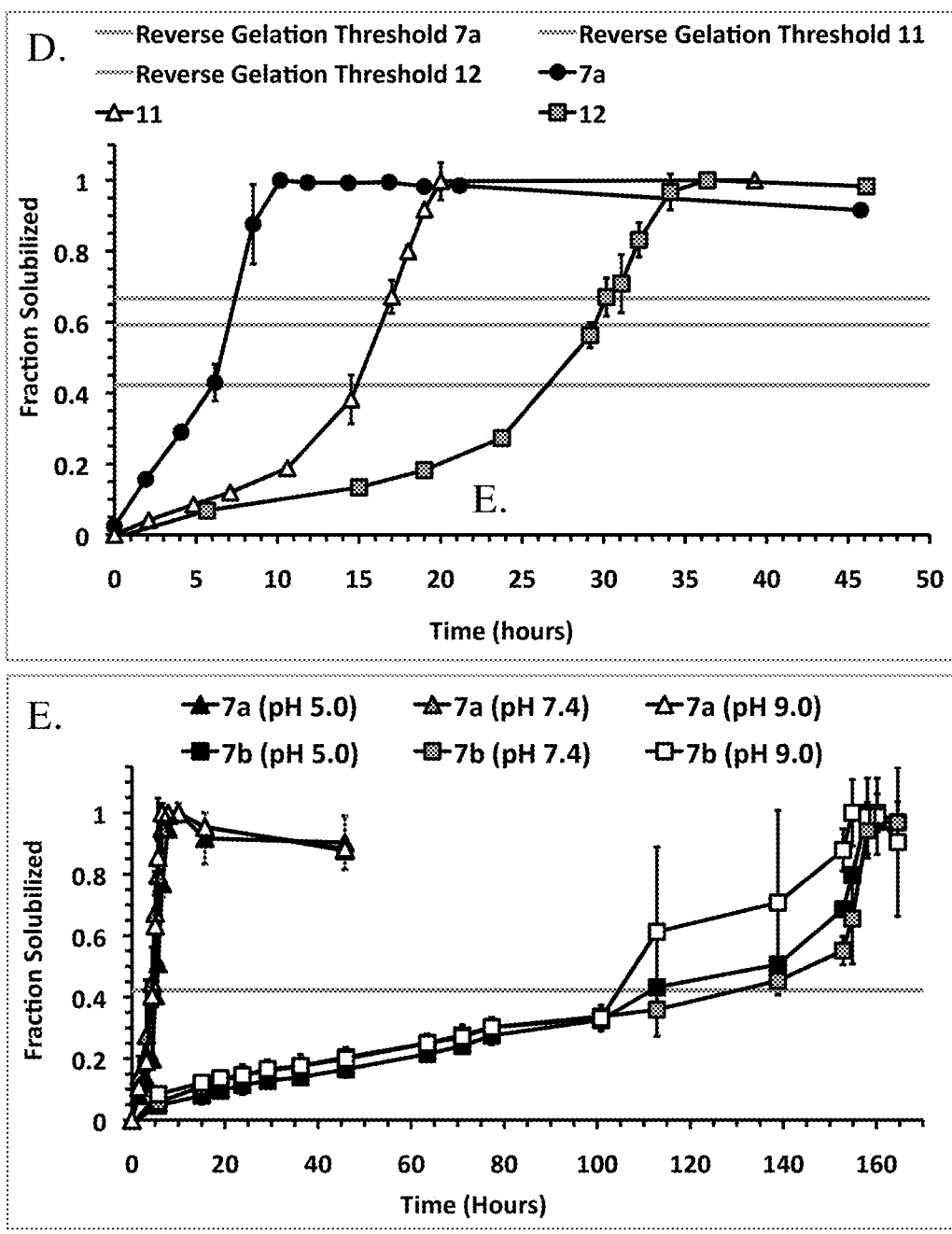
FIG. 2D depicts erosion profiles resulting from OND valence.
FIG. 2E depicts demonstrated insensitivity of erosion behavior to pH of swelling buffer. Dotted lines represent theoretical reverse gelation thresholds.

PEG-OND hydrogels prepared with divalent OND linkers reached the reverse gelation point at a conversion close to the value predicted by Flory and Rehner for step growth gels (dotted lines in FIGS. 2B-E). The higher-valent ONDs 11 and 12 produced more stable gels than those formed from divalent ONDs, but reverse gelation occurred earlier than predicted by theory (FIG. 2D). As with the $M_c$ values noted above, this suggests a less than ideal crosslinking density for these systems in which more attachment points are possible.

FIG. 2A depicts a schematic of release of erosion probe (EP) during gel degradation. FIG. 2B depicts erosion profiles resulting from varying OND linker identity. FIG. 2C depicts erosion profiles resulting from ratios of linkers. FIG. 2D depicts erosion profiles resulting from OND valence. FIG. 2E depicts demonstrated insensitivity of erosion behavior to pH of swelling buffer. Dotted lines represent theoretical reverse gelation thresholds.

In contrast to other hydrogels designed to degrade by hydrolysis, β-elimination, or retro-Michael reactions, it was expected that gels formed with ONDs would exhibit stability profiles largely independent of changes in pH due to the nature of the rDA reaction. Degradation in swelling buffers at pH values ranging from 5.0 to 9.0 yielded very similar erosion profiles (FIG. 2E) and degradation times measured by time-lapse photography (see S2 Video and FIG. 20).

Finally, the diffusion of entrained, rather than covalently anchored, cargos of different sizes out of OND hydrogels of differing stabilities was measured. This was done with a small molecule (carboxyfluorescein), a globular protein (fluorescein-labeled bovine serum albumin, BSA), and a 30-nm protein nanoparticle (fluorescein-labeled bacteriophage Qb virus-like particle). The first and last species have no available thiol groups; the second was reacted with N-ethylmaleimide before gelation to cap cysteine-34 and avoid tethering of the protein cargo to the hydrogel network. Hydrogels derived from 4-PEG-SH and 7a, 7b, or 8 were formed in the presence of each cargo; the speed of this reaction made it highly unlikely that OND connectors were addressed by protein amine groups under these conditions.

Carboxyfluorescein rapidly diffused out of all gels at the same rate ($k_{diffusion}$=0.66±0.03 h$^{-1}$), apparently unhindered by the hydrogel matrix. Bovine serum albumin diffusion was also observed, but was slower ($k_{diffusion}$=0.05±0.01 h$^{-1}$). The decomposition rate of the least stable hydrogel (made with 7a) was competitive with this diffusion, so BSA release from that gel was markedly faster than from the other, more stable, matrices. In contrast, the release of the trapped virus-like particles was largely governed by hydrogel degradation for all of the materials, indicating that the particle diameter exceeded the hydrogel mesh size. As a result, nanoparticles were not released from gels derived from linker 8.

In summary, the conjugate addition and retro-Diels-Alder properties of electron-deficient oxanorbornadienes have been used for the first time to prepare degradable hydrogels with two rare and valuable properties: predictable, widely varying stabilities, and insensitivity of decomposition toward variations in pH. These gels exhibited comparable equilibrium swelling behaviors, indicating similar internal structure and physical properties regardless of the built-in degradation rate. While the most stable degradable hydrogel studied here decomposes after approximately 2 weeks at 37° C., more stable formulations may be desirable for some biomedical applications. Based on the observed erosion behavior, more stable gels should be readily accessible by using higher valence analogs of linkers that produce more stable or non-degradable thiol adducts (e.g., 7b, and 8), as well as increasing the valence of thiol-modified reaction partners. The ease of synthesis of OND linkers, the tunability of material erosion behavior using combinations of a small subset of linkers, and the rapid gelation at physiological pH show great promise for applications of these materials as injectable depots for sustained release.

Below is additional supporting information related to the information summarized above.

General

Materials and Methods

Reagents and solvents were purchased from commercial sources and used as received, unless otherwise stated. When dry solvents were required, solvents were passed through activated alumina columns on a MBraun solvent purification system (MB-SPS), and collected in oven-dried glassware before use. Water was purified on a Millipore Milli-Q Advantage A10 system. Dimethyl acetylenedicarboxylate (DMAD) was purified before use by passing a 50% (v/v) solution in dichloromethane (DCM) through a column of normal phase silica gel (60 mesh), eluting with DCM and condensing under reduced pressure. Unless otherwise stated, the reactions were performed under inert atmosphere in capped reaction vessels. 4-arm thiol-terminated poly(ethylene glycol), (4-PEG-SH), was obtained from JenKem Technologies, USA and stored in a glove box purged with nitrogen. Thiol content was periodically assessed by Ellman's assay. As received, thiol content was ~85% of the expected value. Flash chromatography was performed on 60-mesh silica. Analytical thin layer chromatography (TLC) was performed on aluminum-backed plates and visualized by exposure to UV light and/or staining with aqueous potassium permanganate (2% $KMnO_4$+5% $K_2CO_3$) or ninhydrin stain. Preparative TLC was performed on glass-backed silica gel plates of 1 mm thickness, and visualized with ultraviolet (UV) light. Dye-containing materials were protected from light by wrapping the reaction and storage vessels in aluminum foil.

Instrumentation

Nuclear magnetic resonance (NMR) spectra were obtained on Brüker AMX-400, and DRX-500 instruments in deuterated solvents (Cambridge Isotope Laboratories, Inc.) and referenced to the signals of residual protium in the NMR solvent. Spectra were processed in MestReNova-LITE software (Mestrelab Research). Routine mass spectra were obtained on an Advion Compact Mass Spectrometer (G1946D) ESI-MSD instrument, using direct sample injection followed with 9:1 $CH_3CN:H_2O$ containing 0.1% formic acid as mobile phase. High-resolution mass spectrometry was performed on an Agilent 6230 ESI-TOF LC/MS instrument (G6230B) operating at 4 GHz with internal reference. LC was performed on an Agilent 1260 HPLC with a mobile phase gradient from 0%-90% acetonitrile/water containing 0.1% formic acid on a Zorbax Extend-C18 Rapid Resolution HT (2.1×50 mm, 1.8 µm). Melting points were measured in a Fisher-Johns melting point apparatus and are corrected. IR spectra were recorded on a Nicolet 6700 FTIR spectrophotometer with Smart Performer single-bounce ATR module in thin films or in solids dispersed on a diamond crystal. Absorbance spectra were recorded on an Evolution 220 UV-Vis spectrophotometer (ThermoFisher). Absorbance and fluorescence spectra were also collected on a VarioskanFlash plate reader (ThermoFisher). Rheological measurements were obtained on a Physica MCR 501 rheometer (Anton Paar), equipped with a peltier plate and an evaporation blocker hood. Measurements were taken using a truncated cone-plate geometry (part no. 47709, serial no. 11810), and gels were prepared in situ and trimmed before doing any measurements. Gel permeation chromatography (GPC) analysis was performed in DMF containing 0.1% LiBr additive at 1 mL/min flow rate (LC-20AD pump) on a Shimadzu GPC setup equipped with two Phenomenex Phenogel 10 µm linear columns (300×7.8 mm), autosampler (SIL-20A) and column oven (CTO-20A) set at 40° C. Detection was achieved using a diode array detector (SPD-M20A), and RI detector (RID-10A), and instrument was calibrated with EasiVial poly(methyl methacrylate) standards (Agilent). Time-lapse photography was collected using Chronolapse software (v.1.0.4) and Creative Labs webcam (model VF0070), and photos were compiled using iMovie software (2009, v8.0.6). Still photographs were collected using built-in cameras on iPhone 3 gs and 5c models.

II. Synthetic Procedures

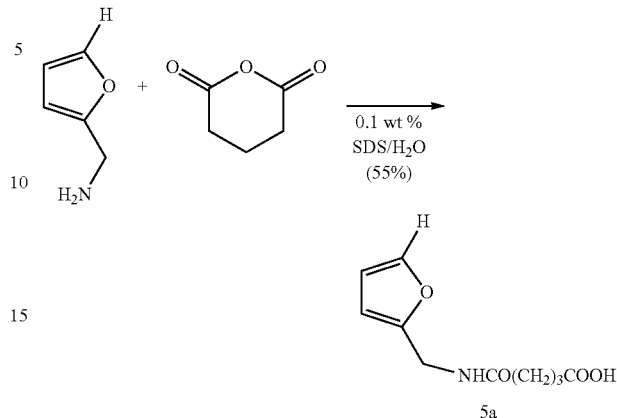

N-glutaroylfurfurylamine, 5a

Glutaric anhydride (2.4 g, 21.2 mmol, 1.18 equiv) was added portion-wise over 10 min to a solution of furfurylamine (1.74 g, 17.9 mmol) in 0.1 wt. % aqueous sodium dodecyl sulfonate (60 mL). The resulting solution was placed at 4° C. overnight. The colorless crystals of the product were filtered, washed with cold water (60 mL), and dried under vacuum, providing 1.67 g (45%) of 5a as colorless crystals. Additional 5a was recovered by EtOAc extraction (3×15 mL) of the filtrate. The residue obtained from the combined organic extracts was dissolved in $H_2O$ (5 mL), filtered, and kept at 4° C. overnight. The colorless crystals of 5a (0.39 g) were combined with the main batch (55% total yield). $R_f$ 0.56 (10% MeOH/EtOAc). $^1$H NMR (500 MHz, $CD_3OD$) δ 7.41 (dd, J=1.8, 0.7 Hz, 1H), 6.33 (dd, J=3.2, 1.9 Hz, 1H), 6.23 (dd, J=3.2, 0.7 Hz, 1H), 4.34 (s, 1H), 2.32 (t, J=7.4 Hz, 1H), 2.26 (t, J=7.5 Hz, 1H), 1.89 (p, J=7.5 Hz, 1H). 13C NMR (126 MHz, $CD_3OD$) δ 176.93, 175.31, 153.24, 143.42, 111.47, 108.17, 49.66, 49.49, 49.43, 49.32, 49.26, 49.15, 48.98, 48.81, 48.64, 37.24, 36.07, 34.15, 22.35. mp: 83-85° C. ESI-MS: $[C_{10}H_{13}NO_4+H]^+$ 212.1.

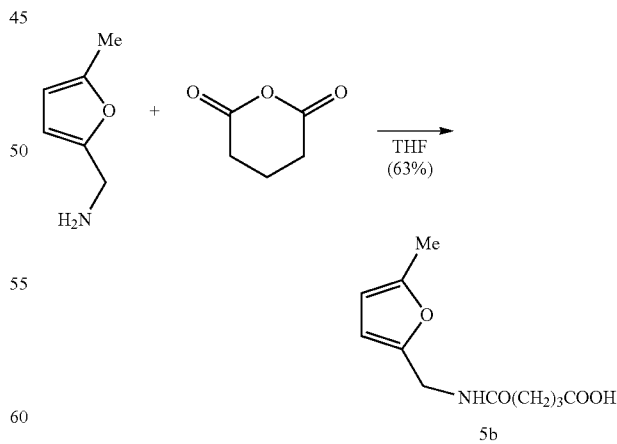

5-methyl-N-glutaroylfurfurylamine, 5b

Glutaric anhydride (299 mg, 2.6 mmol, 1.18 equiv) was added portion-wise over 10 min to a solution of 5-methylfurfurylamine (247 mg, 2.22 mmol, 1 eqiv) in dry THF (7.4 mL). The resulting solution was stirred at room temperature under argon for 3 hours, and then condensed in vacuum. The residue was taken up in 10 mL ethyl acetate (EtOAc) and washed with water (10 mL) and 1 M HCl (2×10 mL). The aqueous layers were back extracted once with 20 mL EtOAc, and the combined organic layers were dried over anhydrous sodium sulfate ($Na_2SO_4$), filtered and condensed in vacuum. The organic crude was further purified by flash column chromatography on silica gel, eluting with a gradient from EtOAc through 10% MeOH/EtOAc to yield an off-white crystalline solid (318 mg, 63% yield). $R_f$ 0.59 (10% MeOH/EtOAc). $^1$H NMR (500 MHz, $CDCl_3$) δ 10.65 (brs, 1H), 6.08 (d, J=3.0 Hz, 1H), 6.04 (s, 1H), 5.90-5.83 (m, 1H), 4.36 (d, J=5.4 Hz, 2H), 2.41 (t, J=7.1 Hz, 2H), 2.29 (t, J=7.4 Hz, 2H), 2.25 (s, 3H), 1.96 (p, J=7.2 Hz, 2H). $^{13}$C NMR (126 MHz, $CDCl_3$) δ 178.14, 172.49, 152.21, 149.25, 108.64, 106.49, 77.48, 77.23, 76.97, 36.91, 35.35, 33.18, 33.08, 20.82, 13.70. ESI-MS: $[C_{11}H_{15}NO_4+H^+]$=226.1.

on $SiO_2$ gel, eluting with a gradient from ethyl acetate through 10% methanol in ethyl acetate to yield a white crystalline solid (129 mg), which was combined with the previously collected precipitate (57% total). $R_f$ 0.74 (10% MeOH/EtOAc with 0.1% acetic acid). $^1$H NMR (500 MHz, DMSO-d6) δ 8.29 (t, J=5.6 Hz, 2H), 7.53 (dd, J=1.8, 0.8 Hz, 2H), 6.36 (dd, J=3.1, 1.9 Hz, 2H), 6.20 (dd, 3.1, 0.8 Hz, 2H), 4.23 (d, J=5.7 Hz, 4H), 2.10 (t, J=7.5 Hz, 4H), 1.72 (p, J=7.6 Hz, 2H). $^{13}$C NMR (126 MHz, DMSO) δ 172.18, 152.57, 142.26, 110.73, 106.99, 40.01, 39.93, 39.84, 39.76, 39.68, 39.60, 39.51, 39.42, 39.34, 39.18, 39.01, 35.65, 34.82, 21.66. mp: 154-156° C. LC-HRMS: $[C_{15}H_{18}N_2O_4+H^+]$ calc: 291.1339, obs: 291.1341. rt: 4.941 min (0-90% MeCN/$H_2O$).

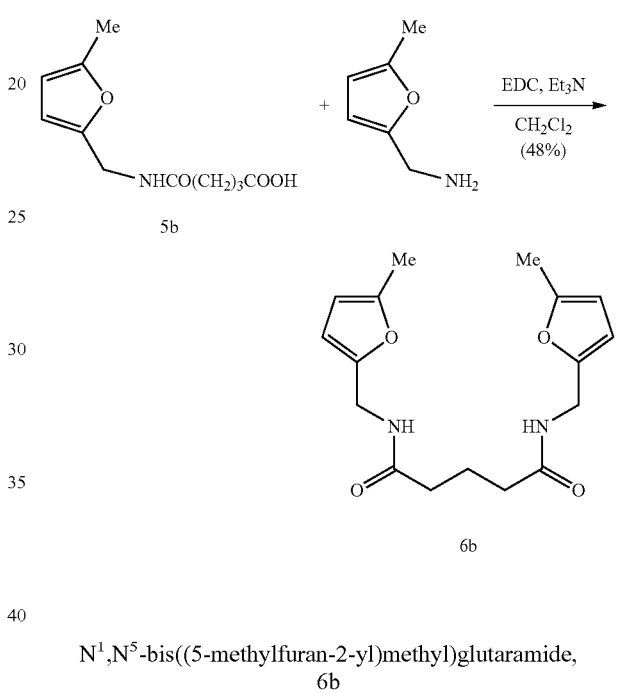

$N^1,N^5$-bis((5-methylfuran-2-yl)methyl)glutaramide, 6b

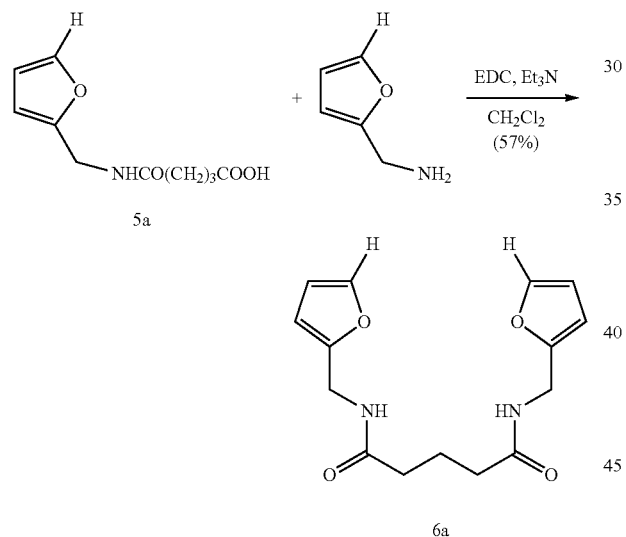

$N^1,N^5$-bis(furan-2-ylmethyl)glutaramide, 6a

Compound 5a (750 mg, 3.551 mmol, 1 equiv), EDC.HCl (816.8 mg, 4.261 mmol, 1.2 equiv), and triethylamine (1.48 mL, 10.65 mmol, 3 equiv) were dissolved in dichloromethane (50 mL) at room temperature and stirred for 10 minutes before addition of furfurylamine (345 µL, 3.906 mmol, 1.1 eq) and 30 mg dimethylaminopyridine. The resulting mixture was stirred at room temperature overnight to yield a pale yellow suspension. The precipitate of the desired product was collected by filtration, washing with dichloromethane (459 mg). Additional product was recovered from the filtrate was condensed and taken up in 35 mL ethyl acetate and washed with 2×35 mL 0.1 N HCl and 1×35 mL saturated $NaHCO_3$. The organic layer was dried over $Na_2SO_4$, filtered and condensed in vacuum. The crude product obtained in the organic layer was further purified by flash chromatography Compound 5b (634 mg, 2.816 mmols, 1 equiv), EDC.HCl (648 mg, 3.38 mmol, 1.2 equiv), and triethylamine (1.48 mL, 10.65 mmol, 2.5 equiv) were dissolved in dichloromethane (19 mL) at room temperature and stirred for 10 minutes before addition of 5-methylfurfurylamine (345 µL, 3.10 mmol, 1.1 eq) and 30 mg dimethylaminopyridine. The resulting mixture was stirred at room temperature for 20 hours. The reaction mixture was condensed and partitioned between ethyl acetate (30 mL) and water (30 mL). Organic layer was washed with 1×20 mL saturated $NaHCO_3$ and 1×20 mL 1 M HCl. The organic layer was dried over anhydrous sodium sulfate, filtered and condensed in vacuum. Solid residue dissolved in chloroform with heating and allowed to stand to form crystals which were collected by vacuum filtration, washing with chilled chloroform (432 mg, 48%). $R_f$ 0.74 (5% MeOH/EtOAc). $^1$H NMR (500 MHz, $CD_3OD$) δ 6.08 (d, J=2.7 Hz, 2H), 6.01-5.84 (d, J=2.6 Hz, 2H), 4.27 (s, 4H), 2.29 2.16 (m, 10H), 1.90 (p, J=7.5 Hz, 2H). $^{13}$C NMR (126 MHz, $CD_3OD$) δ 175.25, 153.00, 151.31, 109.07, 107.31, 49.66, 49.49, 49.32, 49.27, 49.15, 48.98, 48.81, 48.64, 37.41, 36.26, 23.28, 13.48. ESI-MS: $[C_{17}H_{22}N_2O_4+H^+]$=319.2.

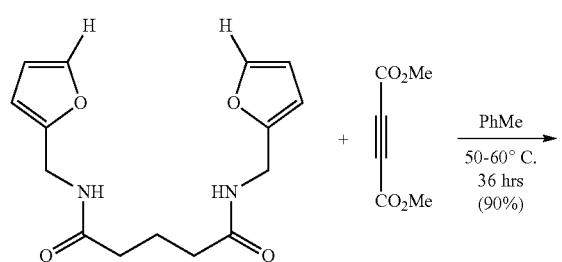

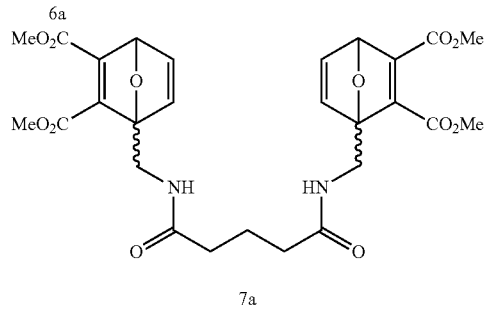

Tetramethyl 1,1'-((glutaroylbis(azanediyl))bis(methylene))bis(7-oxabicyclo[2.2.1] hepta-2,5-diene-2,3-dicarboxylate), 7a Bis-furan 6a (152 mg, 0.532 mmol, 1 equiv) and dimethyl acetylenedicarboxylate (163 µL, 1.33 mmol, 2.5 equiv) were combined with 600 µL toluene in a sealed vial purged with argon and heated directly on a hotplate set at 60° C. for 36 hours. The resulting slurry was suspended in diethyl ether and triturated. The resulting pale precipitate was collected by vacuum filtration and the filter cake was dried in high vacuum to yield a white solid comprised of an inseparable mixture of Bis-OND diastereomers (275 mg, 90%). $R_f$ 0.67 (10% MeOH/EtOAc). $^1$H NMR (500 MHz, CDCl$_3$) δ 7.21 (dd, J=5.2, 1.9 Hz, 2H), 7.04 (d, J=5.2 Hz, 2H), 6.36 (brs, 1H), 6.28 (brs, 1H), 5.64 (t, J=1.9 Hz, 2H), 4.21-4.08 (m, 2H), 4.03-3.97 (m, 2H), 3.83 (app. d, J=2.1 Hz, 6H), 3.78 (app. d, J=1.4 Hz, 6H), 2.18 (t, J=6.9 Hz, 4H), 1.95 (p, J=6.9 Hz, 2H). $^{13}$C NMR (126 MHz, CD$_3$OD) δ 172.84, 172.72, 164.12, 164.09, 162.77, 162.75, 153.80, 153.78, 153.07, 152.98, 145.41, 143.63, 143.53, 97.30, 97.21, 83.79, 83.76, 77.48, 77.23, 76.98, 52.78, 52.77, 52.59, 52.58, 37.71, 37.68, 34.93, 34.80, 21.82, 21.80. FT-IR (cm$^{-1}$): 3307, 2954, 1711, 1643, 1531, 1432, 1236, 1201, 1121. mp: 163-167° C. LC-HRMS: [C$_{27}$H$_{30}$N$_2$O$_{12}$+H$^+$] calc: 575.1872, obs: 575.1885. rt: 5.620 min (0-90% MeCN/H$_2$O).

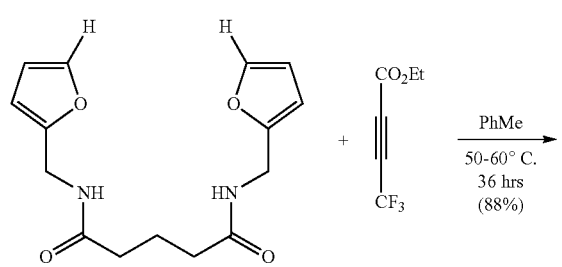

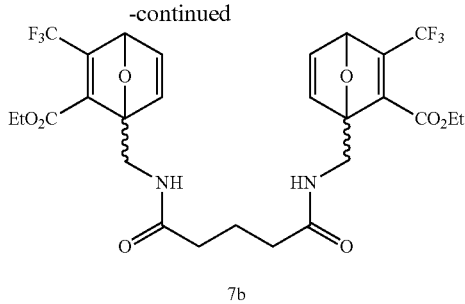

Diethyl 1,1'-((glutaroylbis(azanediyl))bis(methylene))bis(3-(trifluoromethyl)-7-oxabicyclo[2.2.1] hepta-2,5-diene-2-carboxylate), 7b Bis-furan 6a (50 mg, 0.172 mmol, 1 equiv) and ethyl 4,4,4-trifluoro-2-butynoate (59 µL, 0.413 mmol, 2.4 equiv) were combined with 500 µL toluene in a sealed vial purged with argon, and heated directly on a hotplate set at 60° C. for 40 hours. The resulting slurry was suspended in diethyl ether and triturated. The resulting pale precipitate was collected by vacuum filtration and the filter cake was washed with ether and dried in high vacuum to yield an off-white solid comprised of an inseparable mixture of Bis-OND isomers (94.5 mg, 88%). $R_f$ 0.47 (10% MeOH/CH$_2$Cl$_2$). $^1$H NMR (500 MHz, CDCl$_3$) δ 7.19 (dd, J=5.1, 1.6 Hz, 2H), 7.11 (dd, J=5.1, 1.7 Hz, 2H), 6.33-6.15 (m, 2H), 5.58 (s, 2H), 4.42-4.19 (m, 4H), 4.19-4.00 (m, 4H), 2.17 (t, J=6.7 Hz, 4H), 1.94 (p, J=6.5 Hz, 2H), 1.31 (t, J=7.1 Hz, 6H). $^{13}$C NMR (126 MHz, CD$_3$OD) δ 172.77, 172.74, 162.49, 162.42, 151.74, 151.64, 151.45, 151.34, 151.25, 151.21, 151.17, 151.13, 144.70, 144.67, 144.21, 144.18, 124.79, 122.64, 120.50, 118.36, 97.30, 97.22, 82.66, 82.64, 82.62, 77.48, 77.23, 76.98, 62.35, 37.72, 37.68, 34.95, 22.03, 21.96, 14.05. $^{19}$F NMR (471 MHz, CDCl3) δ−62.80, −64.04, −64.13. FT-IR (cm$^{-1}$): 3303, 3083, 2961, 1720, 1640, 1549, 1302, 1267, 1134, 701. mp: 166-169° C. LC-HRMS: [C$_{27}$H$_{28}$F$_6$N$_2$O$_{14}$+H$^+$] calc: 623.1823, obs: 623.1847. rt: 8.124 min (0-90% MeCN/H$_2$O).

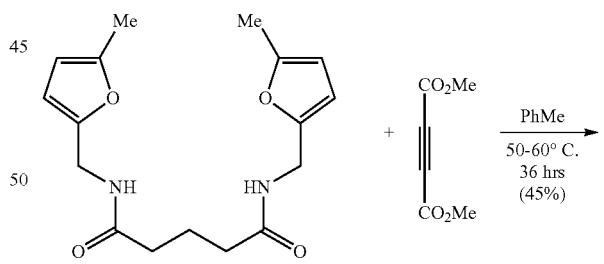

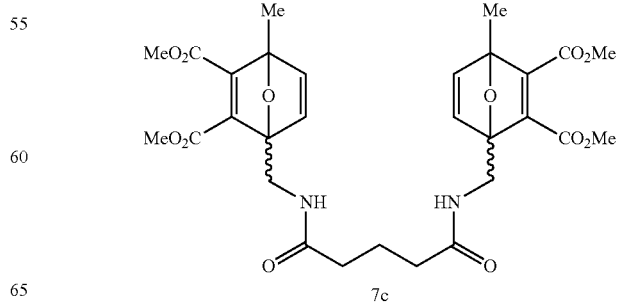

Tetramethyl 4,4'-((glutaroylbis(azanediyl))bis(methylene))bis(1-methyl-7-oxabicyclo[2.2.1]hepta-2,5-diene-2,3-dicarboxylate), 7c Bis-furan 6b (102.5 mg, 0.322 mmol, 1 equiv) and dimethyl acetylenedicarboxylate (98.1 µL, 0.805 mmol, 2.5 equiv) were combined with 1 mL toluene in a sealed vial purged with argon, and heated directly on a hotplate set at 60° C. for 36 hours. The resulting slurry was suspended in diethyl ether and triturated. The resulting syrup was loaded onto a packed silica gel column and eluted with a gradient from hexane through 3% MeOH/EtOAc to yield an off-white glassy residue comprised of an inseparable mixture of Bis-OND isomers (86.4 mg, 45%). $R_f$ 0.45 (2% MeOH/EtOAc). $^1$H NMR (500 MHz, CDCl$_3$) δ 7.07 (d, J=5.1 Hz, 1H), 7.00 (d, J=5.1 Hz, 1H), 6.95-6.94 (m, 2H), 6.55 (t, J=5.9 Hz, 1H), 6.36 (t, J=5.8 Hz, 1H), 4.34 (dd, J=14.7, 7.0 Hz, 1H), 4.09 (dd, J=14.7, 5.9 Hz, 1H), 4.01 (dd, J=14.7, 6.0 Hz, 1H), 3.83 (d, J=5.2 Hz, 1H), 3.80-3.74 (m, 11H), 2.18 (t, J=6.8 Hz, 4H), 1.93 (p, J=6.8 Hz, 2H), 1.76 (app. d, J=5.9 Hz, 6H). $^{13}$C NMR (126 MHz, CD$_3$OD) δ 172.99, 172.83, 164.38, 164.27, 163.66, 163.37, 157.20, 156.62, 152.01, 151.36, 147.83, 147.59, 145.57, 144.96, 95.32, 95.20, 92.75, 92.71, 77.48, 77.23, 76.98, 52.64, 52.62, 52.53, 52.51, 37.93, 37.84, 35.05, 34.88, 22.33, 22.11, 15.39, 15.31. FT-IR (cm$^{-1}$): 3375, 2954, 1713, 1650, 1537, 1436, 1248, 1142. LC-HRMS: [C$_{29}$H$_{34}$N$_2$O$_{14}$+H$^+$] calc: 603.2185, obs: 603.2199. rt: 6.341 min (0-90% MeCN/H$_2$O).

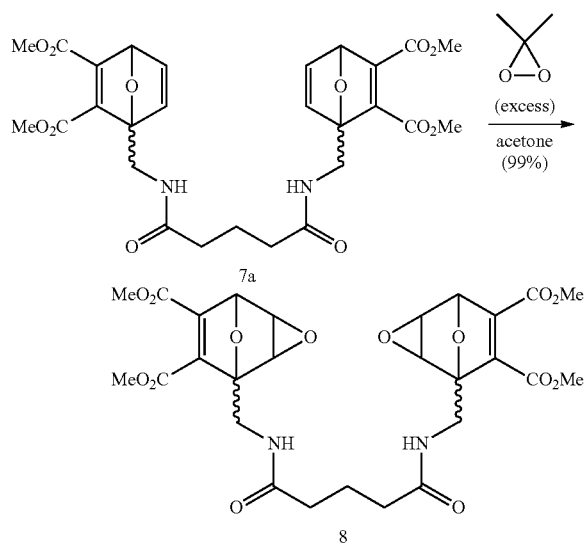

Tetramethyl 1,1'-((glutaroylbis(azanediyl))bis(methylene))bis(3,8-dioxatricyclo[3.2.1.0$^{2,4}$]oct-6-ene-6,7-dicarboxylate), 8

Bis-OND 7a (52 mg, 0.091 mmol, 1 equiv) was dissolved in 3.36 mL of a freshly prepared ~0.07 M solution of dimethyldioxirane in acetone. The reaction mixture was stirred at room temperature overnight, and then condensed in vacuo to yield an off-white solid (54.3 mg, 99%). No further purification was necessary. $R_f$ 0.38 (10% MeOH/EtOAc). $^1$H NMR (500 MHz, CDCl$_3$) δ 6.85 6.80 (m, 2H), 5.01 (app. d, J=12.2 Hz, 2H), 4.10 (dd, J=14.9, 6.3 Hz, 1H), 3.93-3.92 (m, 2H), 3.84-3.71 (m, 17H), 2.34-2.11 (m, 4H), 1.94 (p, J=6.5 Hz, 2H). $^{13}$C NMR (126 MHz, CD$_3$OD) δ 173.48, 173.31, 163.37, 163.15, 162.03, 161.95, 149.93, 149.86, 147.07, 146.89, 91.45, 91.10, 78.42, 78.40, 57.53, 56.93, 56.66, 53.10, 53.05, 52.83, 36.96, 36.87, 34.28, 34.16, 21.67, 21.34. FT-IR (cm$^{-1}$): 3367, 2955, 1713, 1666, 1530, 1433, 1238, 731. mp: 125-130° C. LC-HRMS: [C$_{27}$H$_{30}$N$_2$O$_{14}$+H$^+$] calc: 607.1770, obs: 607.1779. rt: 5.072 min (0-90% MeCN/H$_2$O).

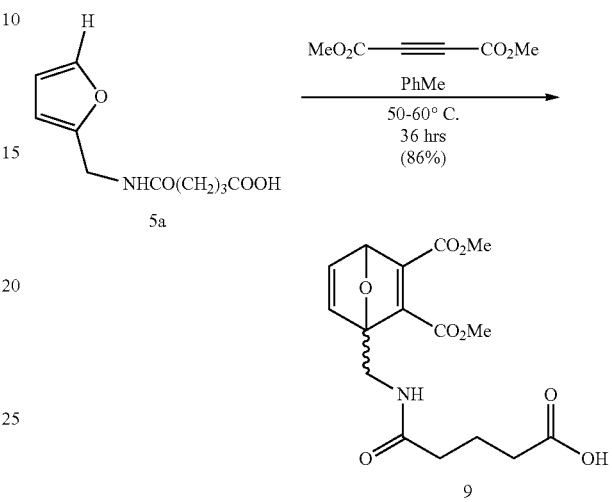

5-(((2,3-bis(methoxycarbonyl)-7-oxabicyclo[2.2.1]hepta-2,5-dien-1-yl)methyl) amino)-5-oxopentanoic acid, 9

Furan 5a (999 mg, 4.73 mmol, 1 equiv) was combined with dimethyl acetylenedicarboxylate (814 µL, 6.622 mmols, 1.4 equiv) and 1 mL toluene in a sealed vial and heated directly on a hot plate at 60° C. while stirring for 5 hours. The reaction mixture was then diluted with 15 mL diethyl ether and triturated to yield an off-white precipitate that was collected by vacuum filtration and dried to constant mass under high vacuum (1.434 g, 86%). $R_f$ 0.57 (10% MeOH/EtOAc with 0.5% AcOH). $^1$H NMR (500 MHz, DMSO-d$_6$) δ 8.04 (s, 1H), 7.30 (dd, J=5.1, 1.7 Hz, 1H), 7.10 (d, J=5.2 Hz, 1H), 5.69 (d, J=1.8 Hz, 1H), 3.93 (dd, J=14.8, 6.6 Hz, 1H), 3.78 (dd, J=14.9, 5.3 Hz, 1H), 3.71 (app. d, J=4.2 Hz, 6H), 2.19 (t, J=7.4 Hz, 2H), 2.10 (t, J=7.4 Hz, 2H), 1.68 (p, J=7.5 Hz, 2H). $^{13}$C NMR (126 MHz, DMSO-d$_6$) δ 175.06, 172.81, 164.75, 163.22, 154.85, 152.78, 146.11, 144.37, 83.78, 53.10, 40.86, 40.69, 40.53, 40.36, 40.20, 40.03, 39.86, 37.40, 34.96, 33.86, 21.46. FT-IR (cm$^{-1}$): 3354, 2955, 1709, 1635, 1544, 1435, 1236. ESI-MS: [C$_{16}$H$_{19}$NO$_8$+H$^+$]=354.1.

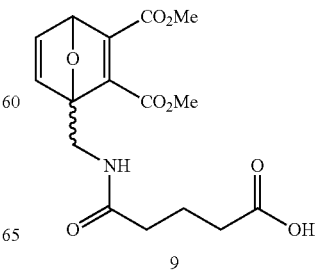

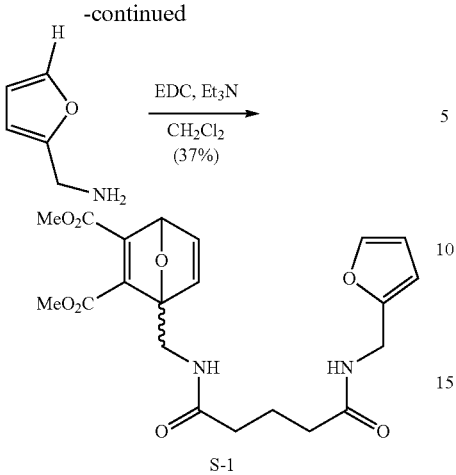

Dimethyl 1-((5-((furan-2-ylmethyl)amino)-5-oxo-pentanamido)methyl)-7-oxabicyclo [2.2.1]hepta-2,5-diene-2,3-dicarboxylate, S-1

OND 9 (199 mg, 0.563 mmol, 1.2 equiv) was dissolved in 3 mL $CH_2Cl_2$ and dicyclohexylcarbodiimide (136 mg, 0.788 mmols, 1.4 equiv) was added. The resulting solution was stirred at 4° C. for 15 minutes before addition of 41 µL (0.469 mmol, 1 eq) furfurylamine. The reaction mixture was allowed to reach room temperature and stirred for 6 hours before filtration and removal of solvent under reduced pressure. The crude was taken up in 10 mL ethyl acetate and washed with 1×10 mL 1 M HCl and 1×10 mL saturated $NaHCO_3$. The organic layer was dried over sodium sulfate, filtered and condensed in vacuum. The organic crude was further purified by silica gel column chromatography, eluting with a gradient from hexanes to 5% MeOH/EtOAc to yield a white solid (76 mg, 37%). $R_f$ 0.63 (10% MeOH/EtOAc with 0.5% AcOH). $^1$H NMR (500 MHz, $CDCl_3$) δ 7.33-7.30 (m, 1H), 7.19 (dd, J=5.2, 1.9 Hz, 1H), 6.98 (d, J=5.3 Hz, 1H), 6.59 (s, 1H), 6.28 (dd, J=3.0, 1.9 Hz, 1H), 6.18 (t, J=2.7 Hz, 1H), 6.16-6.09 (m, 1H), 5.59 (d, J=1.9 Hz, 1H), 4.47-4.29 (m, 2H), 4.23 (dd, J=14.8, 7.0 Hz, 1H), 3.87 (dd, J=14.8, 4.9 Hz, 1H), 3.80 (s, 3H), 3.75 (s, 3H), 2.25-2.18 (m, 4H), 1.98-1.86 (m, 2H). $^{13}$C NMR (126 MHz, $CDCl_3$) δ 172.68, 172.62, 164.14, 162.66, 153.82, 153.14, 151.79, 145.55, 143.06, 142.14, 110.62, 110.60, 107.35, 97.23, 83.79, 77.48, 77.23, 76.98, 52.80, 52.56, 37.66, 36.46, 35.00, 34.98, 21.75. ESI-MS: $[C_{21}H_{24}N_2O_8+H^+]$= 433.2.

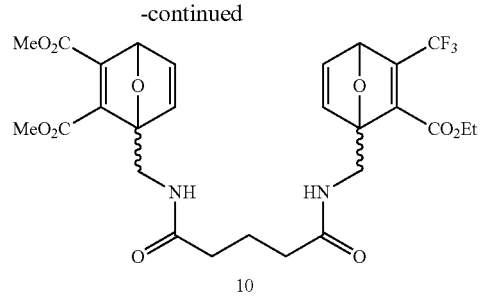

Dimethyl 1-((5-(((2-(ethoxycarbonyl)-3-(trifluoromethyl)-7-oxabicyclo[2.2.1]hepta-2,5-dien-1-yl)methyl)amino)-5-oxopentanamido)methyl)-7-oxabicyclo[2.2.1]hepta-2,5-diene-2,3-dicarboxylate, 10

Asymmetric OND-furan S-1 (75.5 mg, 0.175 mmol, 1.0 equiv) was combined with ethyl 4,4,4-trifluoro-2-butynoate (32.5 µL, 0.228 mmols, 1.3 equiv), and 500 µL toluene in a sealed vial under argon. The mixture was heated directly on a hot plate at 60° C. for 48 hours. After cooling to room temperature, 3.5 mL diethyl ether was added to yield a pale yellow precipitate, which was collected by vacuum filtration. The solid was further purified by flash column chromatography on silica gel, eluting with a gradient from hexanes through 5% MeOH/EtOAc to yield a pale yellow solid (90 mg, 86%). $R_f$ 0.38 (EtOAc). $^1$H NMR (500 MHz, $CDCl_3$) δ 7.21 (dd, J=5.2, 1.8 Hz, 1H), 7.19-7.13 (m, 1H), 7.11 (dd, J=5.2, 1.5 Hz, 1H), 7.03 (dd, J=5.2, 3.6 Hz, 1H), 6.36-6.35 (m, 1H), 6.22-6.18 (m, 1H), 5.63 (d, J=1.8 Hz, 1H), 5.57 (br s, 1H), 4.35-4.20 (m, 2H), 4.18-3.95 (m, 4H), 3.82 (m, 3H), 3.77 (s, 3H), 2.23-2.10 (m, 4H), 1.93 (p, J=6.7 Hz, 2H), 1.31 (t, J=7.1 Hz, 3H). $^{13}$C NMR (126 MHz, $CDCl_3$) δ 172.84, 172.80, 172.74, 172.69, 164.15, 164.05, 162.80, 162.71, 162.44, 162.37, 153.77, 153.64, 153.12, 153.07, 151.67, 151.58, 151.37, 151.29, 151.25, 151.24, 151.21, 151.19, 145.48, 145.42, 144.61, 144.32, 144.25, 143.53, 143.45, 124.78, 122.64, 120.50, 118.36, 97.34, 97.24, 97.22, 97.18, 83.80, 83.78, 82.65, 82.63, 82.61, 82.59, 77.48, 77.23, 76.97, 62.30, 52.81, 52.79, 52.60, 52.59, 37.78, 37.73, 37.63, 34.96, 34.91, 34.87, 21.95, 21.89, 14.06, 14.04. FT-IR ($cm^{-1}$): 3300, 2954, 1716, 1640, 1547, 1436, 1296, 1265, 1122, 702. mp: 93-97° C. LC-HRMS: $[C_{27}H_{29}F_3N_2O_{10}+H^+]$ calc: 599.1847, obs: 599.1889. rt: 6.950 min (0-90% $MeCN/H_2O$).

Scheme S1. Synthesis of Tris-OND electrophile 11.

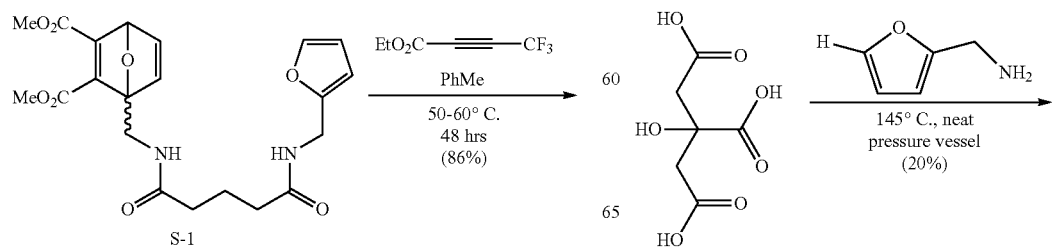

-continued

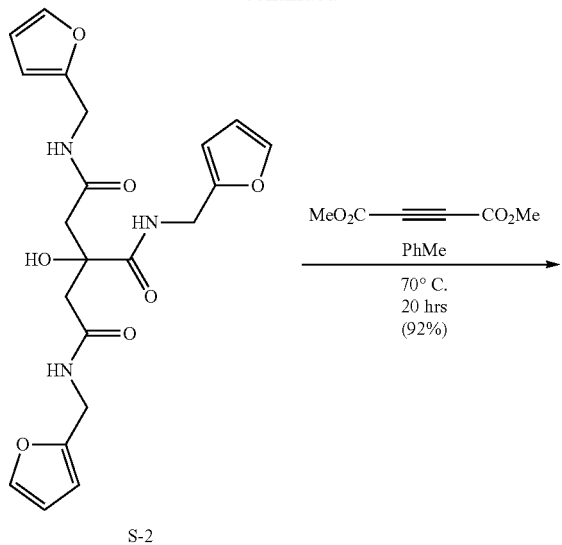

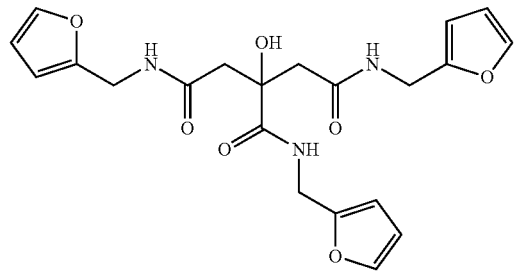

N¹,N²,N³-tris(furan-2-ylmethyl)-2-hydroxypropane-1,2,3-tricarboxamide, S-2

Thermal amidation reactions presented here for the preparation of S-2 and S-4 are unoptimized and were performed using a modified procedure that has been previously described in Krysmann et al., 134 J. AM. CHEM. SOC'Y 747, 747-50 (2012), the procedure being incorporated herein by reference in its entirety. Briefly, citric acid (1.00 g, 4.76 mmol, 1 equiv) combined with 1.282 mL furfurylamine (14.51 mmol, 3.05 equiv) in a 25 mL pressure vessel and 500 mg 4 Å molecular sieves and a stir bar were added. The solution was heated at 145° C. under argon for 3 hours, and then cooled to room temperature. The crude was dissolved in $CH_2Cl_2$ and purified by flash chromatography on silica gel, eluting with a gradient from hexanes through 5% MeOH/EtOAc to yield a pale yellow solid (398 mg, 20%). $R_f$ 0.34 (EtOAc). $^1H$ NMR (500 MHz, $CDCl_3$) δ 7.40 (t, J=5.5 Hz, 1H), 7.33-7.31 (m, 1H), 7.31-7.28 (m, 1H), 7.12 (br s, 2H), 6.63 (s, 1H), 6.29 (dd, J=3.1, 1.9 Hz, 1H), 6.27 (dd, J=3.0, 1.9 Hz, 2H), 6.18 (d, J=2.7 Hz, 3H), 4.39 (dd, J=15.5, 5.7 Hz, 2H), 4.32 (dd, J=15.1, 5.5 Hz, 4H), 2.75 (d, J=14.7 Hz, 2H), 2.59 (d, J=14.7 Hz, 2H). $^{13}C$ NMR (126 MHz, $CDCl_3$) δ 173.79, 170.59, 151.13, 150.95, 142.47, 142.40, 110.67, 110.63, 107.67, 107.59, 77.48, 77.23, 76.98, 75.67, 42.83, 36.67, 36.57. FT-IR ($cm^{-1}$): 3295, 3115, 2926, 1644, 1526, 1192, 1013. LC-HRMS: [$C_{21}H_{23}N_3O_7$+H⁺] calc: 430.1609, obs: 430.1615. rt: 6.141 min (0-90% MeCN/$H_2O$).

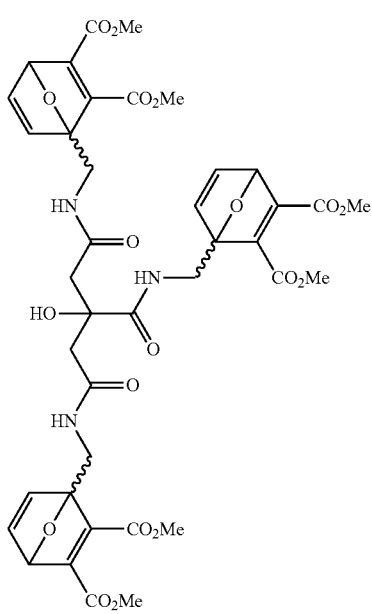

11

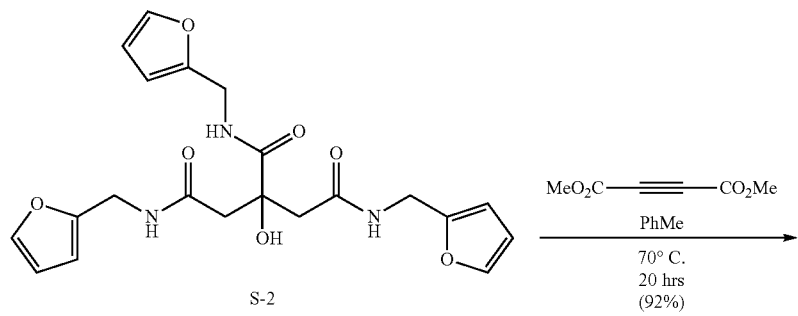

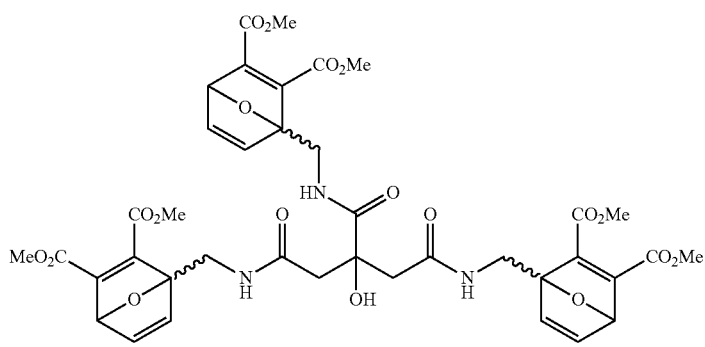

Tetramethyl 1,1'-(((2-(2-(((2,3-bis(methoxycarbonyl)-7-oxabicyclo[2.2.1]hepta-2,5-dien-1-yl)methyl)amino)-2-oxoethyl)-2-hydroxysuccinyl)bis(azanediyl))bis(methylene))bis(7'-oxabicyclo[2.2.1]hepta-2,5-diene-2,3-dicarboxylate), 11

Tris-furan S-2 (100.2 mg, 0.233 mmol, 1.0 equiv) was combined with dimethyl acetylenedicarboxylate (115 μL, 0.9334 mmols, 4 equiv) and 100 μL toluene in a sealed vial. The vial was purged with argon and heated directly on a hot plate at 70° C. for 20 hours. The reaction was then cooled to room temperature and purified by flash chromatography on silica gel, eluting with a gradient from ethyl acetate through 10% MeOH/EtOAc to yield a pale foaming solid (184.5 mg, 92%). $R_f$ 0.10 (EtOAc). $^1$H NMR (500 MHz, CDCl$_3$) δ 7.42-7.38 (m, 1H), 7.17-7.16 (m, 3H), 7.04-6.88 (m, 5H), 6.30 (dd, J=9.2, 3.4 Hz, 1H), 5.59 (dd, J=4.3, 1.8 Hz, 3H), 4.19-3.89 (m, 6H), 3.78-3.74 (overlapping singlets, 18H), 2.75-2.59 (m, 2H), 2.57-2.50 (m, 2H). $^{13}$C NMR (126 MHz, CDCl$_3$) δ 173.95, 173.90, 173.88, 173.84, 170.84, 170.81, 170.78, 170.73, 170.72, 164.05, 164.01, 163.99, 163.98, 162.89, 162.88, 162.83, 162.82, 153.48, 153.46, 153.40, 153.28, 153.24, 153.18, 153.13, 145.36, 145.31, 143.31, 143.22, 143.17, 143.15, 96.85, 96.84, 96.75, 96.74, 96.72, 83.87, 83.85, 83.81, 77.48, 77.23, 76.98, 75.27, 75.24, 75.22, 75.19, 52.68, 52.48, 42.70, 42.60, 42.54, 37.83, 37.76, 37.66. FT-IR (cm$^{-1}$): 3368, 2954, 1711, 1692, 1526, 1435, 1232, 712. LC-HRMS: [C$_{39}$H$_{41}$N$_3$O$_{19}$+H$^+$] calc: 856.2407, obs: 856.2428. rt: 6.727 min (0-90% MeCN/H$_2$O).

Scheme S2. Synthesis of Tetra-OND electrophile 12.

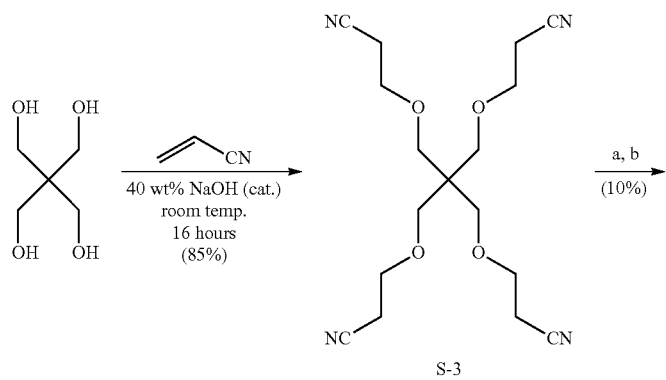

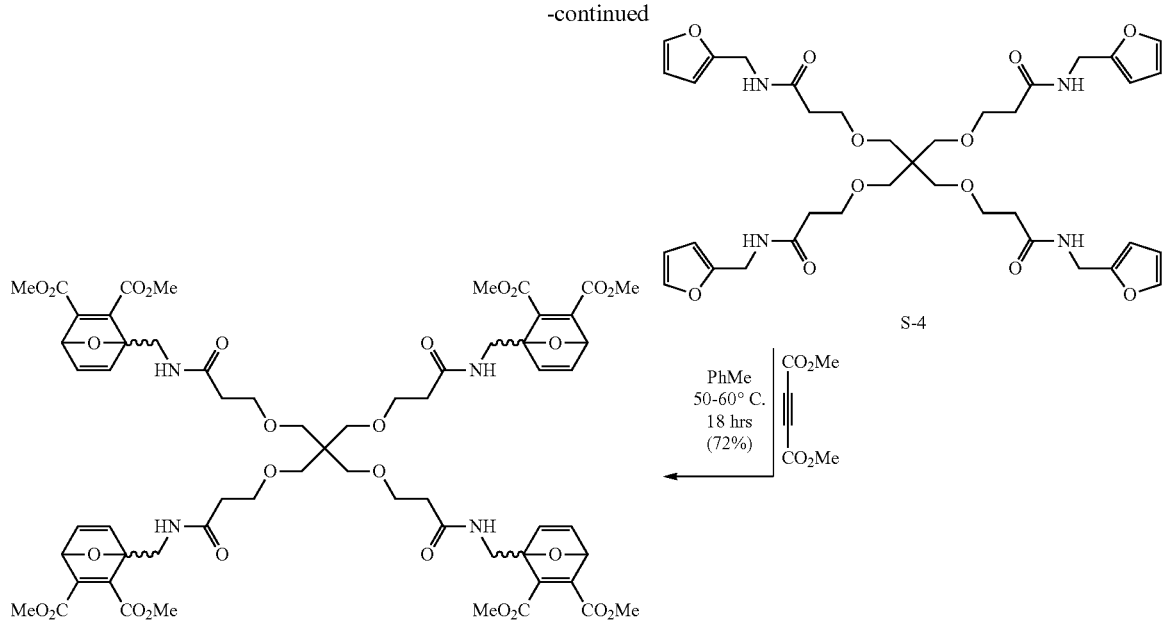

(a) conc. HCl, reflux, 4 hrs followed by extraction. (b) 1 equiv. furfurylamine, 145° C., neat, pressure vessel, followed by flash chromatography.

3,3'-((2,2-bis((2-cyanoethoxy)methyl)propane-1,3-diyl)bis(oxy))dipropanenitrile, S-3

Tetra-nitrile S-3 was prepared using a previously described protocol in Weizman et al., 118 J. Am. Chem. Soc'y 12368. 12368-75 (1996), the procedure being incorporated herein by reference in its entirety. Briefly, pentaerythriotol (1.00 g, 7.34 mmol, 1 equiv.) was combined with acrylonitrile (2.175 mL, 33.03 mmols, 4.5 equiv.) at room temperature and 100 µL of 40 wt % aqueous sodium hydroxide was added. The mixture was stirred under nitrogen at room temperature for 24 hours. The crude was taken up in 20 mL 1N HCl and 20 mL ethyl acetate. The aqueous layer was extracted with a second volume of ethyl acetate, and the combined organic layers were washed once with brine, dried over anhydrous sodium sulfate, filtered and condensed under reduced pressure to yield a colorless oil that solidified on storage to a white solid (2.1794 g, 85%). Spectra are consistent with previously reported data. $R_f$ 0.16 (50% EtOAC/Hexane). $^1$H NMR (500 MHz, CDCl$_3$) δ 3.48 (t, J=6.1 Hz, 3H), 3.30 (s, 3H), 2.45 (t, J=6.1 Hz, 3H). $^{13}$C NMR (126 MHz, CDCl$_3$) δ 118.03, 77.49, 77.23, 76.97, 68.22, 65.25, 45.08, 18.19.

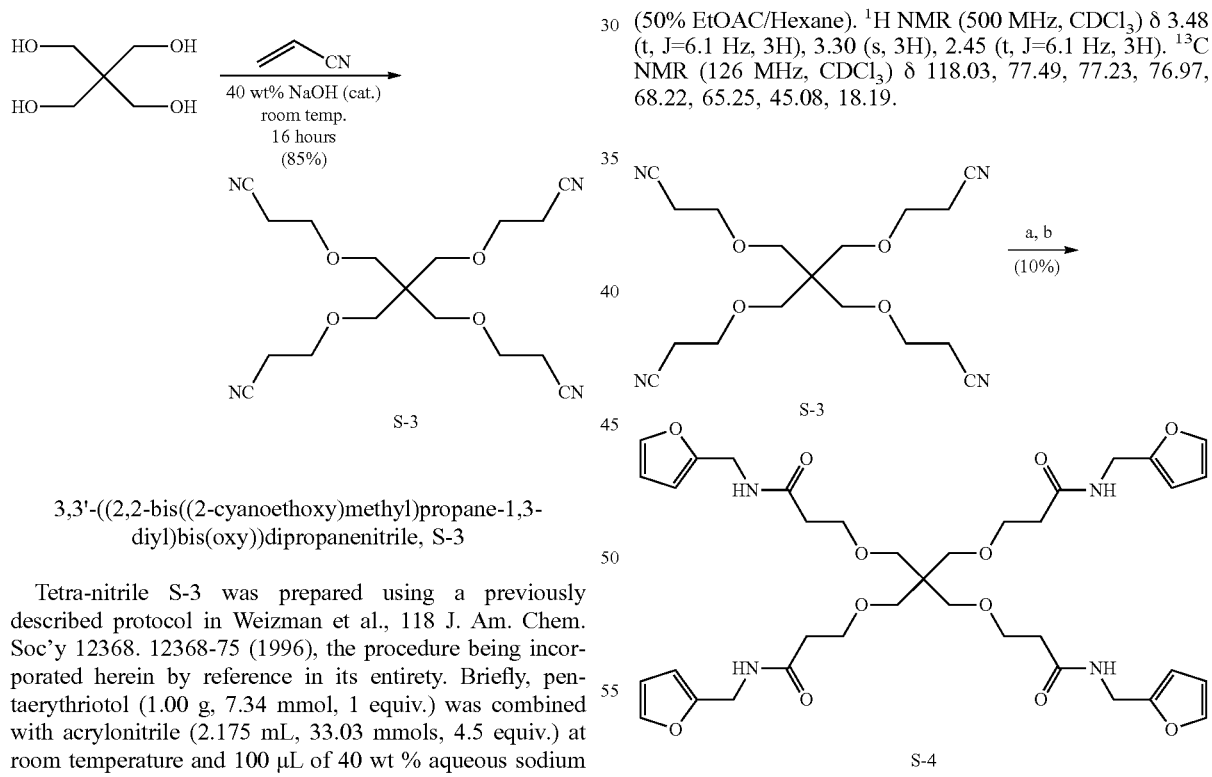

(a) conc. HCl, reflux, 4 hrs. (b) 1 equiv. furfurylamine, 145° C., neat, pressure vessel.

3,3'-(2,2-bis((3-((furan-2-ylmethyl)amino)-3-oxopropoxy)methyl)propane-1,3-diyl)bis(oxy))bis(N-(furan-2-ylmethyl)propanamide), S-4

Tetra-furan S-4 was prepared from the crude tetra-carboxylate formed by a previously described hydrolysis of tetra-nitrile S-3.[2] Briefly, the tetra-nitrile (1.5141 g, 4.35 mmols) was dissolved in 3 mL concentrated HCl and refluxed at 100° C. under nitrogen for 4 hours. The crude was suspended in 50 mL ethyl acetate and washed with 20 mL of water. The water layer was extracted with 4×20 mL EtOAc, and the organic layers were dried over anhydrous sodium sulfate and condensed at reduced pressure to yield a colorless viscous syrup (1.5 g, 81%). No further purification was performed, and consumption of nitrile was confirmed by FT-IR and $^{13}$C NMR. A portion of this syrup (492 mg, ~1.16 mmols) was combined with 430.2 μL furfurylamine (4.87 mmols, 4.2 equiv), 100 mg 4 Å molecular sieves and a stir bar in a sealed tube and heated at 145° C. for 4 hours, then cooled to room temperature. The brown syrup was partitioned between 20 mL CH$_2$Cl$_2$ and 20 mL saturated sodium bicarbonate. The organic layer was washed with 20 mL 1 M HCl, and 20 mL brine before being dried over anhydrous sodium sulfate, filtering and condensing in vacuum. The organic crude was further purified by flash chromatography on silica gel, eluting with a gradient from ethyl acetate through 10% MeOH/EtOAc to yield a white solid (77 mg, 10%). R$_f$ 0.44 (10% MeOH/EtOAc). $^1$H NMR (500 MHz, CDCl$_3$) δ 7.37-7.28 (m, 4H), 6.96-6.77 (m, 4H), 6.34-6.25 (m, 4H), 6.19 (d, J=3.1 Hz, 4H), 4.39 (d, J=5.6 Hz, 8H), 3.55 (t, J=5.7 Hz, 8H), 3.17 (s, 8H), 2.36 (t, J=5.7 Hz, 8H). $^{13}$C NMR (126 MHz, CDCl$_3$) δ 171.55, 151.71, 142.22, 110.67, 107.59, 77.48, 77.23, 76.98, 68.93, 67.30, 45.33, 36.76, 36.55. ESI-MS: [C$_{37}$H$_{48}$N$_4$O$_{12}$+H$^+$]=740.0

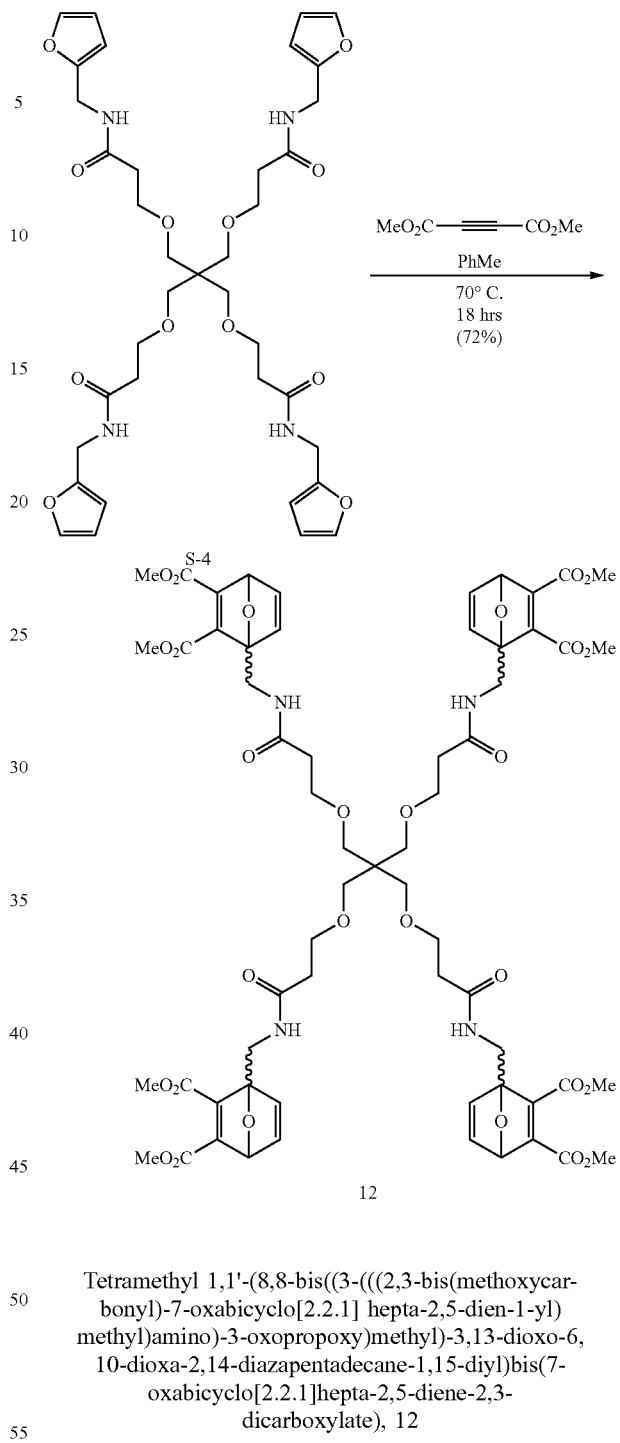

3,3'-((2-((3-((furan-2-ylmethyl)amino)-3-oxo-propoxy)methyl)-2-(hydroxymethyl) propane-1,3-diyl)bis(oxy))bis(N-(furan-2-ylmethyl)propanamide), S-4'

In addition to the desired product, tris-furan S-4' was also obtained (149.2 mg, 22%), presumably due to retro-Michael addition reaction during the thermal amidation. R$_f$ 0.33 (10% MeOH/EtOAc). $^1$H NMR (500 MHz, CDCl$_3$) δ 7.34-7.28 (m, 3H), 6.88 (d, J=30.8 Hz, 3H), 6.28 (dd, J=3.1, 1.8 Hz, 3H), 6.19 (d, J=3.2 Hz, 3H), 4.39 (d, J=5.5 Hz, 6H), 3.57 (dt, J=23.7, 5.7 Hz, 6H), 3.43 (s, 2H), 3.22 (d, J=59.5 Hz, 6H), 2.81 (s, 1H), 2.39 (t, J=5.7 Hz, 6H). $^{13}$C NMR (126 MHz, CDCl$_3$) δ 171.49, 151.70, 151.65, 142.24, 142.21, 110.64, 107.58, 77.48, 77.23, 76.98, 71.03, 70.31, 68.91, 67.48, 67.40, 67.28, 63.91, 63.78, 45.19, 36.72, 36.65, 36.55. ESI-MS: [C$_{29}$H$_{39}$N$_3$O$_{10}$+H$^+$]=590.0

Tetramethyl 1,1'-(8,8-bis((3-(((2,3-bis(methoxycarbonyl)-7-oxabicyclo[2.2.1] hepta-2,5-dien-1-yl)methyl)amino)-3-oxopropoxy)methyl)-3,13-dioxo-6,10-dioxa-2,14-diazapentadecane-1,15-diyl)bis(7-oxabicyclo[2.2.1]hepta-2,5-diene-2,3-dicarboxylate), 12

Tetra-furan S-4 (76.9 mg, 0.104 mmols, 1 equiv) was combined with dimethyl acetylenedicarboxylate (64 μL, 0.519 mmols, 5 equiv.) and 200 μL toluene in a sealed 4 mL vial. The mixture was heated while stirring directly on a hot plate for 18 hours at 70° C. The crude was then purified by flash chromatography on silica gel, eluting with a gradient from ethyl acetate through 10% MeOH/EtOAc to yield an off-white foaming solid (98.4 mg, 72%). R$_f$ 0.23 (10% MeOH/EtOAc). $^1$H NMR (500 MHz, CDCl$_3$) δ 7.16 (dd, J=5.2, 1.8 Hz, 4H), 6.98 (d, J=5.2 Hz, 4H), 6.65 (t, J=5.8 Hz, 4H), 5.59 (d, J=1.8 Hz, 4H), 4.15-4.03 (m, 4H), 3.99-3.94

(m, 4H), 3.76 (two singlets, 24H), 3.56 (t, J=5.5 Hz, 8H), 3.25 (s, 8H), 2.37 (t, J=5.8 Hz, 8H). $^{13}$C NMR (126 MHz, CDCl$_3$) δ 171.68, 163.99, 162.71, 153.99, 152.77, 145.36, 143.30, 97.23, 83.73, 77.48, 77.43, 77.23, 76.98, 69.47, 67.38, 52.65, 52.50, 45.26, 37.70, 36.73. FT-IR (cm$^{-1}$): 3365, 2954, 1713, 1652, 1537, 1435, 1264, 1200, 1098, 714. LC-HRMS: [C$_{61}$H$_{72}$N$_4$O$_{28}$+H$^+$] calc: 1309.4406, obs: 1309.4413. rt: 7.147 min (0-90% MeCN/H$_2$O).

Supplementary Note on Epoxidation Reactions

In some embodiments, conversion of the OND to the corresponding epoxyoxanorbornene (EONB) can be facilitated in high conversion using either dimethyldioxirane (DMDO) or 3-chloroperoxybenzoic acid (mCPBA). In addition to epoxidation of bis-OND 7a to bis-EONB 8, test epoxidations were carried out with mono-, tri- and tetravalent ONDs. Reactions with mono- and tris-ONDs proceeded smoothly. While epoxidation was observed in the case of tetra-OND 12 with DMDO, the reaction was complicated by the presence of ether linkages in the linker core structure, which are easily oxidized by DMDO reagent.

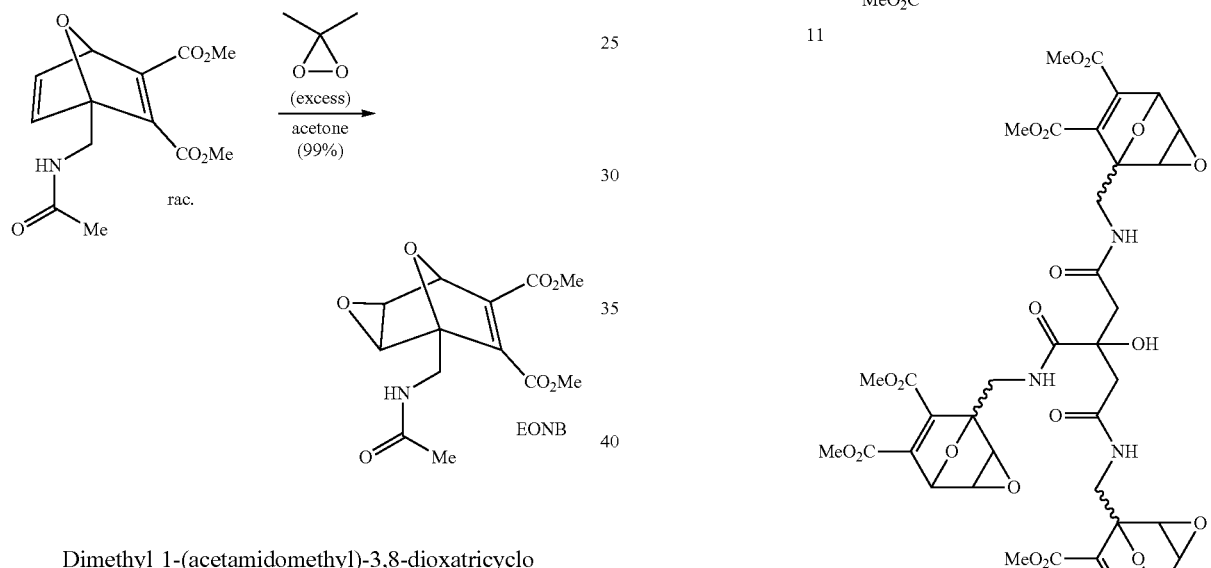

Dimethyl 1-(acetamidomethyl)-3,8-dioxatricyclo [3.2.1.0$^{2,4}$]oct-6-ene-6,7-dicarboxylate, EONB A vial was charged with previously described 1-dimethyl 1-(acetamidomethyl)-7-oxabicyclo[2.2.1]hepta-2,5-diene-2,3-dicarboxylate (21.5 mg, 0.076 mmols, 1 equiv), and dissolved in 1.5 mL ~0.07 M solution of DMDO (~1.1 equiv) in acetone at room temperature. The resulting solution was stirred at room temperature for 4 hours, and then condensed under reduced pressure to yield a white solid (22.7 mg, quantitative). R$_f$ 0.28 (EtOAc). $^1$H NMR (500 MHz, CDCl$_3$) δ 5.87 (s, 1H), 5.09 (s, 1H), 4.06 (dd, J=14.9, 6.3 Hz, 1H), 3.92 (dd, J=14.9, 5.3 Hz, 1H), 3.84 (s, 3H), 3.80 (s, 3H), 3.78 (d, J=3.6 Hz, 1H), 3.72 (d, J=3.6 Hz, 1H), 1.98 (s, 3H). $^{13}$C NMR (126 MHz, CDCl$_3$) δ 170.42, 163.13, 162.02, 149.95, 146.89, 91.35, 78.52, 77.48, 77.23, 76.98, 57.30, 56.55, 53.11, 52.89, 37.31, 23.17. FT-IR (cm$^{-1}$): 3375, 2956, 1717, 1660, 1537, 1435, 1239, 1132, 877. LC-HRMS: [C$_{13}$H$_{15}$NO$_7$+H$^+$] calc: 298.0921, obs: 298.0927. rt: 3.803 min (0-90% MeCN/H$_2$O).

Tetramethyl 1,1'-(((2-(2-(((6,7-bis(methoxycarbonyl)-3,8-dioxatricyclo [3.2.1.0$^{2,4}$] oct-6-en-1-yl) methyl)amino)-2-oxoethyl)-2-hydroxysuccinyl)bis (azanediyl))bis (methylene))bis(3',8'-dioxatricyclo [3.2.1.0$^{2,4}$]oct-6-ene-6,7-dicarboxylate), Epoxy-11

Tris-OND 11 (30.0 mg, 0.035 mmols, 1 equiv.) was dissolved in 1.95 mL of a ~0.07 M solution of DMDO (~3.9 equiv) in acetone and stirred at room temperature for 19 hours. The reaction mixture was faintly cloudy, and was filtered before condensing the filtrate under reduced pressure, and drying the residue on high vacuum to yield a pale foaming solid (30.5 mg, 96%). R$_f$ 0.53 (10% MeOH/ EtOAc). $^1$H NMR (500 MHz, CDCl$_3$) δ7.47-7.42 (m, 1H), 7.18-6.96 (m, 2H), 6.26-5.96 (m, 1H), 5.07-5.06 (m, 3H), 4.05-3.87 (m, 6H), 3.84-3.77 (m, 18H), 3.75-3.72 (m, 6H), 2.81-2.60 (m, 4H). $^{13}$C NMR (126 MHz, CDCl$_3$) δ 174.17, 174.16, 174.14, 174.12, 171.08, 171.02, 171.00, 170.97, 170.94, 163.14, 163.12, 162.18, 162.17, 162.16, 149.67, 149.63, 149.54, 149.52, 149.48, 149.40, 149.37, 147.51, 147.49, 147.47, 147.44, 147.33, 147.17, 147.14, 91.13, 91.09, 91.07, 91.05, 91.01, 90.98, 80.78, 78.56, 78.54, 75.10, 75.06, 75.05, 57.47, 57.36, 57.34, 56.67, 56.64, 56.60, 56.59, 55.21, 53.05, 52.84, 42.88, 42.76, 42.71, 42.62, 37.16, 37.11, 37.06, 37.02, 36.99, 36.97. FT-IR (cm$^{-1}$): 3369, 2955, 1716, 1668, 1530, 1238, 1132, 912, 875, 727. ESI-MS: [C$_{39}$H$_{41}$N$_3$O$_{22}$+H$^+$]=904.1.

III. Preparation of Gels

Figure 4:
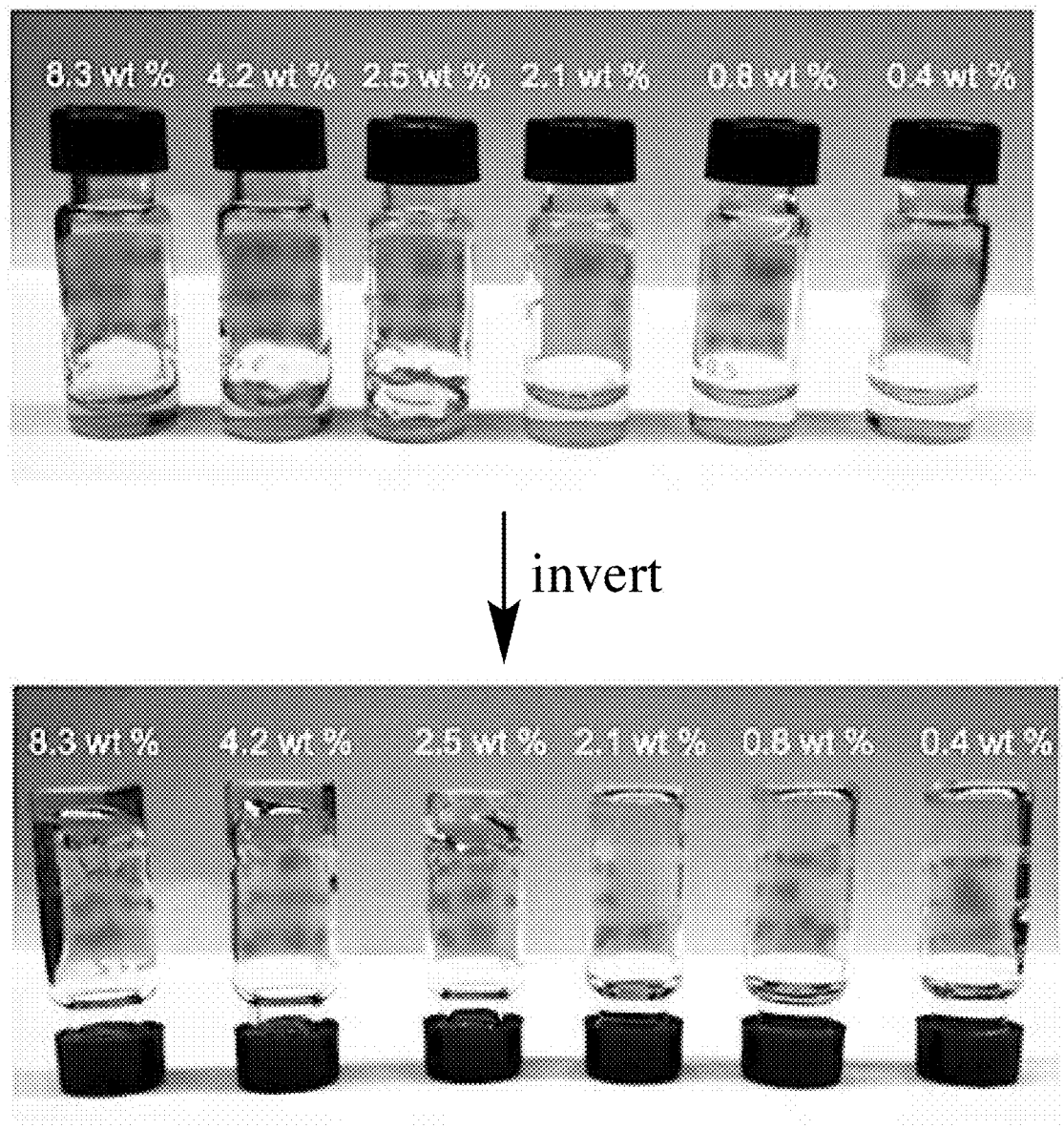
FIG. 4 depicts, on the left, upright samples 2 minutes after addition of triethylamine; on the right, shows the same samples after inversion. Samples at 0.4 2.1 wt % are free-flowing solutions.

Trial gelations were performed by premixing a solution of linker 7a with four-armed thiol-terminated poly(ethylene glycol) (4-PEG-SH. M$_n$=10,000) in neutral water containing 17% DMSO by volume. The overall concentration of PEG macromer was varied from 0.4 wt % to 8.3 wt % while maintaining an equimolar ratio of thiol to electrophile. Under these conditions, no gels formed on standing at room temperature for five minutes. Upon addition of stoichiometric triethylamine to the solution and mixing, instantaneous gelation was observed for solutions containing 4-PEG-SH at >2.5 wt % (FIG. 4).

Based on empirical observations made in these trials, subsequent gels were prepared at room temperature from 3.5 wt % 4-PEG-SH solutions in phosphate buffers containing 7% DMSO at equimolar concentrations of thiol and OND electrophile. Mixtures were mixed briefly with a vortex mixer, and the reaction vial was periodically tilted or inverted. Gelation time was recorded when the sample no longer flowed and was self-supporting. For linkers 7a, 7b, 10-12, gels were observed in less than 1.5 minutes at pH 7.2, and approximately 30-45 seconds at pH 7.4. Gels formed with linker 7c did not form self-supporting gels at pH 7.4, but formed gels at pH 8.0, as described in the summary above. Gelation time at 37° C. was determined by pre-warming 4-PEG-SH macromer and OND stock solutions in a 37° C. water bath. Gel components were combined and mixed briefly by pipetting, and the sample was held in the water bath. Gelation time was determined by the inversion test, as described above.

IV. Oscillatory Rheology

Oscillatory rheology was used to assess the viscoelastic properties of selected PEG-OND hydrogels. 4-PEG-SH macromer and bis-EONB 8 were combined in a 1:1 thiol: electrophile ratio (1:2 molar ratio) in 100 mM pH 7.2 potassium phosphate buffer containing 7% (v/v) DMSO. The solution was briefly mixed by pipetting and immediately deposited on the center of the rheometer bottom plate, which was maintained at 37° C. The truncated cone was then brought in contact with the bis-EONB/4-PEG-SH mixture before setting of the gel by positioning the tool at the measuring position. The sample was inspected for spillovers and trimmed as required. A preliminary preshearing step consisting of 30 seconds at 0.1% strain and ω=0.01 rad/s was performed to ensure good contact with the gel sample. The elastic (storage) and viscous (loss) moduli, G' and G", respectively, were then measured as a function of time for a constant strain of 1% and an angular frequency of 1 rad/sec. The ability to store energy is described by G', while the amount of energy dissipated is related with G". It was observed that the sample experienced a rapid transformation from an initial state in which G' was not much larger than G" to a state in which G' was clearly predominant, as shown in FIG. 5; this is consistent with gelation. The observed transformation happened in the first few minutes after preparation, even when the hydrogel continued to rigidify for up to 2-3 hours. At this point, the system reached an essentially time-independent state where G" was negligible in comparison with G', indicative of the solid-like nature of the material.

The linear regime of this sample was determined by performing an oscillatory strain sweep at 37° C. We found the response to be linear in a wide range of strains, as shown in Fig. S3. Note that G'>>G", consistent with the time dependence results shown in Fig. S2. The frequency sweep shown in the main text was thus performed in the linear region.

Figure 8:
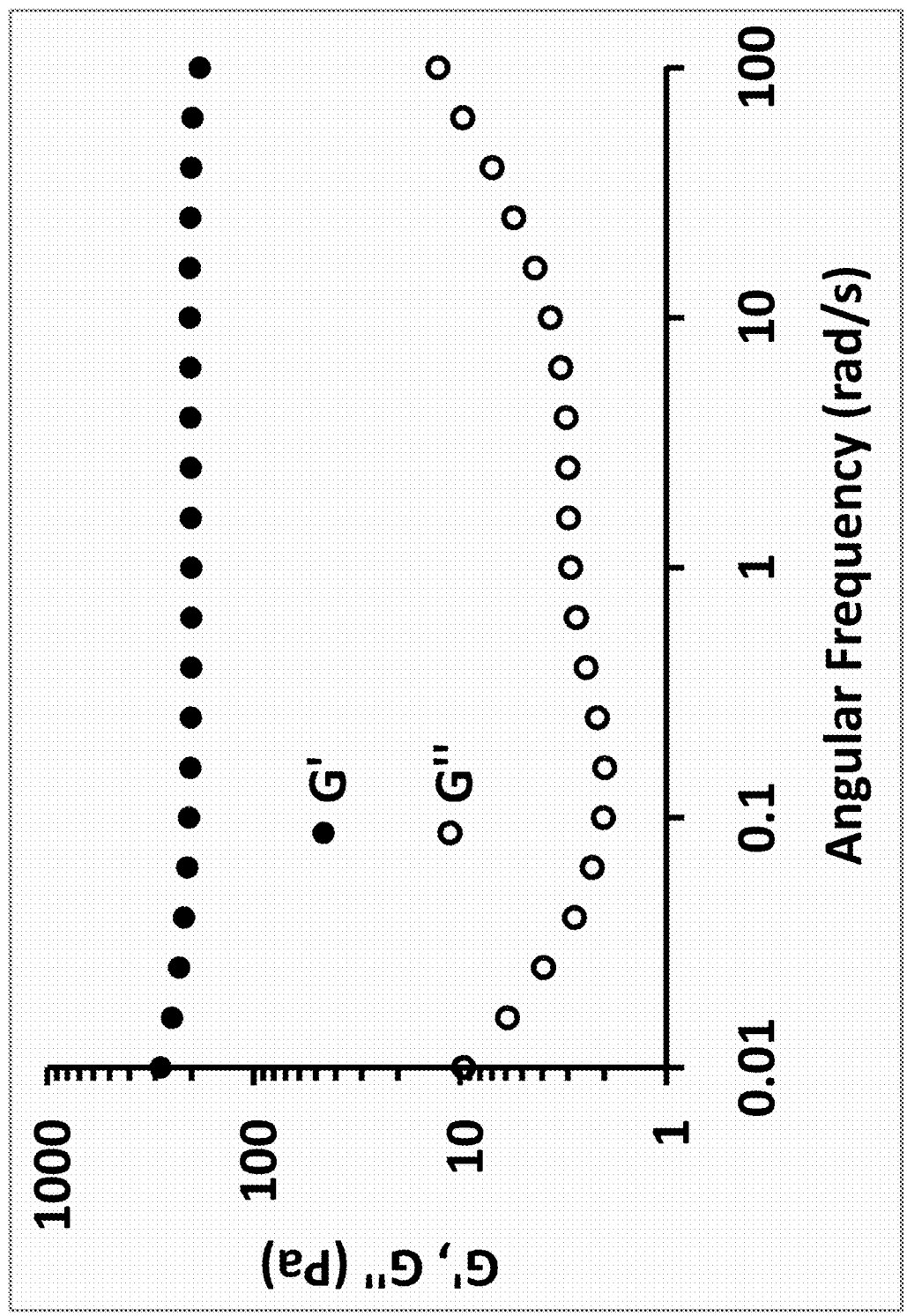
FIG. 8 depicts frequency sweep for the gel derived from bis-OND 7c and 4-PEG-SH macromer (1:1 thiol:OND) at 4° C. and γ=5%.

The viscoelasticity of the hydrogel derived from 4-PEG-SH macromer and bis-OND linker 7c, at pH 8.0 and T=4° C. has also been characterized, by performing oscillatory strain and frequency sweeps. It was found that the response is linear in a wide range of strains, as shown in Fig. S4. Similarly, G' is essentially frequency independent, as shown in FIG. 8. In both experiments, G'>>G". These results confirm the solid-like nature of this sample in these conditions.

V. Monitoring Degradation of Neat Hydrogels

V.1. Assessment of Gel Integrity by the Inversion Test

Figure 9:
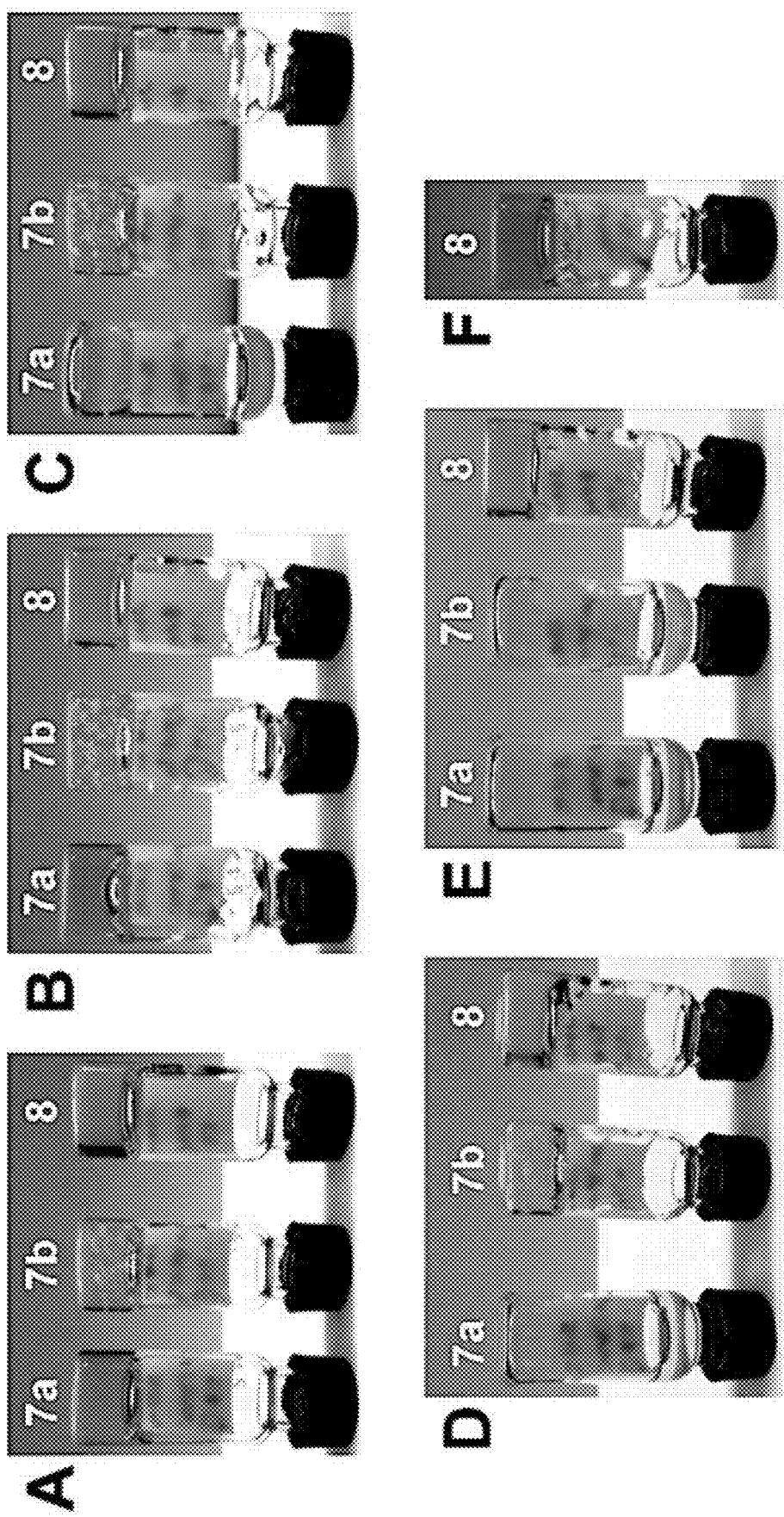
FIG. 9 depicts monitoring hydrogel degradation by inversion test. Incubation performed at 50° C. for (A) 0 hours, (B) 2 hours, (C) 3 hours, (D) 8.5 hours, (E) 20.5 hours, (F) 5 days.

Three 500 μL 3.5 wt % hydrogels were formed with bis-ONDs 7a and 7b, and bis-EONB 8, respectively, in 2 mL vials with caps. The sealed vials were incubated in an oil bath maintained at 50° C. The samples were periodically removed from heat and the vials were inverted to determine if the gel was still intact, or whether the sample was a free-flowing liquid, as described in the main text. A full time course of the experiment presented in FIG. 1 of the main text is shown in FIG. 9 below. The gel formed between 4-PEG-SH and bis-EONB 8 in FIG. 9 was removed from heat after 5 days, and stored at room temperature in a sealed vial. The hydrogel is still intact at the time of writing (5 days at 50° C. followed by >1 year at room temperature). The inversion test was routinely used in all stability experiments to verify hydrogel integrity during incubation.

V.2. Time-Lapse Photography

In order to observe reverse gelation upon prolonged heating of neat hydrogels, time-lapse photography was carried out. Briefly, 600 μL hydrogels comprised of 3.5 wt % 4-PEG-SH+bis-OND/EONB (7a, 7b, and 8, respectively) in pH 7.4 100 mM potassium phosphate buffer containing 7% DMSO (v/v) were formed in glass culture tubes and allowed to set for 15 minutes. A glass bead (~160 mg, stained with blue Sharpie-brand marker to improve visibility) was placed carefully on top of each gel, and a drop of silicon oil was added to prevent evaporation at the surface of the gels. The tubes were sealed with lab parafilm and incubated in a 50° C. oil bath. Photos were collected every 2 minutes for ~22 hours using Chronolapse software (v.1.0.4) and a Creative Labs webcam. Photographs were compiled in chronological order using iMovie software, with each photo occupying one 0.1 s frame. The resulting video is available as S1 Video, mentioned above.

VI. NMR Analysis of Hydrogels

In standard 5 mm NMR tubes, a 500 μL 3.5 wt % PEG-OND hydrogel were prepared by mixing 465 μL of 3.76 wt % 4-PEG-SH in pH 7.4 KDPO$_4$/K$_2$PO$_4$ buffer and 35 μL 85 mM 7a in DMSO-d$_6$ and vortexing to mix. $^1$H-NMR spectra were collected on the sample 10 minutes after mixing. Samples were then incubated at 37° C. and $^1$H-NMR were collected periodically. Additionally, spectra were collected as close as possible to the reverse gelation point to determine fractional conversion of OND-thiol adduct to furan. The sample was monitored until complete conversion of thiol adducts to furan was observed (FIG. 10, blue highlighted peaks to green highlighted peaks).

Figure 11:
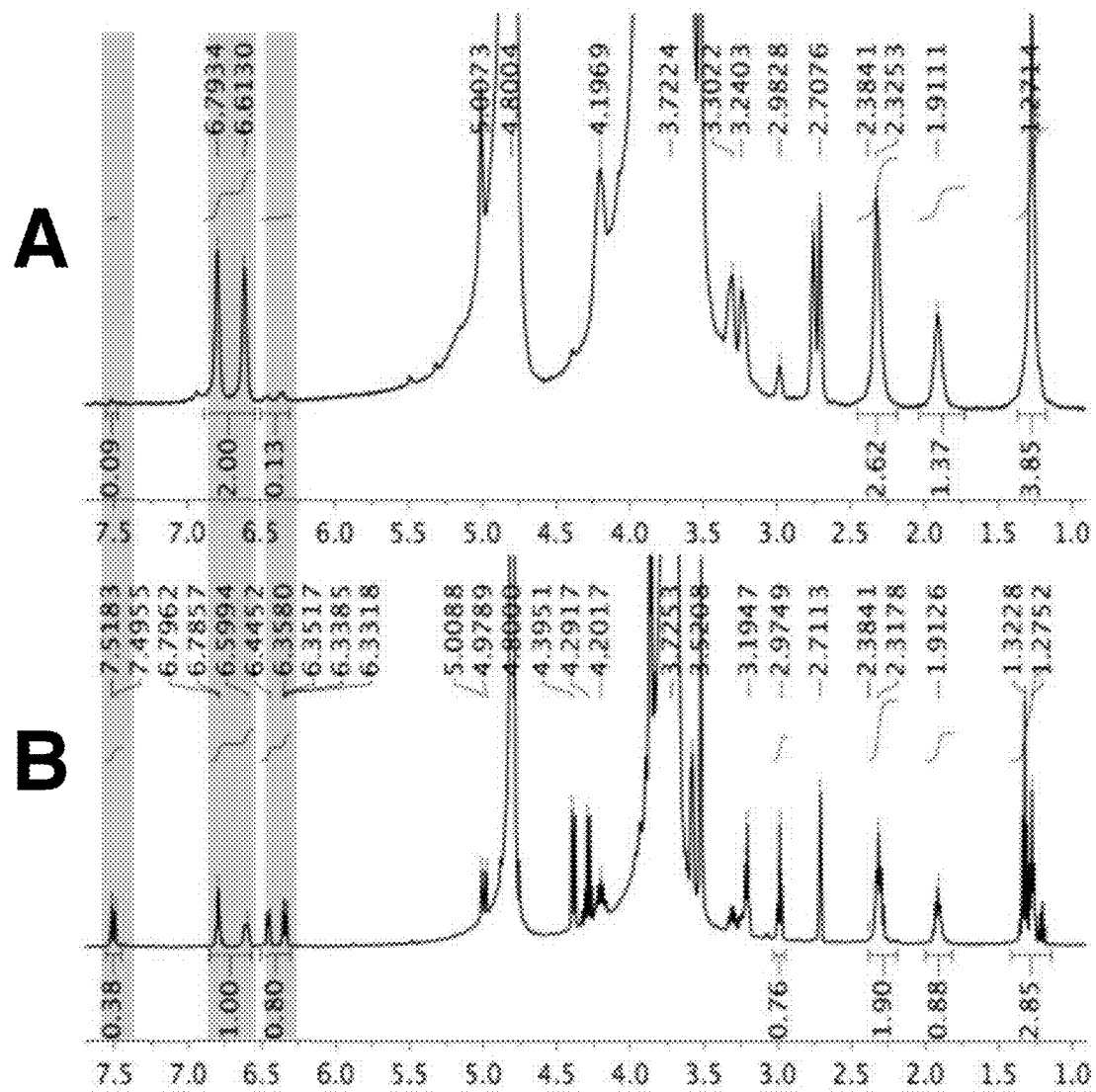
FIG. 11 depicts $^1$H NMR spectra of PEG-OND Hydrogel formed with 4-PEG-SH macromer and bis-ONDs 7b. (A) PEG-OND hydrogel from 4-PEG-SH and 7a, 15 mins after mixing at 22° C., (B) Sample at reverse-gelation point. Second highlighted vertical band=distinctive OND-thiol adduct peaks, first and third highlighted vertical band=distinctive furan peaks.

A 3.5 wt % hydrogel formed with linker 7b was prepared in a similar fashion. The sample was a self-supporting gel when the tube was inverted 1 minute after mixing. A $^1$H NMR spectrum was collected ~15 minutes after mixing the sample. All OND linker was converted to the corresponding thiol adduct. The sample was then placed in a 37° C. incubator and spectra were collected periodically until the gel was no longer intact, as determined by the inversion test (FIG. 11).

Figure 12:
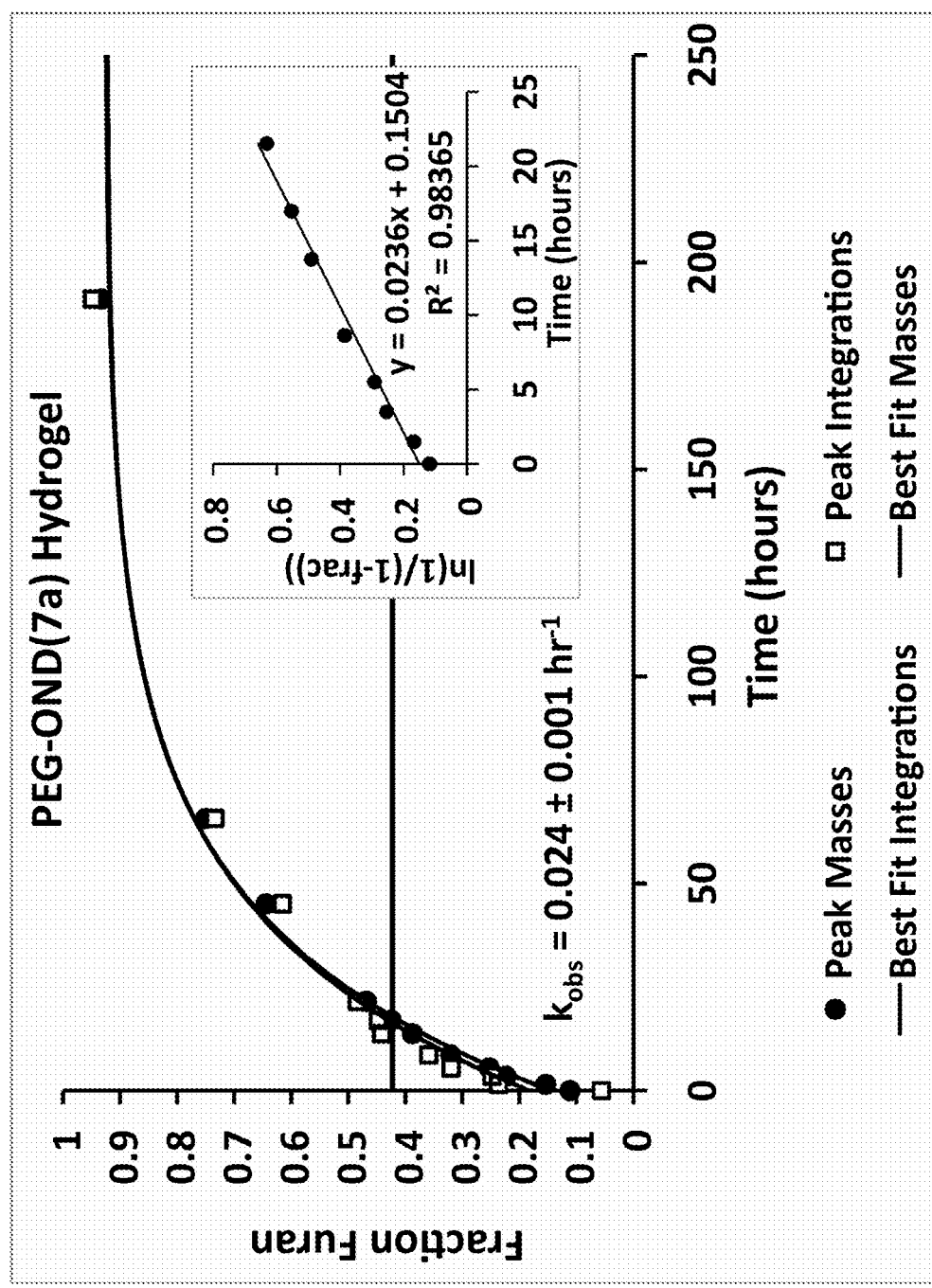
FIG. 12 depicts observed conversion of OND-thiol adducts to furan vs. time in a 3.5 wt % PEG-OND hydrogel formed with bis-OND 7a. The horizontal dotted line represents the theoretical reverse gelation point.
Figure 13:
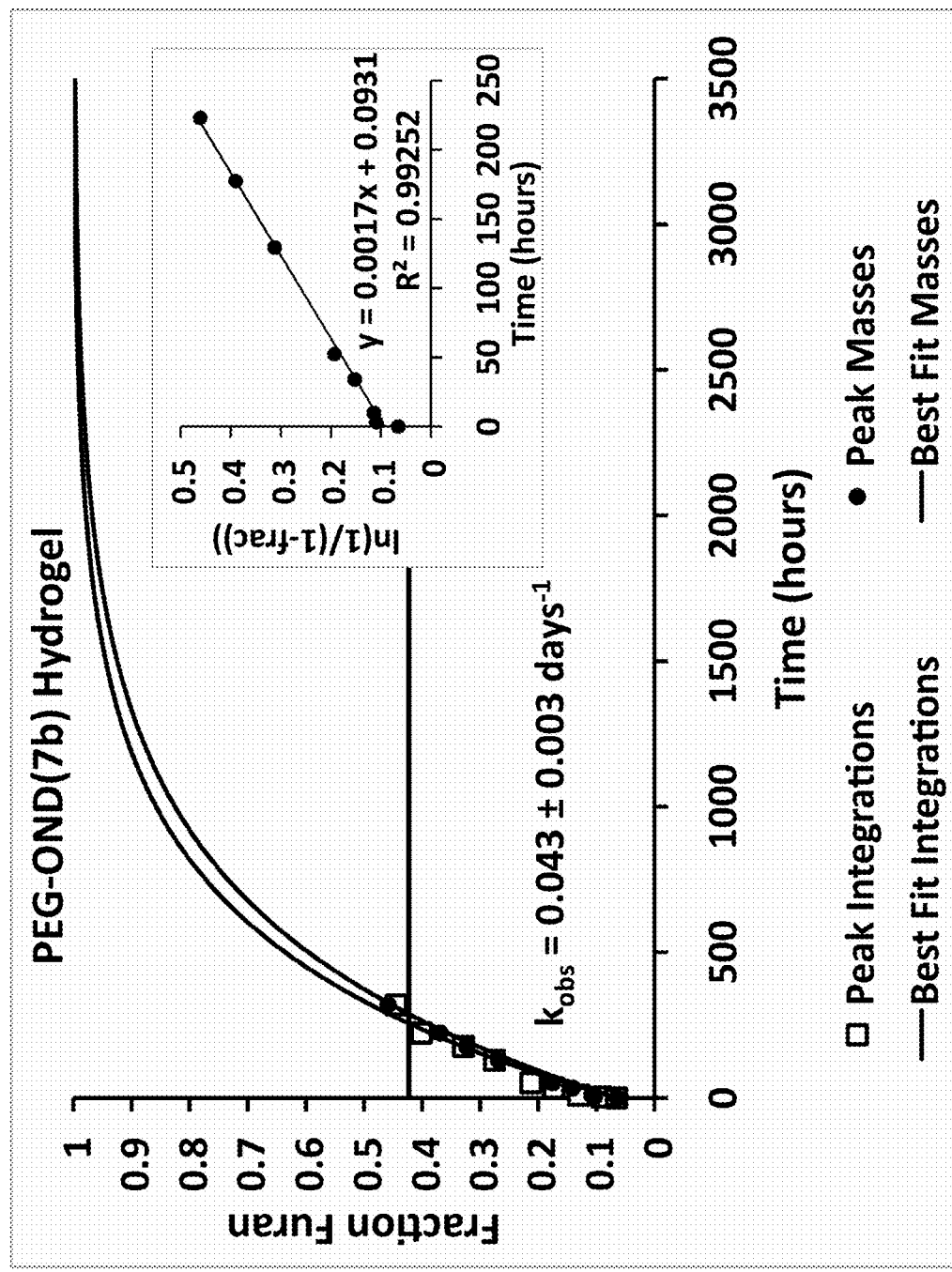
FIG. 13 depicts observed conversion of OND-thiol adducts to furan vs. time in a 3.5 wt % PEG-OND hydrogel formed with bis-OND 7b. The horizontal dotted line represents the theoretical reverse gelation point.

The degree of conversion of the OND-thiol adducts to furan when sample no longer contained a self-supporting gel was close to the theoretical reverse gelation point for gels formed by step-growth polymerization between tetravalent and divalent components (See section VII.3. for details). To estimate the rate constant for retro-Diels-Alder fragmentation of OND-thiol adducts in the neat hydrogels, the degree of conversion of adduct to furan was determined from integration of the C5 and C6 olefinic protons of thiol adducts (blue highlight, FIGS. 10 and 11) and the integrals of furan protons (green highlights). For comparison, the same peaks were carefully cut out of printed versions of spectra and weighed. The ratio of the mass of furan peaks to the mass of furan and C5+C6 peaks at each time point provided fractional conversion values similar to those obtained by integration. The degree of conversion was plotted against time and least-squares non-linear curve fitting to the first order integrated rate law was performed using the Solver plug-in in Microsoft Excel (FIGS. 12 and 13). Plotting ln(1/1-fraction furan) vs. time yielded linear plots, with slopes providing a rate constant comparable to those obtained in non-linear fitting (FIGS. 12 and 13).

VII. Equilibrium Swelling and Determination of Gel Fraction

VII.1. Equilibrium Mass Swelling Ratio Determination

200 μL gels were prepared in pH 7.4 100 mM phosphate buffered saline containing 7% DMSO with 3.5 wt % 4-PEG-SH and the corresponding bis-, tris-, and tetra-ONDs to provide a 1:1 thiol to electrophile ratio, and allowed to cure for 20 minutes at room temperature. The mass of the gels after curing was recorded ($M_{eq}$) before suspending in 5.5 mL of water. The hydrogels were stored at 4° C. during swelling to prevent significant degradation of the network during the experiment. The increase in mass of the gels was monitored periodically by decanting and blotting the gel gently with a kimwipe to remove excess water before weighing. After 24 hours swelling, when swelling had stabilized, the mass of the gel was recorded ($M_{eq}$). The equilibrium mass swelling ratio was then determined using the following relationship:

$$\text{Equilibrium Mass Swelling Ratio} = \frac{M_{eq}}{M_0} \quad \text{(Equation S1)}$$

VII.2. Gel Fraction Determination

After weighing equilibrium-swelled gels to determine equilibrium mass swelling ratio, the gels were freeze-dried and the residual mass was weighed ($M_{res}$). It is expected that buffer salts present in the sample when it was formed were removed by the multiple changes of swelling solvent (pure water). The mass of the remaining residue was compared to the input mass ($M_{in}$) of 4-PEG-SH macromer and OND-based linker. The ratio of the residual mass and the input mass provides the fraction of material by mass incorporated into the hydrogel network (gel fraction), as shown in the following equation:

$$\text{Gel Fraction} = \frac{M_{res}}{M_{in}} \quad \text{(Equation S2)}$$

VII.3. Calculations with Flory-Rehner Elastic Theory

Critical Gelation/Reverse Gelation Point:

During the formation of a homogeneously crosslinked hydrogel network, discrete soluble polymer segments (i.e. macromer monomers or oligomers) become linked as non-elastic chain ends are chemically stitched together or become physically entangled. This process continues until the critical gelation point is reached, at which point the polymer segments are now part of a macroscopic network. The degradation of a hydrogel formed using labile linkers can be described loosely as the reverse of gel formation. Linkages holding polymer segments together break down, revealing non-elastic chain ends until a critical point at which the gel rapidly disintegrates/dissolves into finite polymer segments. This phase is characterized by a steep "burst" phase of release in the erosion of the hydrogel (see FIG. 2). The critical gelation/reverse-gelation point for an ideal network formed by step-growth polymerization between two orthogonally reactive monomers of valence $f_A$ and $f_B$ can be described by adapting the theory first described by Flory and Rehner:

$$P_c^{step\text{-}growth} = \frac{[A-B\ \text{linkage}]_L}{[A-B\ \text{linkage}]_O} = \frac{1}{\sqrt{r(f_A-1)(f_B-1)}} \quad \text{(Equation S3)}$$

where $P_c^{step\text{-}growth}$ is the fraction of crosslinks between monomers A and B at the critical gelation point (or reverse gelation point), $f_A$ is the valence of monomer A, $f_B$ is the valence of monomer B, and r is the stoichiometric ratio of reactive groups A and B. The value of $P_c^{step\text{-}growth}$ for a network formed from an equimolar mixture of 4-armed PEG-SH ($f_A$=4) and divalent OND (or EONB) linkers ($f_B$) is:

$$P_c^{step\text{-}growth} = \frac{1}{\sqrt{1(4-1)(2-1)}} = \frac{1}{\sqrt{3}} \sim 0.5774 \quad \text{(Calculation S1)}$$

The degree of conversion of OND-Thiol adducts to furan and thiomaleate/thiofumarate in a formed PEG-OND gel network to reach the critical reverse gelation point is 1−$P_c$=0.4226. Applying Equation S3, the critical reverse gelation point can be calculated for networks formed between 4-PEG-SH and ONDs of higher valence:

Trivalent OND: (Calculation S2)

$$P_c^{step\text{-}growth} = \frac{1}{\sqrt{1(4-1)(3-1)}} = \frac{1}{\sqrt{6}} \sim 0.4082$$

Tetravalent OND: (Calculation S3)

$$P_c^{step\text{-}growth} = \frac{1}{\sqrt{1(4-1)(4-1)}} = \frac{1}{3} \sim 0.3333$$

Calculation of Theoretical Molecular Weight Between Crosslinks

Using the masses measured during equilibrium swelling experiments, it is possible to estimate the apparent average molecular weight between crosslinks ($M_c$) present in the hydrogel. For an ideally crosslinked network, this value is determined by the molecular weight and valence of the monomeric/macromeric components, as previously described by Metters and Hubbell:

$$M_{C,Initial,Ideal} = 2\left(\frac{MW_A}{f_A} + \frac{MW_B}{f_B}\right) \quad \text{(Equation S4)}$$

Since the 4-PEG-SH macromer average molecular weight and valence is kept constant, the $M_{c,ideal}$ varies only with the molecular weight and valence of the OND linker used to form the network. However, this formula neglects the formation of physical entanglements or crosslinks, and only accounts for elastically-productive chemical crosslinks. Applying Equation S3, the $M_{c,ideal}$ values for bis-, tris-, and tetra-ONDs/EONBs used in this study are summarized in Table S1.

TABLE S1

Summarized linker molecular weights, valence, and calculated $M_{c, ideal}$.

| Entry | Linker | $MW_B$ (g/mol) | Valence, $f_B$ | $M_{c,\ ideal}$ (g/mol) |
|---|---|---|---|---|
| 1 | 7a | 574.5 | 2 | 5,575 |
| 2 | 7b | 622.5 | 2 | 5,623 |
| 3 | 8 | 606.5 | 2 | 5,607 |
| 4 | 10 | 598.5 | 2 | 5,599 |
| 5 | 7a + 7b | 598.5[a] | 2 | 5,599 |
| 6 | 11 | 855.8 | 3 | 2,785 |
| 7 | 12 | 1,309.2 | 4 | 2,827 |

[a] Average molecular weight for a equimolar mixture of linkers 7a and 7b.

Experimental Determination of Molecular Weight Between Crosslinks by Equilibrium Swelling The apparent molecular weight between elastically-productive crosslinks ($M_c$) was determined from equilibrium swelling data, collected as described in section VII.1 and applying a modified form of the Flory-Rehner equation for networks formed under dilute conditions:

$$M_c = \left[\frac{2}{M_n} - \frac{\frac{\bar{v}}{V_1}[\ln(1 - v_{2,s}) + (v_{2,s}) + (\chi(v_{2,s})^2)]}{(v_{2,r})\left[\left(\frac{v_{2,s}}{v_{2,r}}\right)^{1/3} - \frac{v_{2,s}}{2v_{2,r}}\right]}\right]^{-1} \quad \text{(Equation S5)}$$

where $M_n$ is the number average molecular weight for the polymeric macromer (10,000 g/mol), $\bar{v}$ is the specific volume of the polymer (0.84 cm³/g for PEG) $V_1$ is the molar volume of solvent used for swelling (18 cm³/g for water), $\chi$ is the polymer-interaction parameter (0.43 for PEG-$H_2O$ and assumed constant for the described experiments). $V_2$, and $V_2$, are the volume fraction of polymer in the equilibrium swollen gel and the relaxed gel after curing, respectively, and are calculated as follows:

$$v_{2,s} = \left[1 + \frac{(q_w - 1)\rho_P}{\rho_{water}}\right]^{-1} \quad \text{(Equation S6)}$$

$$v_{2,s} = \left[1 + \frac{(q_F - 1)\rho_P}{\rho_{cure\ solvent}}\right]^{-1} \quad \text{(Equation S7)}$$

where $q_w$ is the weight swelling ratio after equilibrium swelling, $q_F$ is the weight swelling ratio after curing, $\rho_p$ is the density of the polymer (1.12 g/cm³ for PEG), $\rho_{water} = \rho_{cure\ solvent}$ is the density of swelling solvent and solvent during gel formation (1.00 g/cm³ for water). The weight swelling ratios $q_w$ and $q_F$ are determined from data gathered in equilibrium swelling experiments using the following relationships:

$$q_w = \frac{m_s}{m_d} \quad \text{(Equation S8)}$$

$$q_F = \frac{m_c}{m_d} \quad \text{(Equation S9)}$$

where $m_s$ is the mass of the gel after equilibrium swelling, $m_c$ is the mass of the gel after curing, and $m_d$ is the mass of the dried gel, or input mass of polymer and crosslinkers.

Using the formulae above, masses of hydrogel samples recorded after equilibrium swelling, curing, and drying were applied to estimate the apparent molecular weight between crosslinks, which are summarized in Table 1 of the main text. The experimentally observed $M_c$ values for gels formed using divalent OND linkers was lower than theoretical ideal value $M_{c,ideal}$. This can be explained by the fact that the $M_{c,ideal}$ values calculated for these gels (entries 1-5 of Table S1) are greater than the entanglement molecular weight for polyethylene glycol (~4,400 g/mol). The experimentally observed $M_c$ values are a combination of chemical and physical crosslinks, while the calculation of $M_{c,ideal}$ only accounts for chemical crosslinks in the network. The experimentally observed $M_c$ values for networks formed with tris- and tetra-OND linkers are greater than the theoretical value $M_{c,ideal}$, but are still a product of both chemical and physical crosslinks.

Calculation of Hydrogel Mesh Size

Using the calculated molecular weight between crosslinks, $M_c$, and the method previously described by Canal and Peppas, the hydrogel mesh size was calculated. First, the root-mean-square end-to-end distance of the polymer chains in the network, $(\bar{r}_0^2)^{1/2}$, was calculated as follows:

$$(\bar{r}_0^2)^{1/2} = lC_n^{1/2}n^{1/2} \quad \text{(Equation S10)}$$

where l is the average bond length in the polymer (0.146 nm for PEG) and $C_n$ is the characteristic ratio of the polymer (4.0 for PEG). The average number of bonds between crosslinks, n is calculated using the following equation:

$$n = 2\frac{M_c}{M_r} \quad \text{(Equation S11)}$$

where $M_c$ is the average molecular weight between crosslinks, calculated as described in the previous section, and $M_r$ is the molecular weight of the repeating unit for the PEG macromer (44 g/mol). Finally, the mesh size, $\xi$, is calculated using the following relationship:

$$\xi = v_{2,s}^{-1/3}(\bar{r}_0^2)^{1/2} \quad \text{(Equation S12)}$$

where $v_2$, is the partial volume of polymer in the equilibrium swollen hydrogel, and is calculated using the experimentally determined equilibrium weight swelling ratios. The calculated mesh sizes for the hydrogels studied by equilibrium swelling are shown in Table S2.

TABLE S2

Calculated mesh size for various equilibrium-swollen gels.

| Entry | Linker | (nm)[a] |
|---|---|---|
| 1 | 7a | 15.2 ± 0.9 |
| 2 | 7b | 13.1 ± 0.1 |
| 3 | 8 | 14.0 ± 0.9 |
| 4 | 10 | 15.1 ± 1.3 |
| 5 | 7a + 7b | 14.4 ± 0.5 |
| 6 | 11 | 13.7 ± 1.3 |
| 7 | 12 | 13.3 ± 0.9 |

[a] Calculated using Equations S9-S11 using equilibrium swelling data.

VIII. Post-Functionalization and Determination of Residual Hydrogel Thiol Content The thiol content of cured hydrogels was determined by swelling gels in the presence of a small fluorogenic OND S-6, which we have previously described in our lab.

Figure 14:
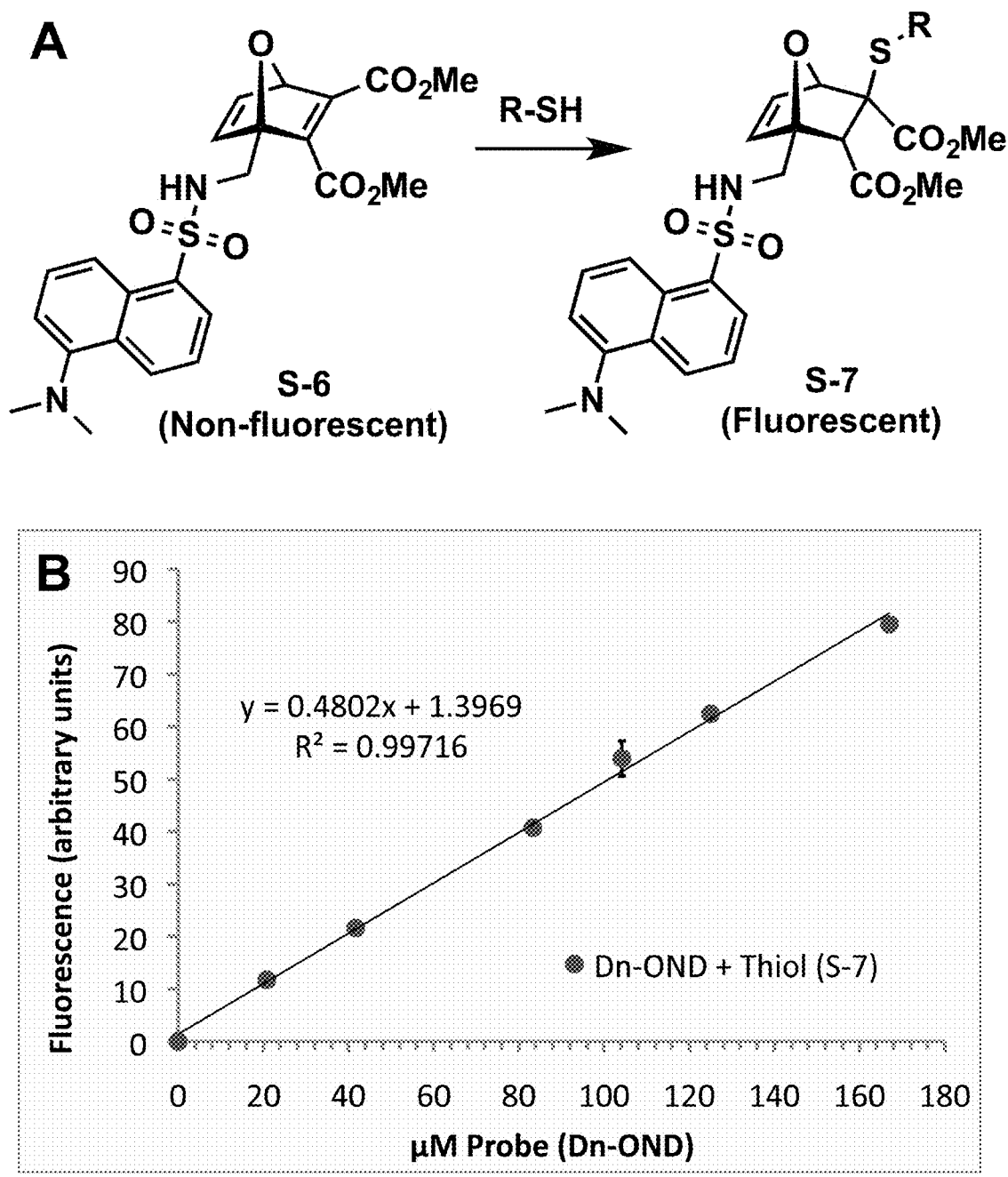
FIG. 14 depicts quantitation of fluorogenic OND-thiol adduct concentration as a means of determining thiol concentration. (A) Fluorogenic OND S-6 reacts with thiols to yield a fluorescent product. (B) A linear correlation with thiol adduct concentration and measured fluorescence is observed.

This probe reacts with thiols to produce a fluorescent adduct (FIG. 14A). The intensity of fluorescence correlates linearly with the concentration of adduct S-7; this was demonstrated by incubation increasing concentrations of S-6 with a large excess of N-acetyl cysteine to produce the standard curve shown in FIG. 14B. Thus, the concentration of reagent S-6 in solution can be determined by quenching with thiol. Similarly, reagent S-6 can be used to quantify thiol in solution.

Based on cargo diffusion studies (see section X of this document), we expected that probe S-6 should easily permeate the hydrogel network under swelling conditions and react with accessible residual thiols present in the gel network. In order to test this hypothesis, 60 µL hydrogels were freshly prepared from 4-PEG-SH macromer and either linkers 8 or 7a as described in section III of this document. After curing for 20 minutes at room temperature, 3 mL of pH 7.4 0.1M PBS buffer containing 200 µM probe S-6 was added, and the gel was swelled at 4° C. for 18 hours. To account for hydrolytic degradation of our thiol probe during incubation, a sample was prepared with S-6 in buffer alone (lacking 4-PEG-SH and bis-OND linkers). After swelling, the gels were observed under long-wave ultraviolet light to reveal strongly fluorescent gels and weakly fluorescent supernatants (FIG. 15). The control revealed that a small amount of fluorescence was present after incubation in the absence of thiol due to hydrolytic degradation of the linker. Presumably the fluorescence in the supernatant of samples containing gels is due to soluble fraction of 4-PEG-SH macromer and oligomers not incorporated into the gel network.

In order to calculate the amount of residual thiol present in the soluble fraction, aliquots of the supernatant were removed and fluorescence was measured. Thiol content of the soluble fraction was determined by interpolation using the standard curve shown in FIG. 14 after accounting for fluorescence due to hydrolytic degradation. The concentration of thiol present in the supernatant was found to be 2.1±0.4% and 8.1±3.2% of the input thiol for the gels prepared from linker 8 and 7a respectively. This amount corresponds well with the soluble fraction (soluble fraction=1−gel fraction) determined from swelling experiments (see Table 1 of main text). To determine residual thiol content present in gels, aliquots of the supernatant were quenched with a large excess (10 mM) of N-acetyl cysteine and the increase in fluorescence was measured to determine the amount of unreacted S-6 remaining in the supernatant. Accounting for the amount of probe already consumed by reaction with soluble fraction thiols and by hydrolytic degradation, the amount of residual thiol accessible for post-modification present in the gel was calculated as 13.4±1.4% and 10.8±2.4% of the initial thiol content of input macromer (average of 11.8±3.3 for both sets of gels prepared from linkers 7a and 8).

These results demonstrate the presence of network defects, and depicted in FIG. 42 of the main text, and demonstrates that thiols are accessible in these networks for post-functionalization purposes. This feature may be useful in potential applications such as 3-D tissue culture.

TABLE S3

Residual Thiol Content of Swelled Hydrogels

| Linker | Sol Fraction % Residual Thiol | Gel Fraction % Residual Thiol |
|---|---|---|
| 7a | 8.1 ± 3.2 | 10.8 ± 2.4 |
| 8 | 2.1 ± 0.4 | 12.8 ± 2.2 |

IX. Monitoring Erosion of Swollen Hydrogels

IX.1. Dye labeling of 4-PEG-SH (10K)

14.8 mg 4-PEG-SH macromer (5.032 µmol thiol) was weighed into a tared vial in a glove box under inert atmosphere (<10 ppm $O_2$) and dissolved in 191 µL dry acetonitrile. Less than 1 µL of $Et_3N$ was added followed by dropwise addition of 202 µL 0.74 mM BODIPY-FL maleimide (0.151 µmol, 3% of thiol content) in acetonitrile over 10 minutes. The resulting neon-green solution was stirred at room temperature wrapped in foil for 2 hours, and then condensed under vacuum to dryness. This residue was redissolved at 3.76 wt % PEG in pH 7.2 100 mM phosphate buffered saline for use in hydrogel formation.

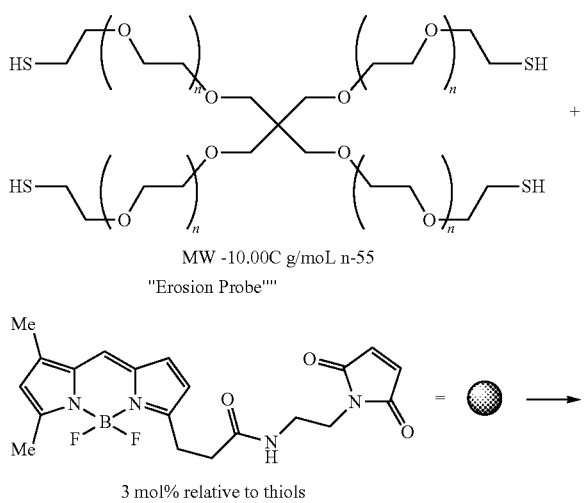

Scheme S3. Labeling of 4-PEG-SH macromer with BODIPY-FL maleimide erosion probe.

-continued
Probe-labeled 4-PEG-SH

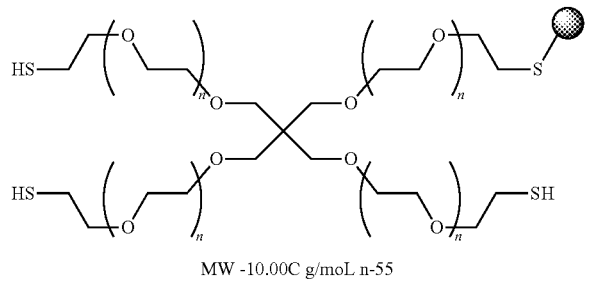

MW ~10.00C g/moL n-55

Figure 16:
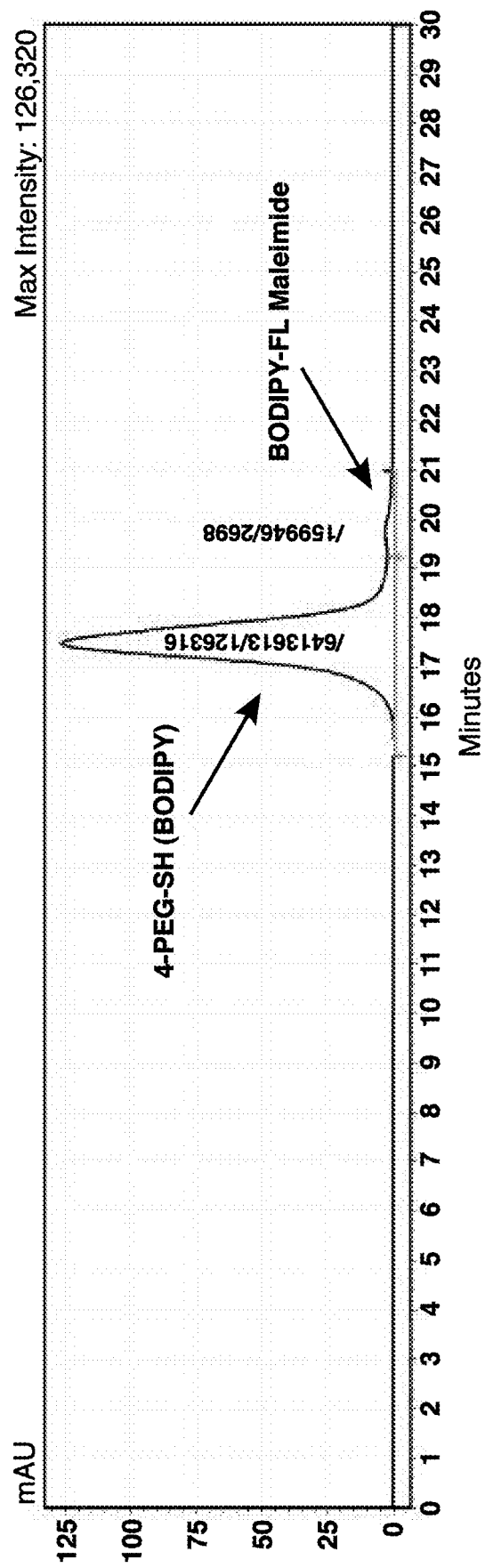
FIG. 16 depicts GPC analysis of BODIPY FL maleimide-labeled 4-PEG-SH macromer.

Conjugation of the erosion probe to the 4-PEG-SH macromer was verified by gel permeation chromatography (GPC) analysis with refractive index detector and diode array detector at 504 nm (FIG. 16).

Labeling reactions in which a solution of 4-PEG-SH in acetonitrile was added to BODIPY FL maleimide at 25 mM in DMSO were also performed. While complete consumption of BODIPY FL maleimide was observed in these reactions by GPC analysis, this protocol led to poorly controlled labeling, resulting in a large fraction of multiply-labeled 4-PEG-SH macromer. This material yielded gels that release a large fraction of dye within the first 24 hours, and release of up to 50% of dye from non-degradable gels formed with linker 8 and upon storage of degradable gels at 4° C. (in the absence of gel degradation). Controlled addition of the erosion probe to a solution containing a large excess of thiol is necessary in order to obtain clean labeling of the macromer. Finally, attempted labeling reactions in methanol in the presence of catalytic sodium methoxide resulted in poor conversions, most likely due to methanolysis of the maleimide reactive group during the course of the reaction.

IX.2. Monitoring Erosion of Hydrogels

The 3.76 wt % solution of BODIPY-labeled 4-PEG-SH prepared above was used to form hydrogels using a method identical to unlabeled gels. Briefly, BODIPY-labeled 4-PEG-SH was combined with DMSO stocks of multivalent ONDs at equimolar concentration of thiol and electrophile. All reactions yielded self-supporting gels within one minute after mixing the two components at room temperature. These gelations were carried out in an oxygen-free environment and gels were allowed to set for 20 minutes at room temperature before dilution with 3 mL of swelling buffer (variable composition, as described in main text). The absorbance of the supernatant at 504 nm was measured immediately to obtain a baseline measurement (t=0 hours), and the samples were placed into a 37° C. incubator. The absorbance of the swelling supernatant was monitored periodically by removal of 1 mL of buffer into a cuvette and measuring absorbance of the sample at 504 nm. The supernatant was then returned to the gel sample at 37° C. This process was repeated for each sample until gel degradation was complete and the absorbance at 504 nm stabilized (100% dye released). In order to estimate the fraction of dye released from the non-degradable gel formed with bi s-EONB 8, a mock endpoint sample consisting of BODIPY-labeled 4-PEG-SH diluted to 3.5 wt % was prepared, and the absorbance at 504 nm was measured. This value was taken as the 100% dye released point. The absorbance values collected over the course of the experiment were divided by the absorbance value measured after gel disintegration to obtain fractional dye release versus time. Each erosion experiment was run with duplicate gel samples for each condition tested, and the experiment was repeated (duplicate of duplicates).

IX.3. GPC Analysis of Supernatants

Additional gel samples formed with linker 7b were prepared for the purpose of analyzing the contents of the supernatant during erosion. These samples were swelled in Milli-Q ultrapure water and incubated at 37° C. At various time points during the erosion experiment, the supernatant was removed and dried in vacuum. The residue was taken up in DMF containing 0.1% LiBr and analyzed by gel permeation chromatography. Combinations of monomeric and oligomeric species of PEG macromer were observed. To compare composition of supernatant contents at different stages of erosion, the supernatant was removed and replaced by fresh swelling supernatant. After the desired degree of erosion, this supernatant was also collected for analysis. These supernatant "snapshots" were compared to a sample that did not undergo supernatant changes during erosion (FIG. 17).

Figure 18:
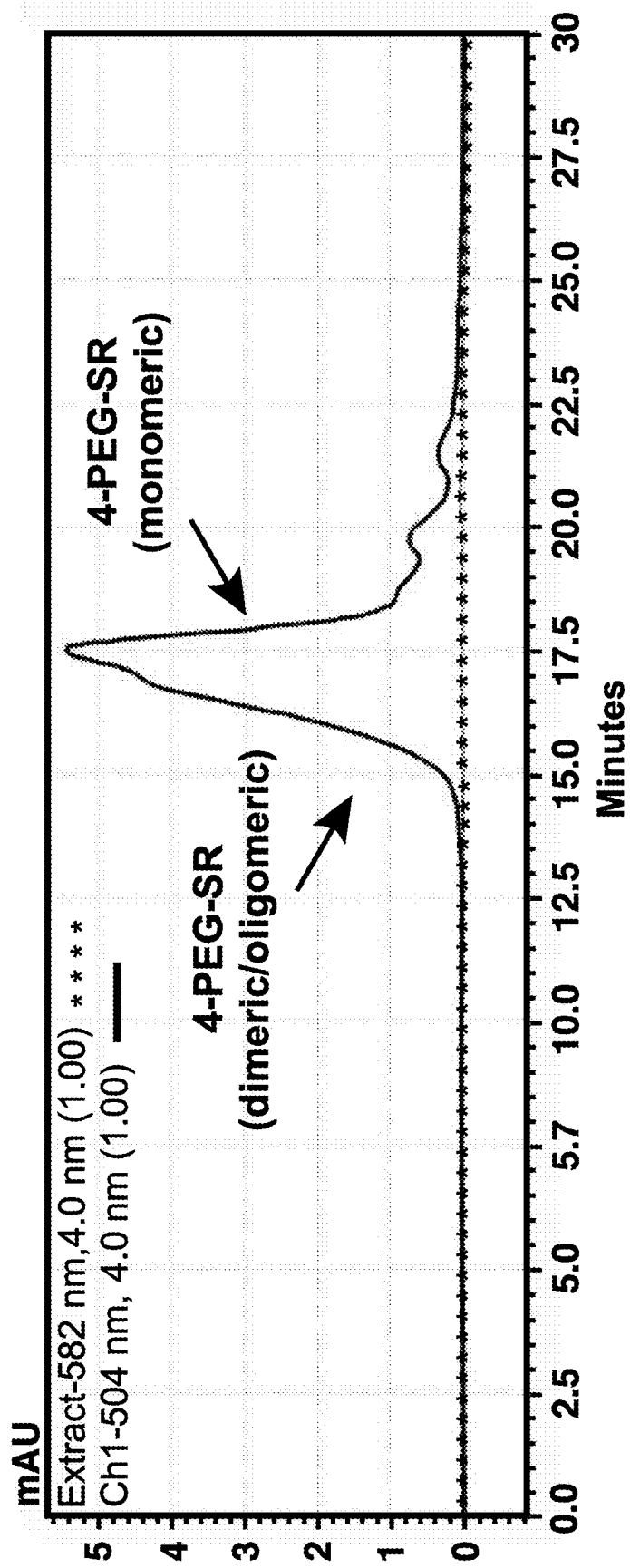
FIG. 18 depicts GPC analysis of supernatant (swelling buffer) of BODIPY-labeled 3.5 wt % hydrogel formed with linker 8 after 72 hours of incubation at 37° C.

GPC analysis was also used to help identify the fragments eluting from non-degradable gels formed with linker 8 (FIG. 18).

IX.4. Monitoring Loss of Gel Mass Over Time for Selected Gel Compositions

In order to probe the effect of erosion probe dye labeling on gel erosion rate, hydrogels were prepared with 4-PEG-SH macromer that was unlabeled with BODIPY erosion probe. Briefly, 200 µL gels were prepared by addition of 186 µL 3.76 wt % 4-PEG-SH macromer solution to 14 µL of a solution of bis-ONDs 7a or 7b in DMSO to yield a final composition of 3.5 wt % 4-4-PEG-SH macromer with 7% DMSO (v/v) and a 1:1 ratio of thiol:OND electrophile. The samples were mixed briefly with a pipet. Self-supporting gels were observed by the inversion test within one minute, but were allowed to stand at room temperature for 20 minutes. The mass of the cured gel was measured before suspending the samples in 6 mL of pH 7.4 0.1M PBS buffer and placing in a 37° C. incubator. At various time points, the gels were briefly removed to room temperature, excess buffer was slowly poured off and wicked away with the edge of a Kimwipe delicate task wipe without touching the gel sample. The mass of the gel was measured, and 6 mL fresh buffer (pre-warmed to 37° C.) was added before returning the sample to 37° C. incubation. This process was continued until no gel remained. The mass of the hydrogel remaining at a given time point over the mass of the cured gel was plotted vs. time (FIG. 19).

For less stable gel formations, we observe a decrease in stability of hydrogels prepared with erosion probe-labeled 4-PEG-SH macromer (FIG. 19B). This is consistent with the expectation that reducing the number of available thiol end-groups on the 4-PEG-SH macromer will lead to a lower cross-link density in the resulting gels, and produce gels that are expected to degrade sooner at a given temperature. We observe reasonable agreement of degradation times for gels formed with either unlabeled 4-PEG-SH macromer or macromer with 3% of its thiol end-groups labeled with a BODIPY erosion probe, particularly for more stable hydrogel formulations (as shown in FIG. 19A). Even so, the use of the probe-labeled macromer is still valuable for comparing erosion behaviors of gels under physiologically relevant conditions.

IX.5. Time-Lapse Photography

Time-lapse photography performed to observe reverse gelation upon prolonged heating of hydrogels under swelling conditions at different buffered pH values. Briefly, 4×600

μL hydrogels comprised of 3.5 wt % 4-PEG-SH+bis-OND 7a in pH 7.4 100 mM potassium phosphate buffer containing 7% DMSO (v/v) were formed in glass culture tubes and allowed to set for 20 minutes. A non-degradable control gel from bis-EONB 8 was prepared. A glass bead (~160 mg, stained with blue Sharpie-brand marker to improve visibility) was placed carefully on top of each gel. The remainder of the culture tube was filled with ~7 of buffer at the appropriate pH (pH 1.2 HCl/NaCl with 1 mg/mL pepsin, pH 5.0 acetate, pH 7.4 phosphate buffered saline, and pH 9.0 sodium carbonate buffer). The non-degradable control was diluted with pH 7.4 phosphate buffer. The tubes were sealed with lab parafilm and incubated in a 37° C. oil bath. Photos were collected every 2 minutes for 22 hours using Chronolapse software (v.1.0.4) and a Creative Labs webcam. Photographs were compiled in chronological order using iMovie software, with each photo occupying one 0.1 s frame. The resulting video is available as Supporting Movie S2.

Figure 20:
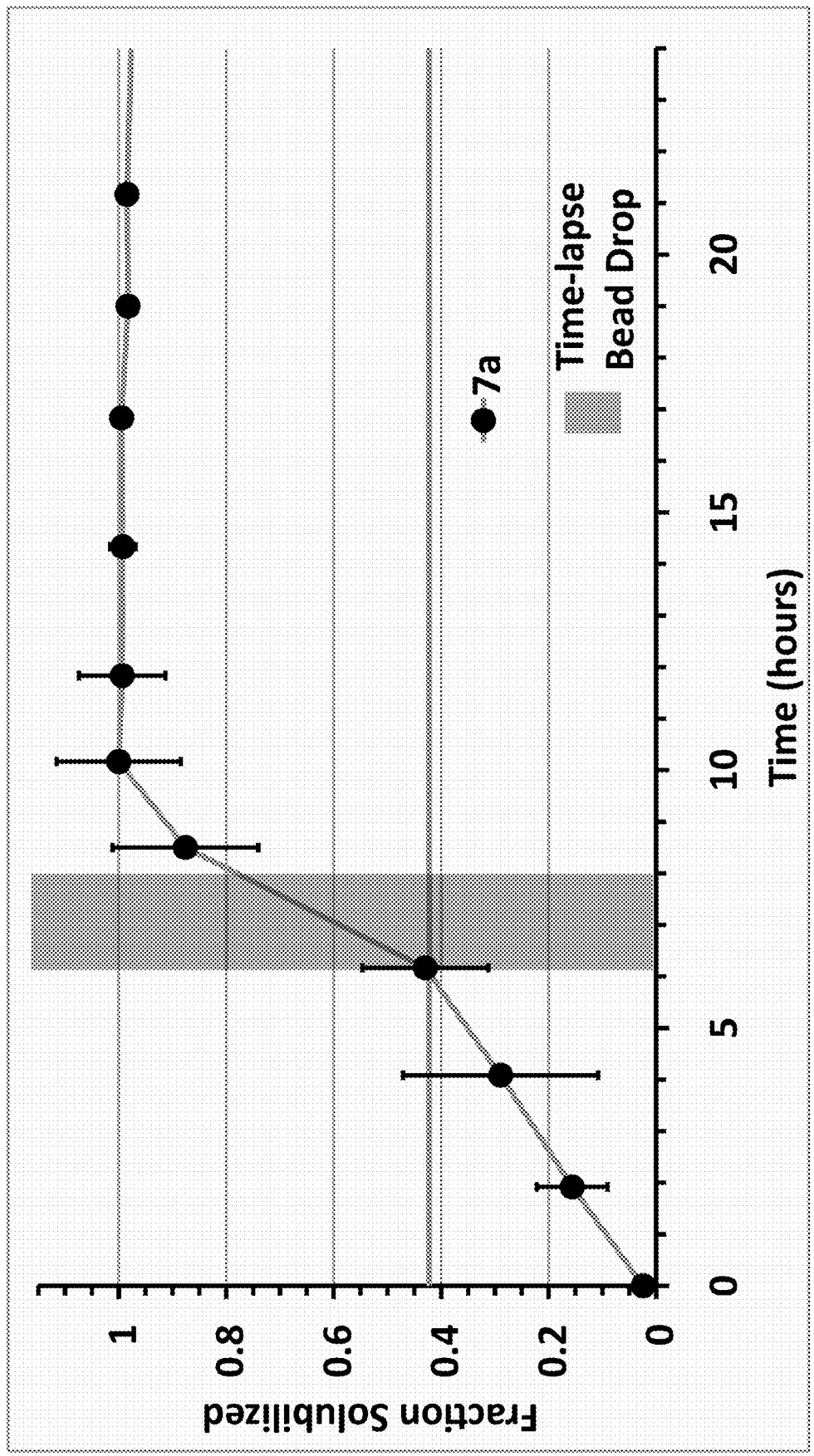
FIG. 20 depicts overlay of erosion profile for PEG-OND (7a) hydrogel and time frame of gel collapse observed in time-lapse video (S2 Video, described infra).

The time at which the glass bead reached the bottom of the tube was recorded. The span of time between when the first and last bead dropped was in reasonable agreement with the time of gel dissolution observed in erosion studies (FIG. 20, vertical highlighted band).

X. Comparison of Release of Entrained Cargo

X.1.a. FITC Labeling of Bovine Serum Albumin WT Qβ Virus-Like Particles

Figure 43A:
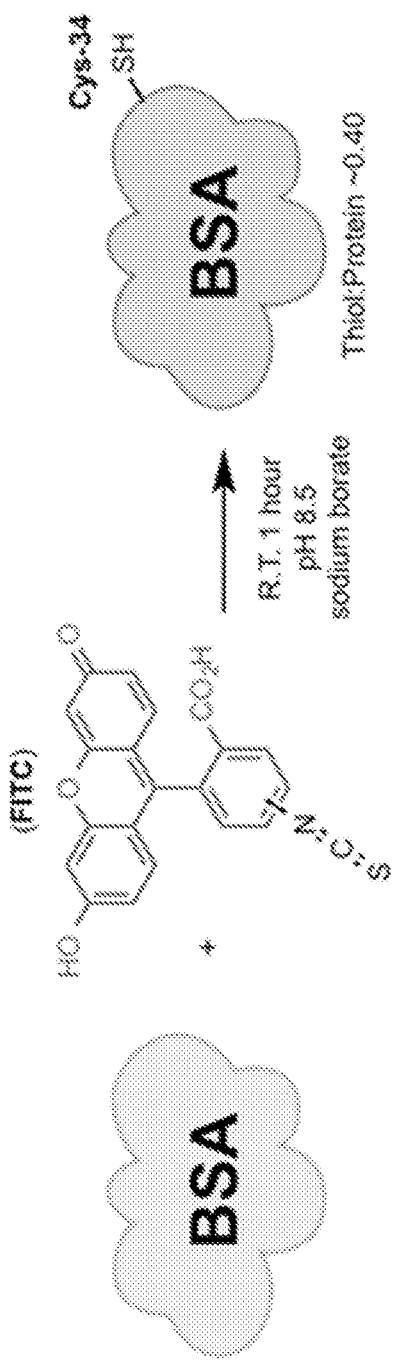
FIG. 43A depicts labeling of bovine serum albumin with FITC using sodium borate buffer.

Bovine serum albumin (BSA) contains a conserved free cysteine (cys-34) that can be oxidized or capped as a mixed disulfide during isolation and storage of the protein. The thiol content of a stock of BSA (Sigma-Aldrich) was determined by the Ellman-Wilson assay and found to be ~0.40 thiols per BSA protein. 500 μL of a 5 mg/mL solution of bovine serum albumin (BSA) in pH 8.5 100 mM sodium borate buffer was added slowly to a solution of fluorescein isothiocyanate (FITC, 2.5 μL 25.7 mM stock in DMSO, 0.07 equiv dye per primary amine on BSA) at room temperature and stirred for one hour (FIG. 43A). The resulting labeled protein was purified by 5 buffer exchanges with pH 7.4 100 mM phosphate buffered saline on Amicon size exclusion filter (MWCO 3 kDa).

X.1.b. FITC Labeling of BSA Followed by Capping of Cysteine-34

Figure 43B:
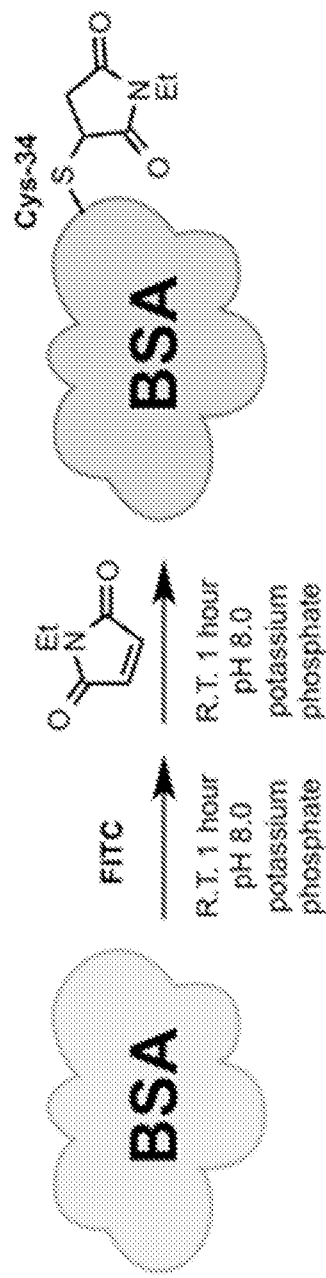
FIG. 43B depicts labeling of bovine serum albumin with FITC using potassium phosphate buffer.

500 μL of a 7 mg/mL BSA solution in pH 8.0 phosphate buffer was added slowly to a solution of fluorescein isothiocyanate (FITC, 10 μL 25.7 mM stock in DMSO, 0.32 equiv dye per primary amine on BSA) at room temperature and rotated for one hour. At this time, 2 equivalents of N-ethylmaleimide were added to cap free cysteine-34, and rotated for an additional 1 hour at room temperature (FIG. 43B) before loading the entire reaction mixture onto a PD-10 desalting column equilibrated in pH 7.4 0.1 M PBS. A bright yellow band was eluted with 3.5 mL of PBS to yield labeled BSA at ~2 mg/mL. This solution was carried on to prepare hydrogels with entrained dye-labeled and thiol-depleted BSA (see section X.2).

X.1. FITC Labeling WT Virus-Like Particles

Figure 44:
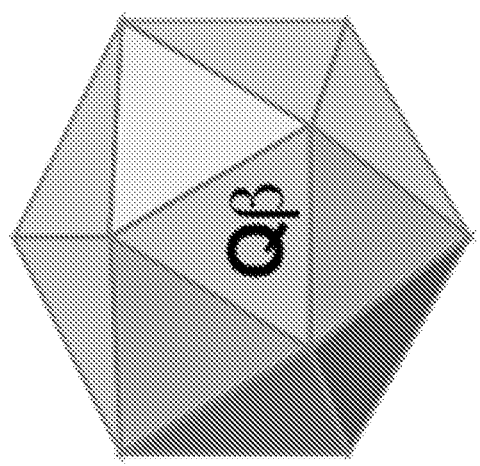
FIG. 44 depicts labeling of Qβ virus-like particle with FITC using standard protocol.
Figure 44:
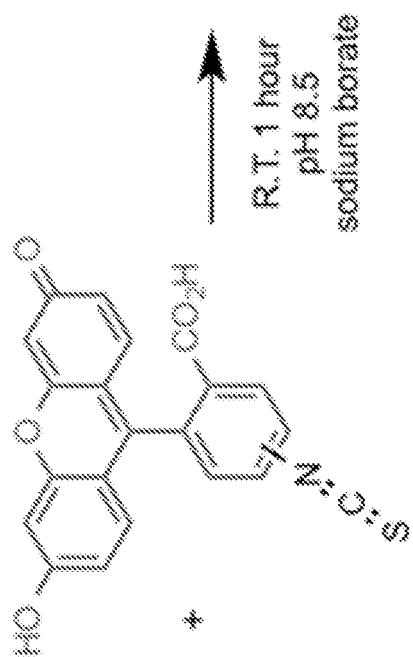
Figure 44:
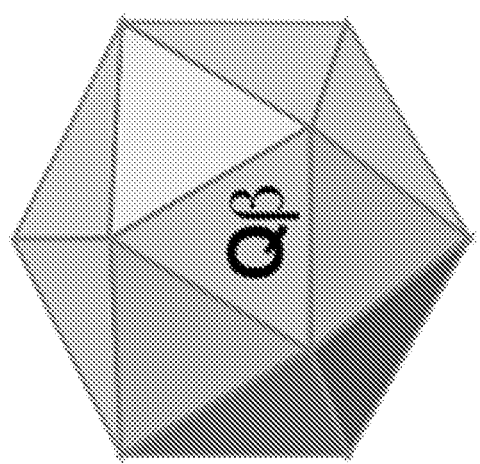

Wild-type Qβ virus-like particles were obtained by recombinant expression in *E. coli* and purified by sucrose gradient using a previously described protocol. 500 μL of a 4.6 mg/mL solution of wild-type Qβ virus-like particles in pH 8.5 100 mM sodium borate buffer was added slowly to a solution of fluorescein isothiocyanate (FITC, 20 μL 25.7 mM stock in DMSO, 0.19 equiv dye per primary amine on particle) at room temperature and stirred for one hour (FIG. 44). The resulting labeled protein nanoparticle was purified by 12 buffer exchanges with pH 7.4 100 mM phosphate buffered saline on Amicon size exclusion filter (MWCO 3 kDa).

X.2. Entrainment of Cargos and Monitoring Release

Figure 45:
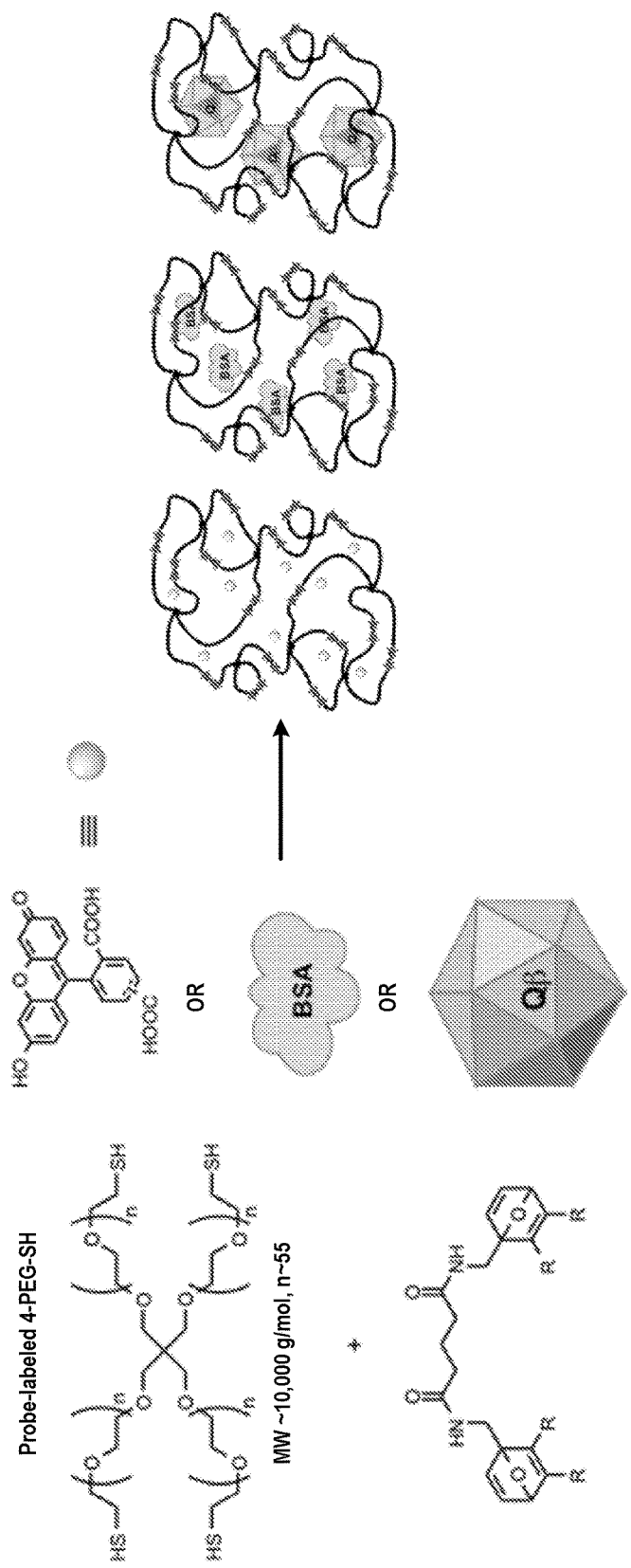
FIG. 45 depicts entrainment of fluorescent cargo in hydrogels for comparison of release rates.

The labeled protein solutions prepared as described in the previous section were diluted three-fold with pH 7.4 100 mM phosphate buffer and used to dissolve the 4-PEG-SH macromer at 3.76 wt %. This solution was used in an identical manner as pure 4-PEG-SH solution for the purpose of forming PEG-OND hydrogels (FIG. 45). All samples formed self-supporting hydrogels within 1 min after mixing, as determined by the inversion test.

Three sets of three 60 μL gels were prepared using linkers 7a, 7b, and 8, respectively. The first set contained 1 mM small molecule probe 5/6-carboxyfluorescein, while the second and third sets contained FITC labeled BSA and Qβ virus-like particle, respectively. The gels were allowed to set for 30 minutes at room temperature before dilution with 3 mL of pH 7.4 100 mM phosphate buffered saline. The samples were incubated at 37° C. and the increase in absorbance of the supernatant at 497 nm was monitored. The fraction of released dye was plotted against incubation time. Least-squares kinetic fitting to a first-order rate law was performed for release profiles obtained for carboxyfluorescein cargo, and for the release of BSA from non-degradable PEG-EONB (8) hydrogel (Solver plug-in, Microsoft Excel).

X.3. Supplementary Note On Entrained Cargo Release Rates and Hydrogel Mesh Size

The differences in release rates correlate well with the hydrodynamic radius of the entrained cargo relative to the mesh size of the hydrogels employed in these studies (See Table S2). The mesh size increases during the course of degradation, allowing materials that are otherwise unable to diffuse through the gel network to be released before complete disintegration of the gel. The hydrodynamic radii of encapsulated cargoes are 0.8 nm, 3.48 nm, and 14.5 nm for carboxyfluorescein, bovine serum albumin, and wild-type Qβ virus-like particle, respectively. Smaller cargoes are able to diffuse out of the hydrogel network, with carboxyfluorescein diffusion occurring very rapidly, and BSA experiencing some hindrance. With an average mesh size of 14.0±1.0 nm for equilibrium swelled hydrogels formed using linkers 7a, 7b, and 8, it is clear that release of bacteriophage Qβ protein nanoparticles, with a diameter twice the average mesh size, should be significantly retarded and were observed to be directly dependent on hydrogel degradation.

Figures 21A, 21B:
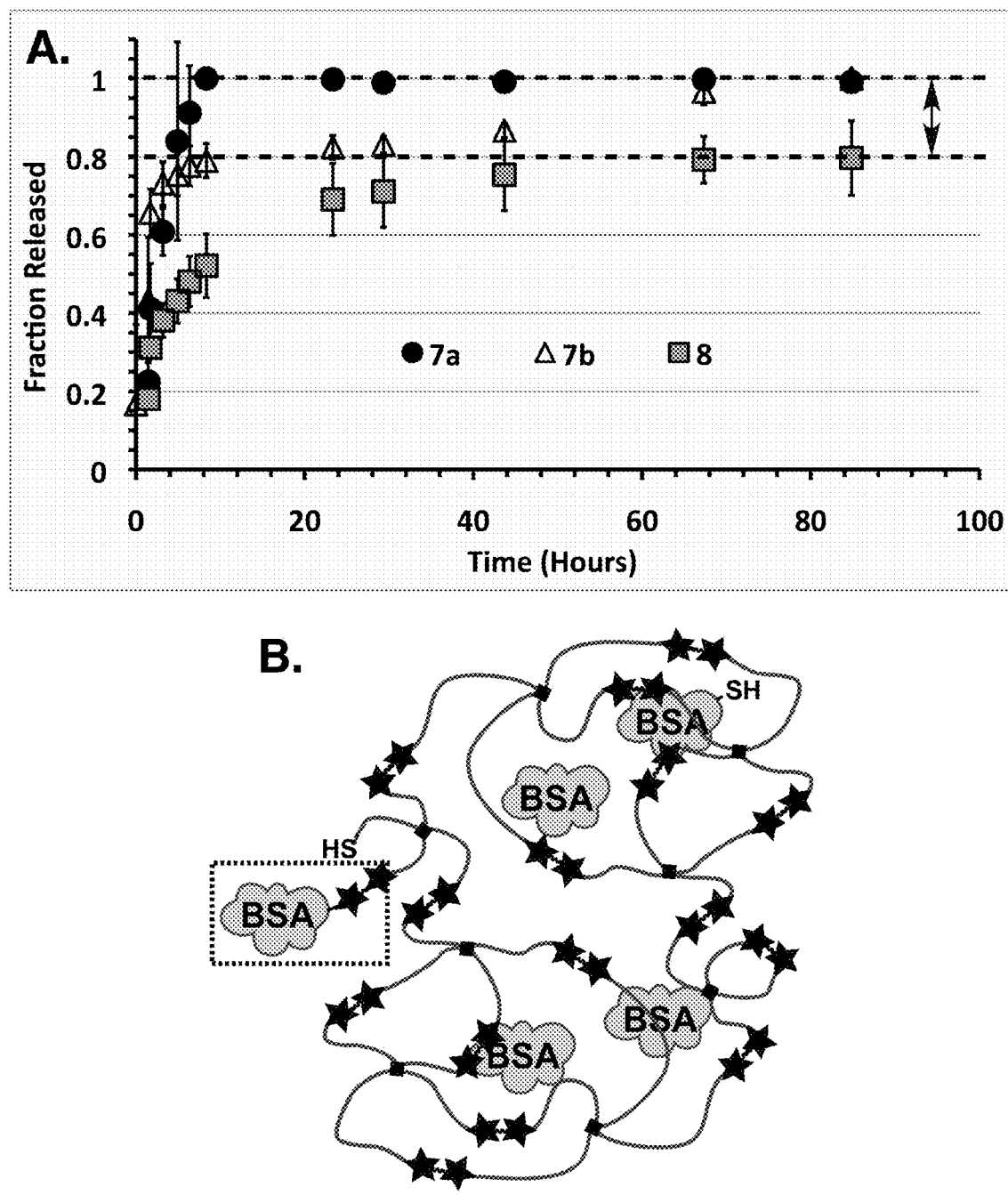
FIG. 21A depicts the release of entrained FITC-labeled BSA with ~0.4 accessible thiols per protein from bis-OND hydrogels 7a, 7b, and 8. Tracking the fraction of BSA released over time reveals that ~20% of BSA becomes tethered to the network (horizontal dashed lines).
FIG. 21B is a representation of BSA entrained in bis-OND hydrogels and tethered to the network by reaction with terminal OND electrophiles (dotted box).
Figure 22:
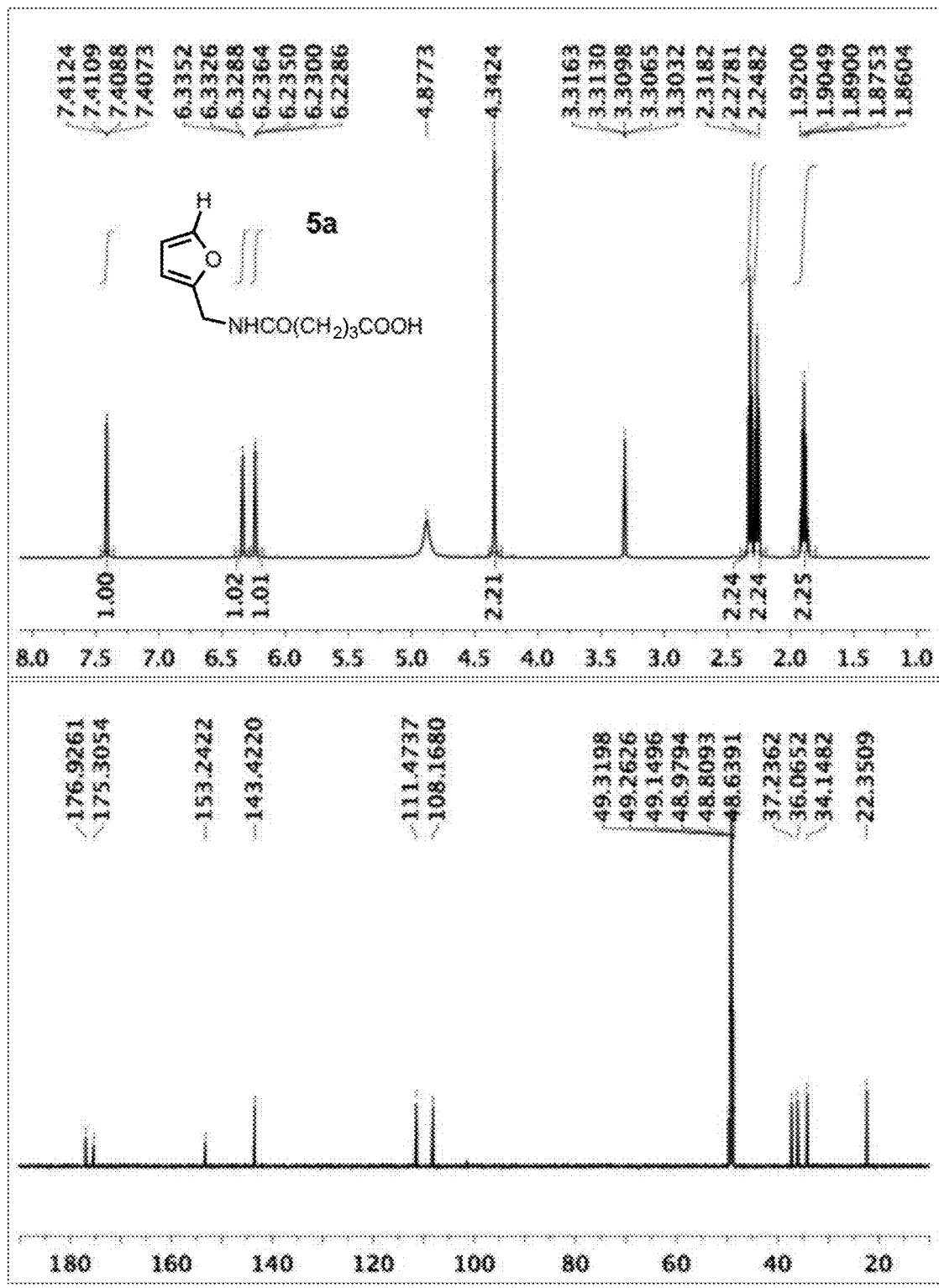
Figure 23:
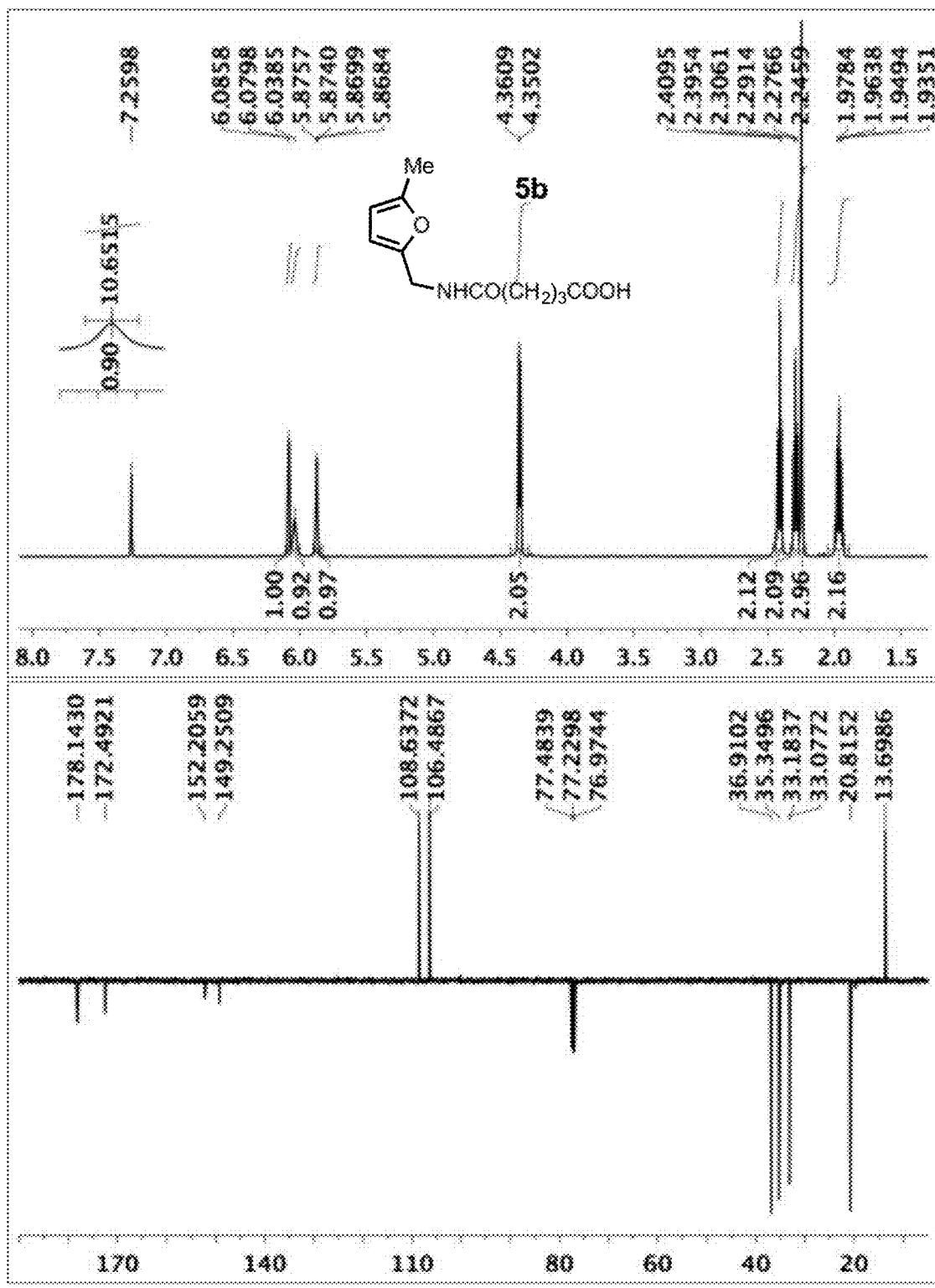
FIG. 23 depicts $^1$H NMR spectra of 5b.
Figure 24:
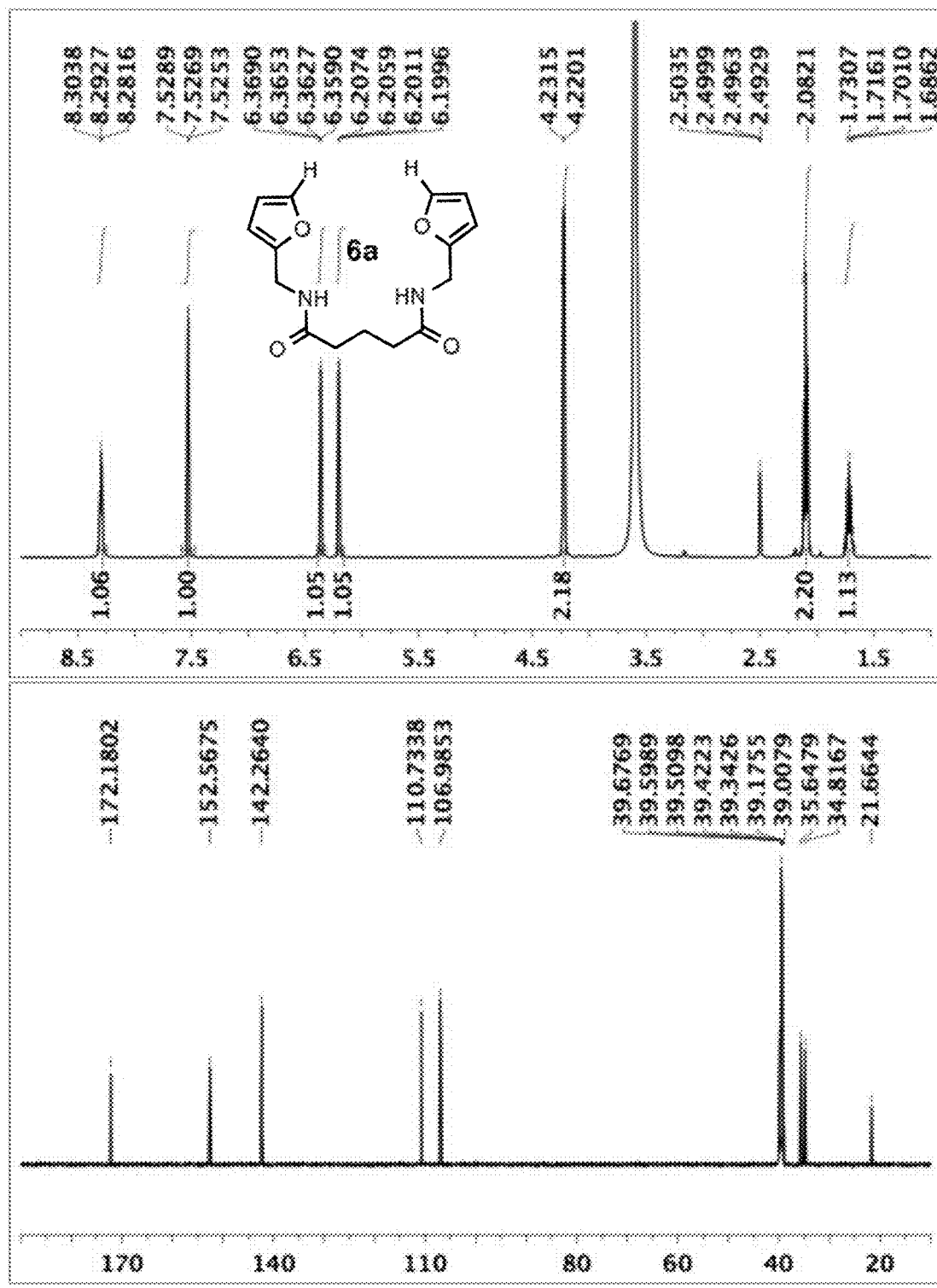
Figure 25:
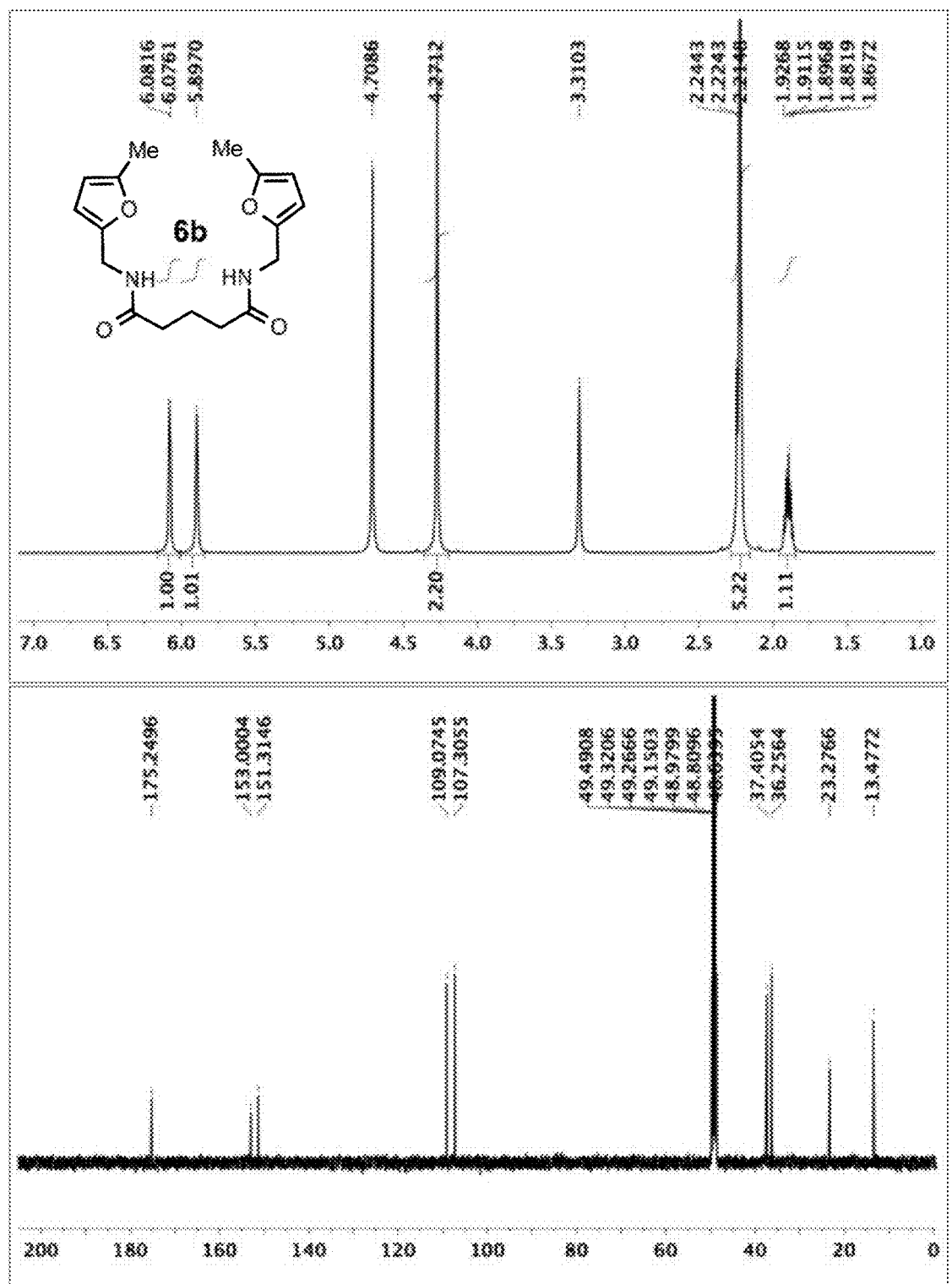
FIG. 25 depicts $^1$H NMR spectra of 6b.
Figure 26:
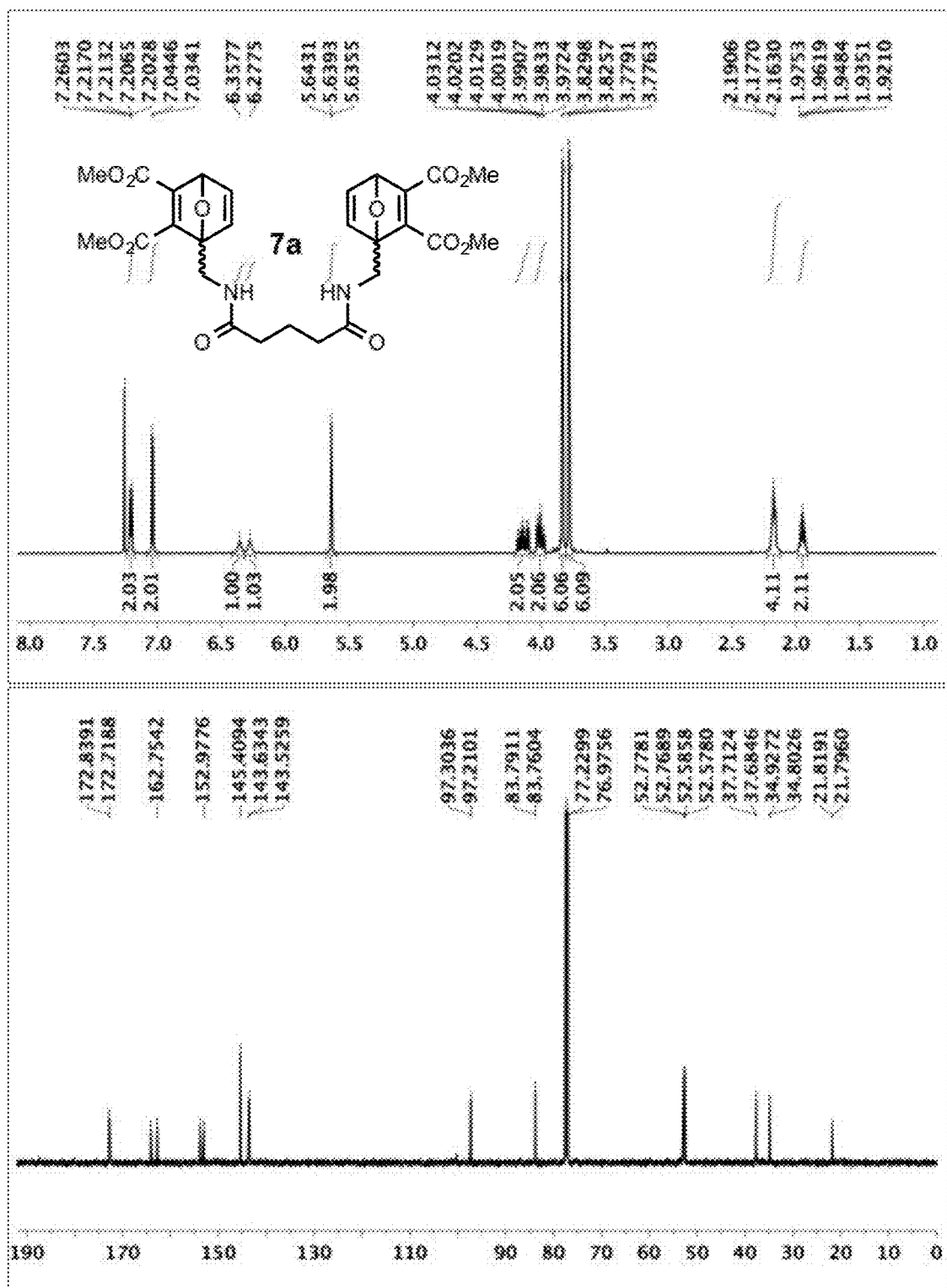
Figure 27:
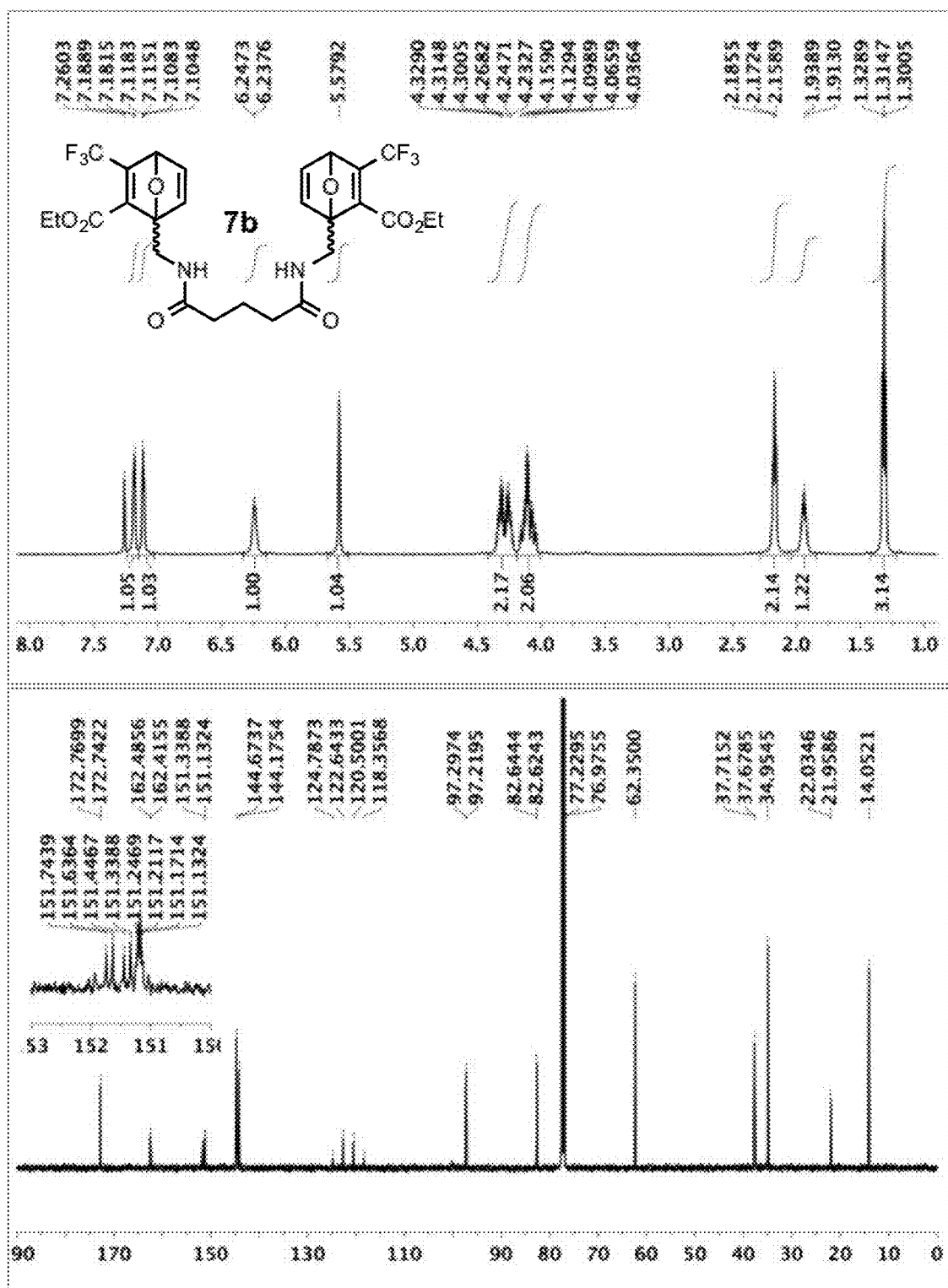
FIG. 27 depicts $^1$H NMR spectra of 7b.
Figure 28:
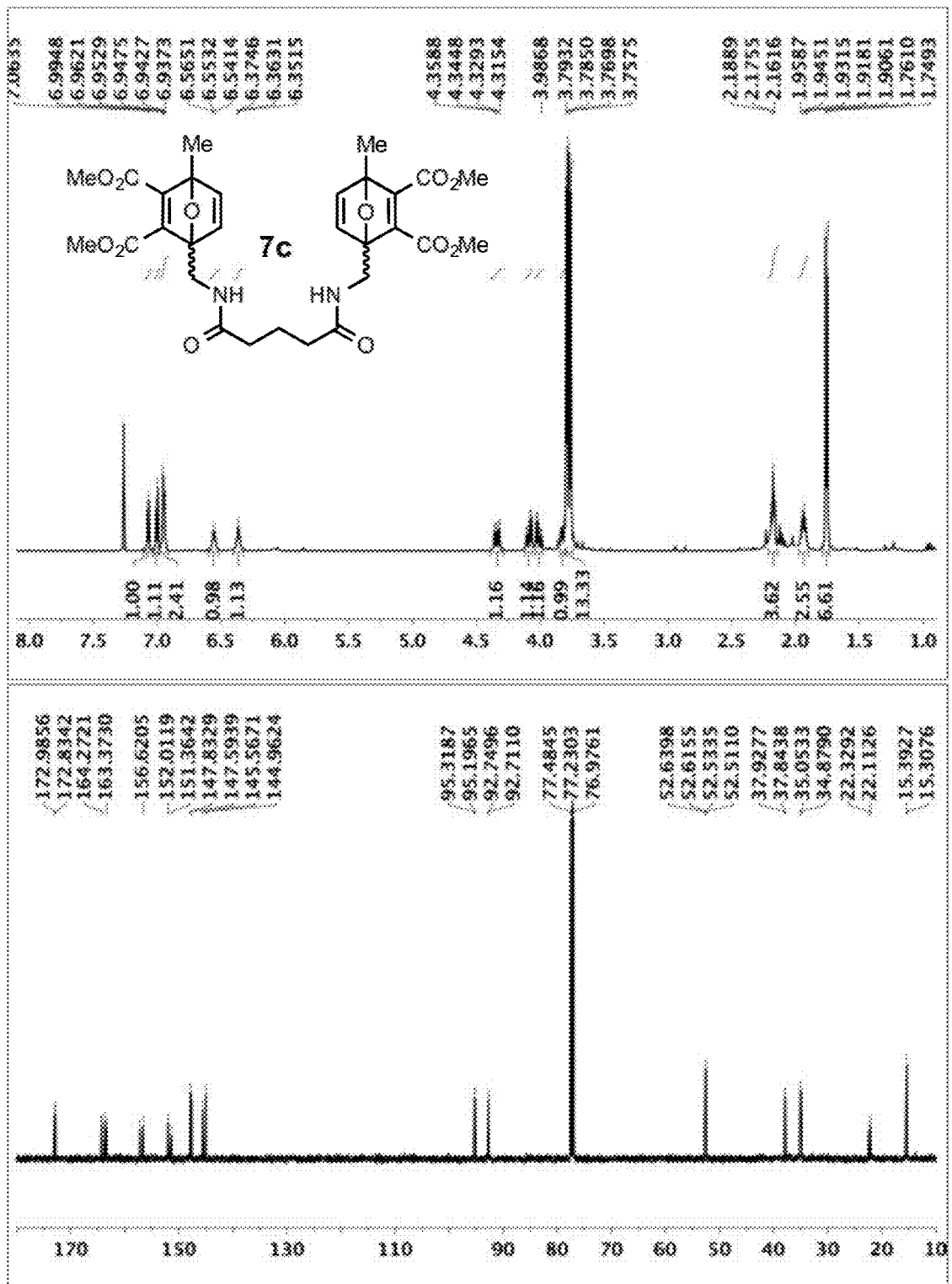
FIG. 28 depicts $^1$H NMR spectra of 7c.
Figure 29:
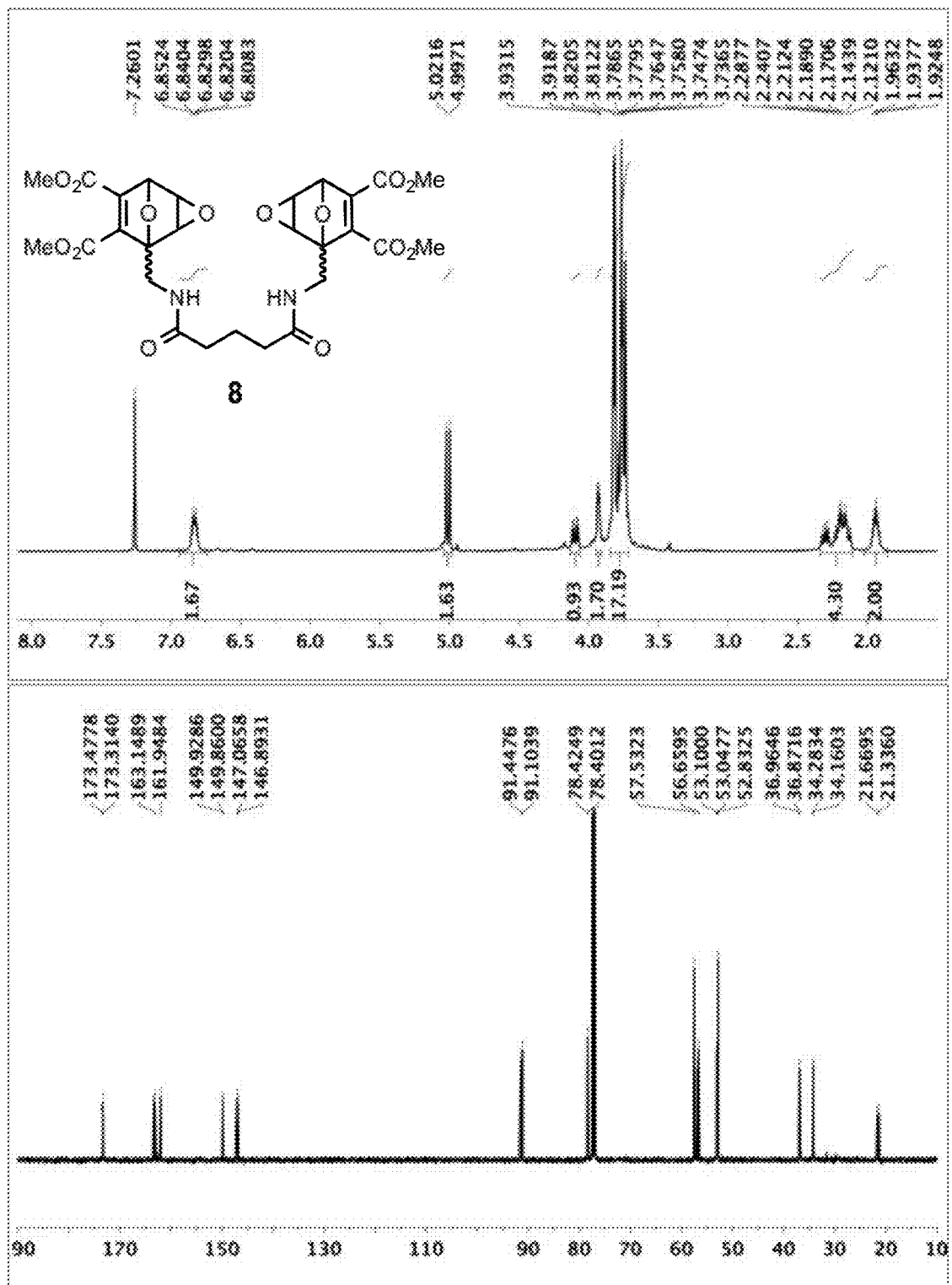
FIG. 29 depicts $^1$H NMR spectra of 8.
Figure 30:
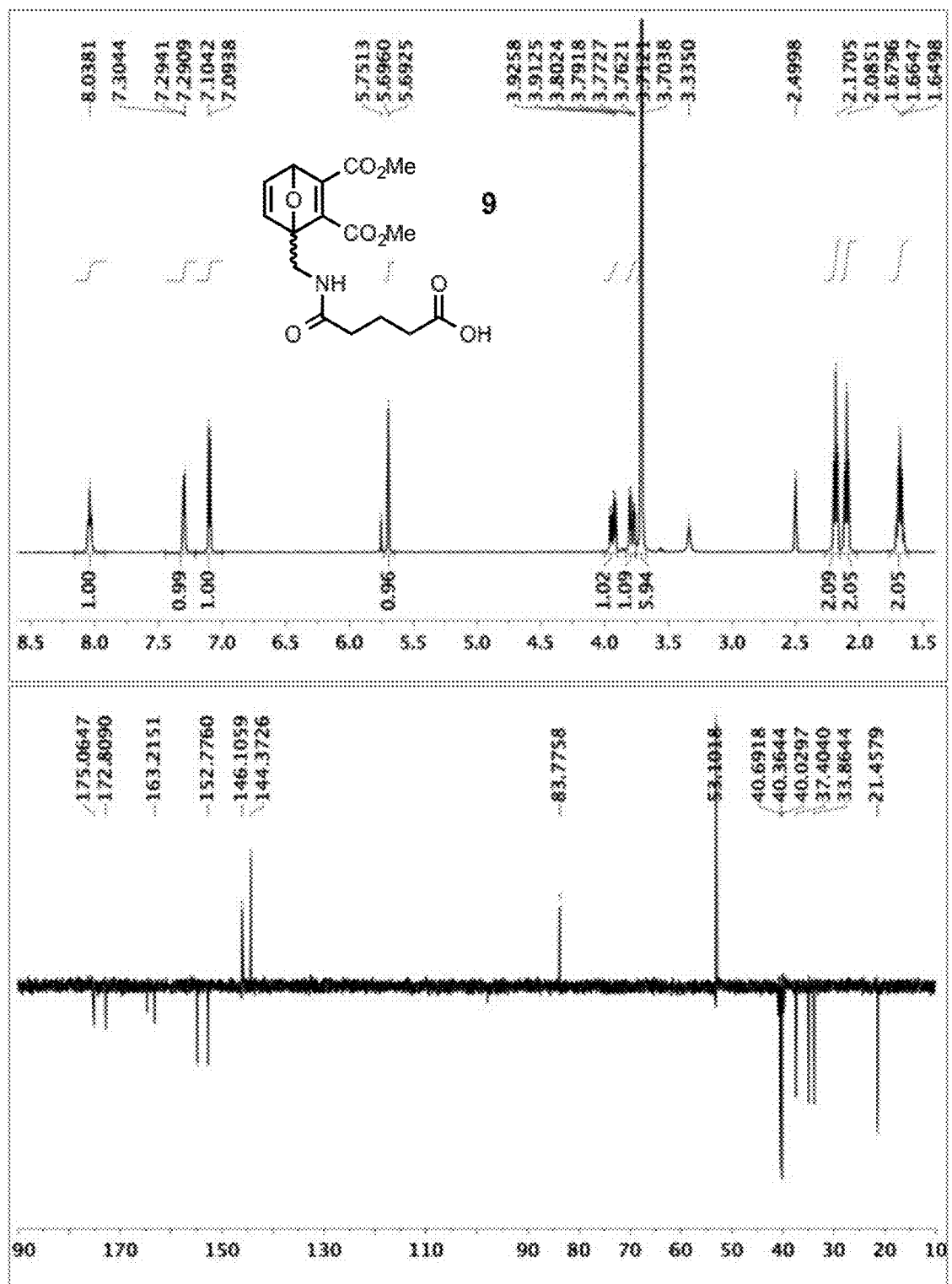
FIG. 30 depicts $^1$H NMR spectra of 9.
Figure 31:
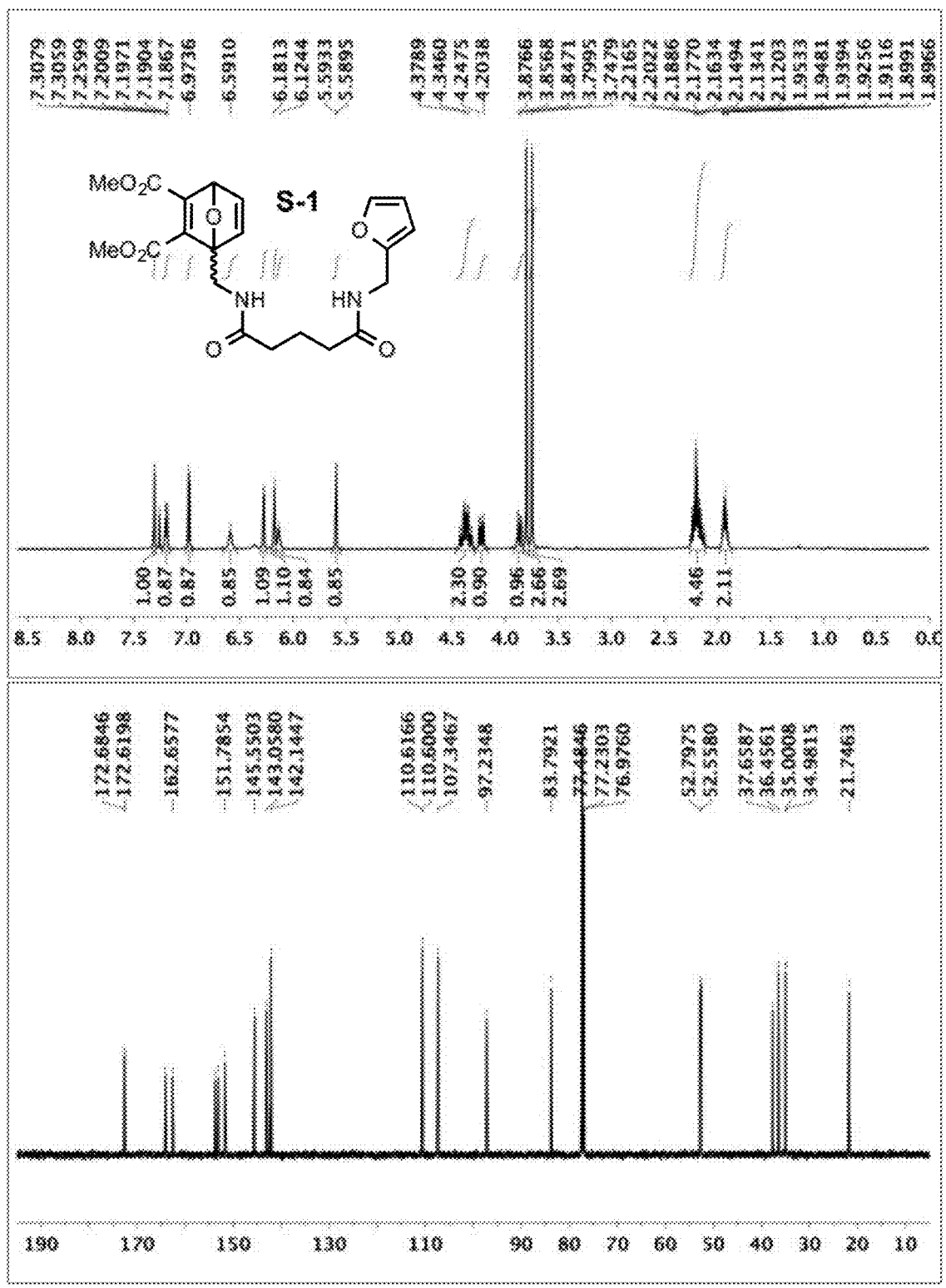
FIG. 31 depicts $^1$H NMR spectra of S-1.
Figure 32:
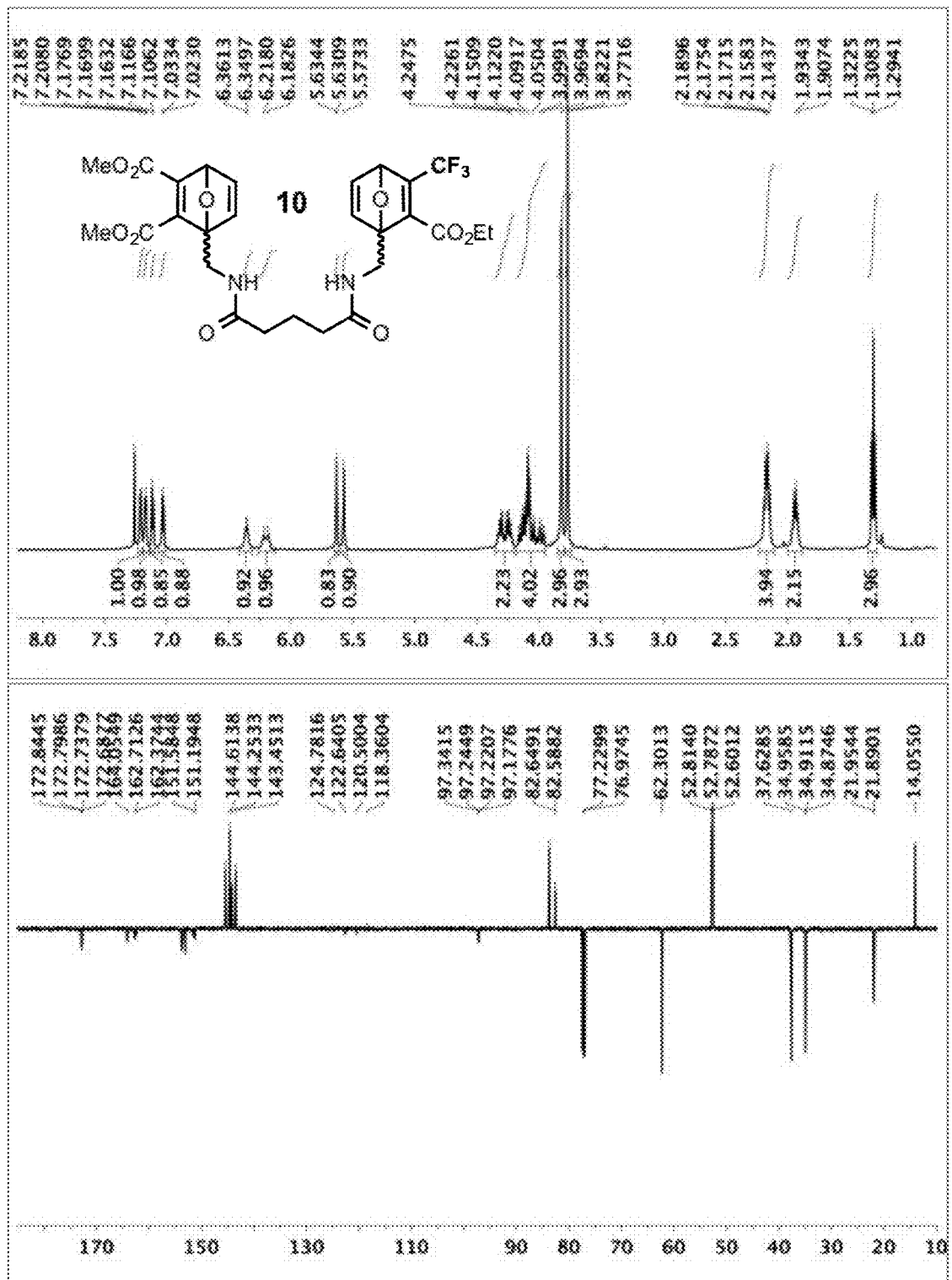
FIG. 32 depicts $^1$H NMR spectra of 10.
Figure 33:
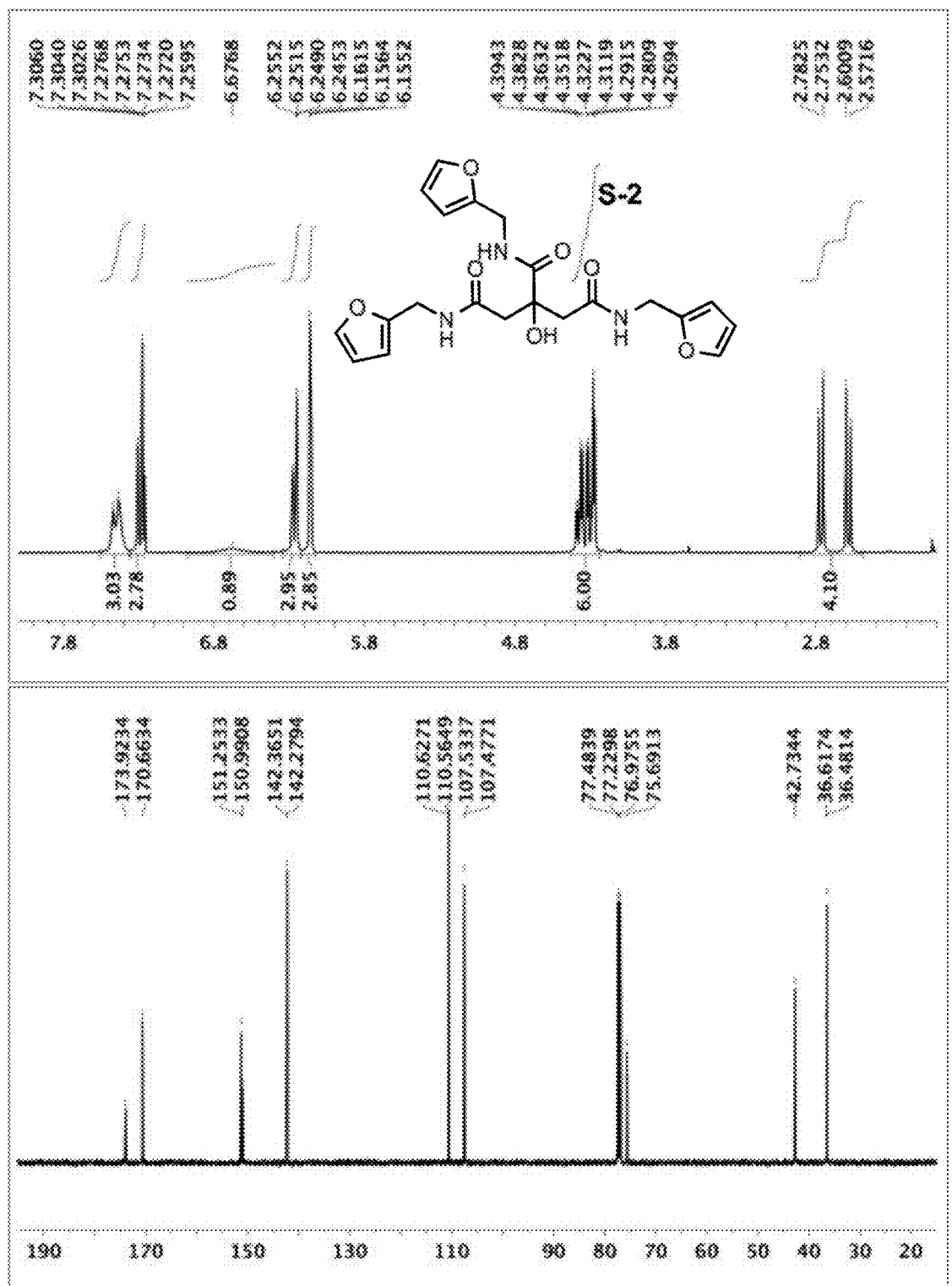
FIG. 33 depicts $^1$H NMR spectra of S-2.
Figure 34:
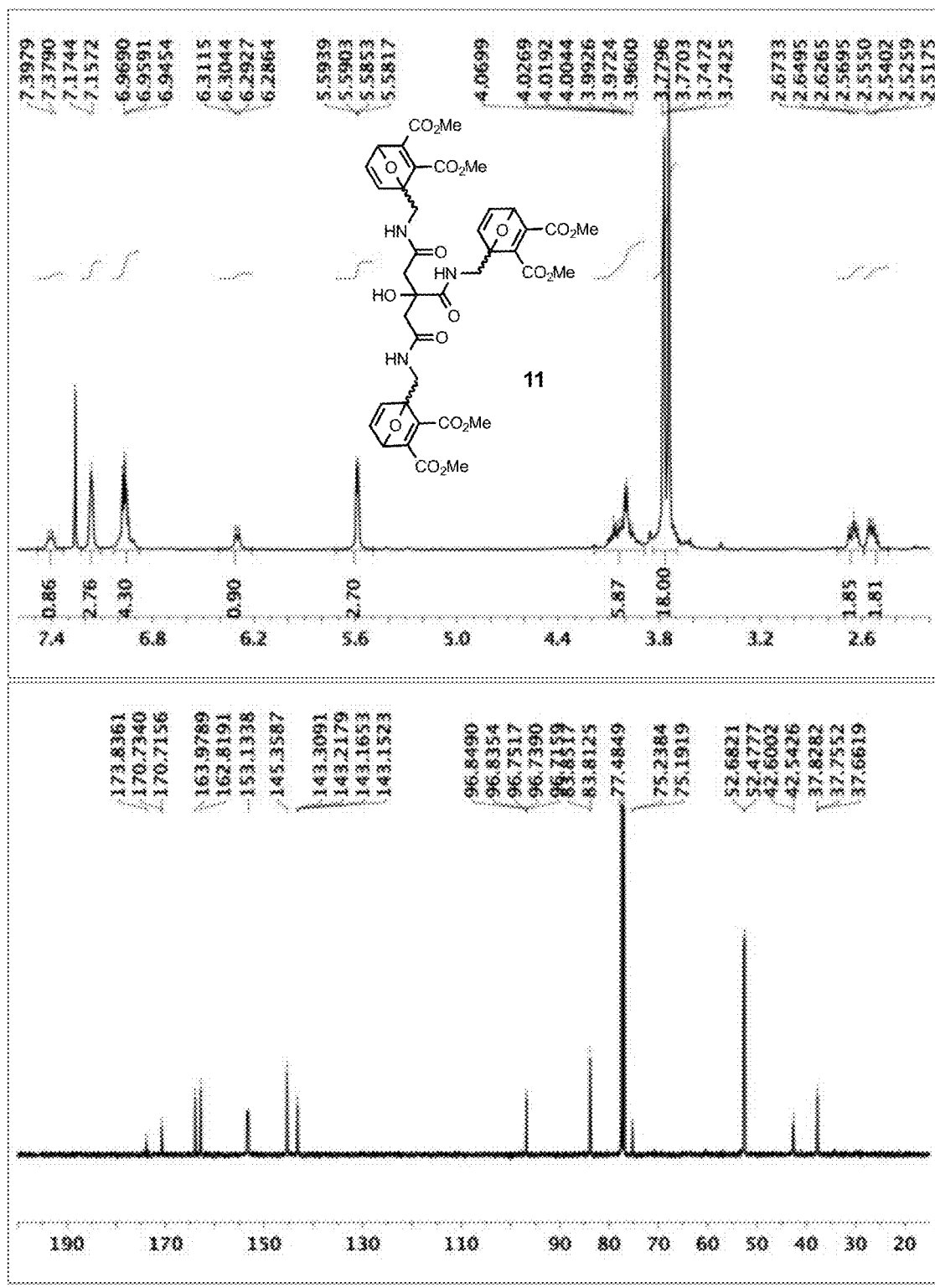
FIG. 34 depicts $^1$H NMR spectra of 11.
Figure 35:
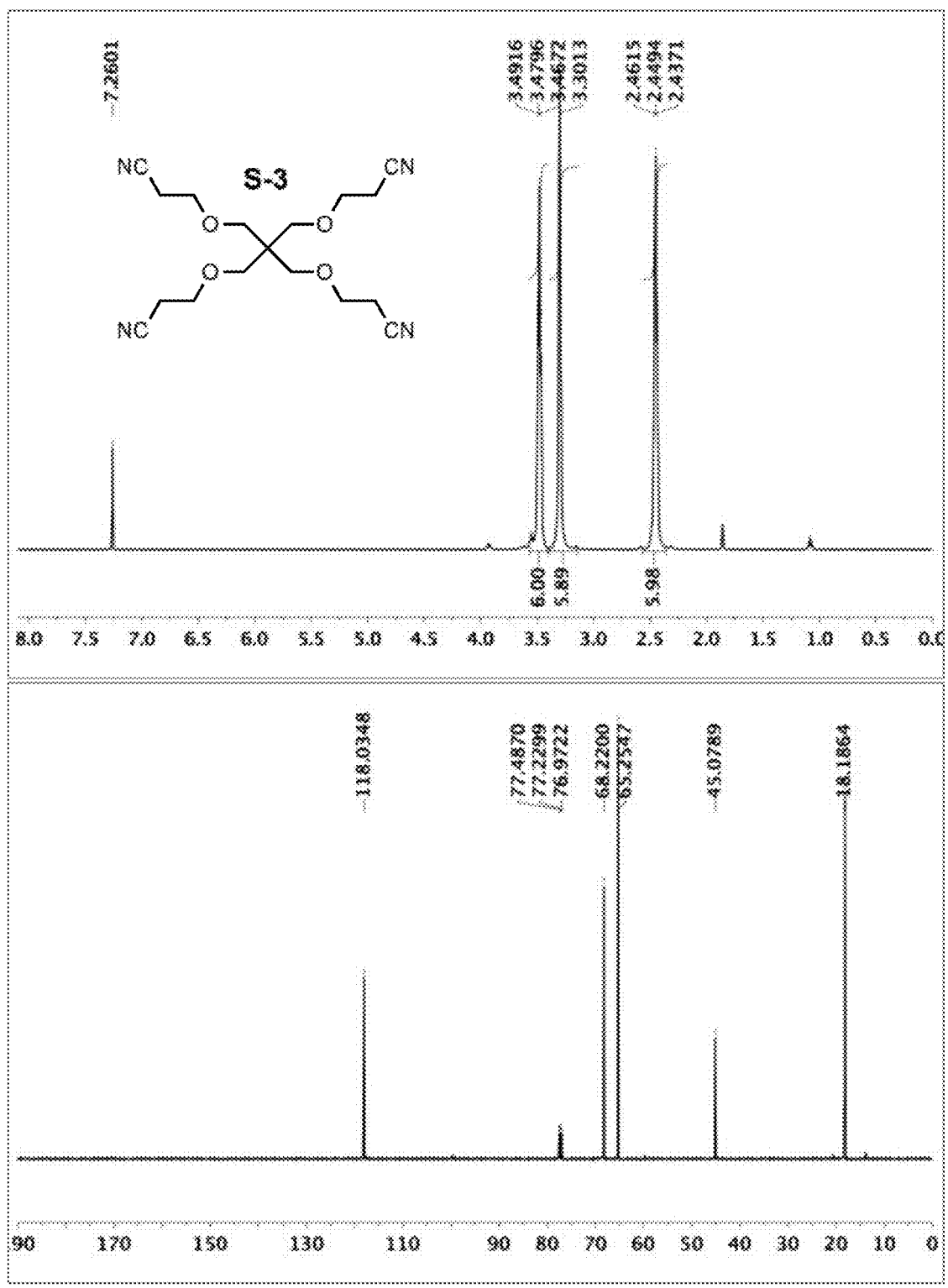
FIG. 35 depicts $^1$H NMR spectra of S-3.
Figure 36:
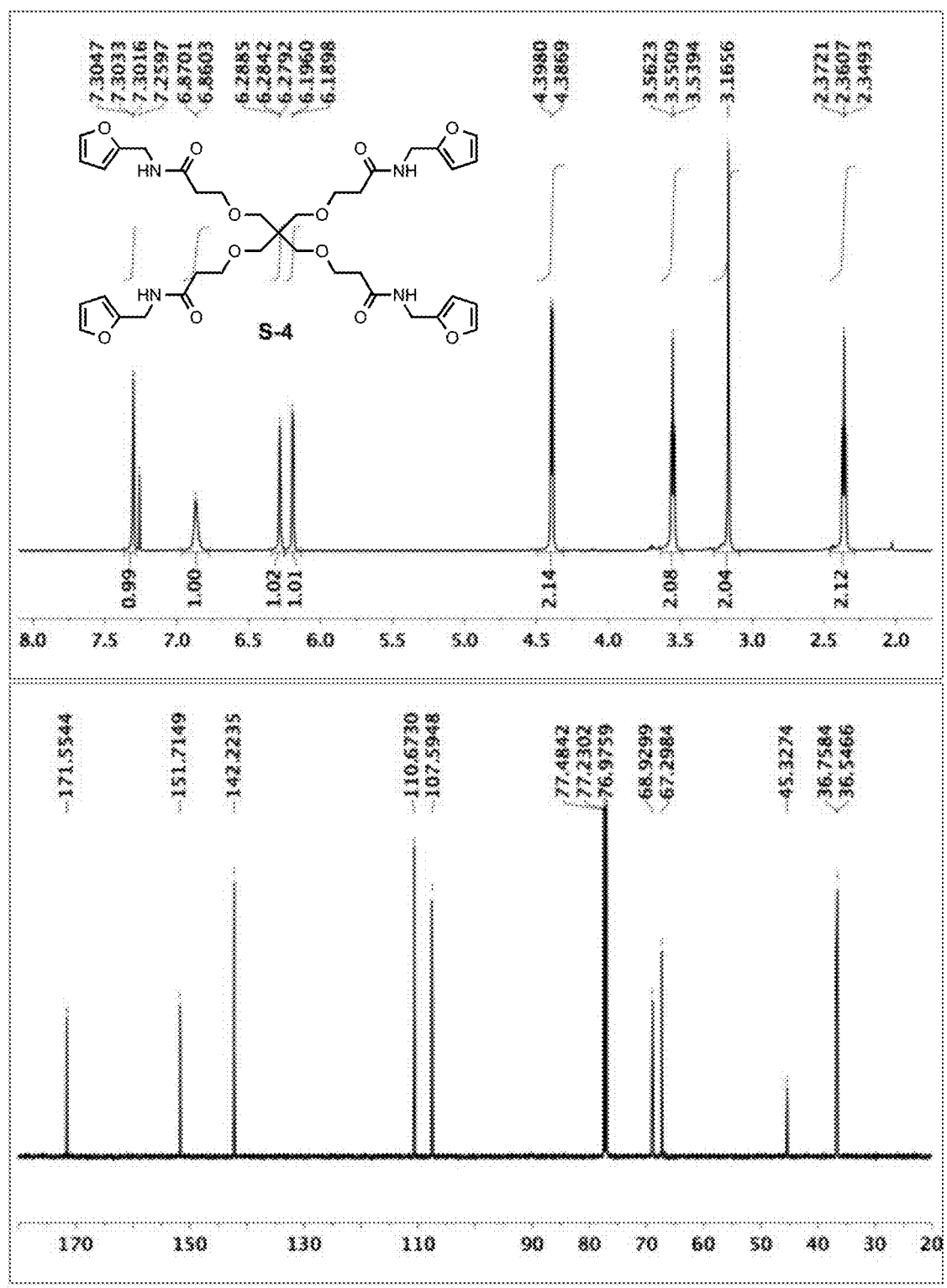
FIG. 36 depicts $^1$H NMR spectra of S-4.
Figure 37:
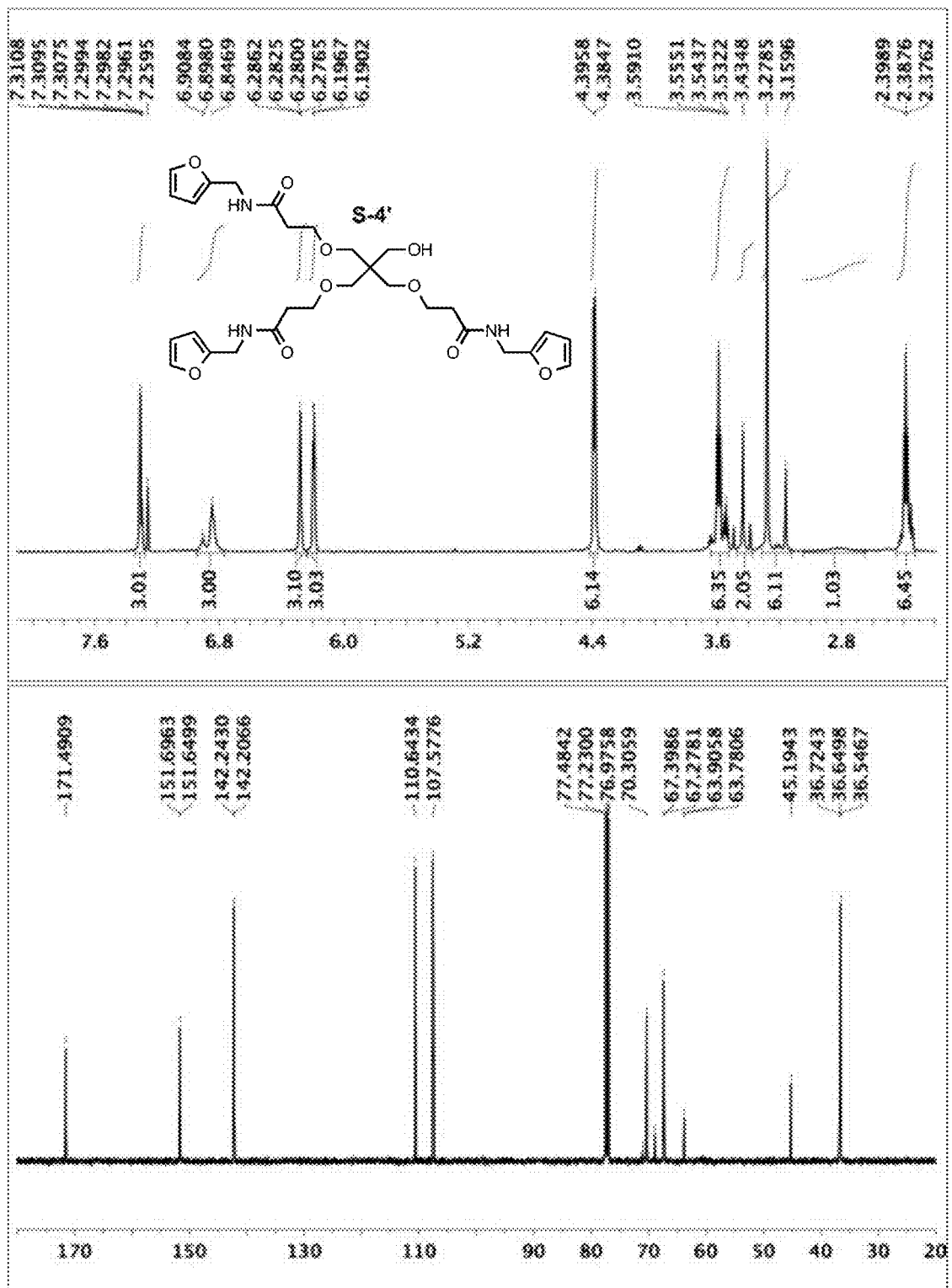
FIG. 37 depicts $^1$H NMR spectra of S-4'.
Figure 38:
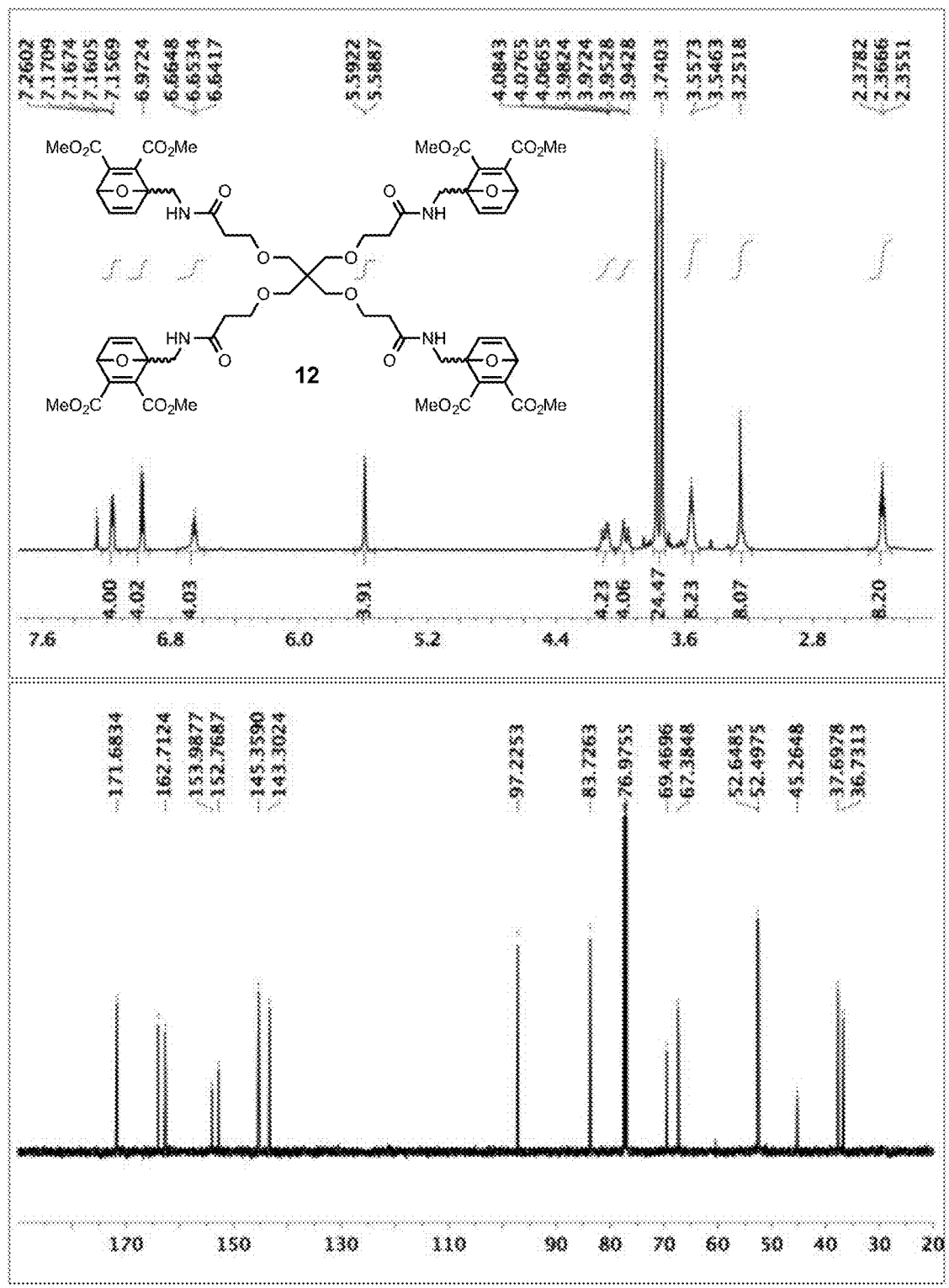
FIG. 38 depicts $^1$H NMR spectra of 12.
Figure 39:
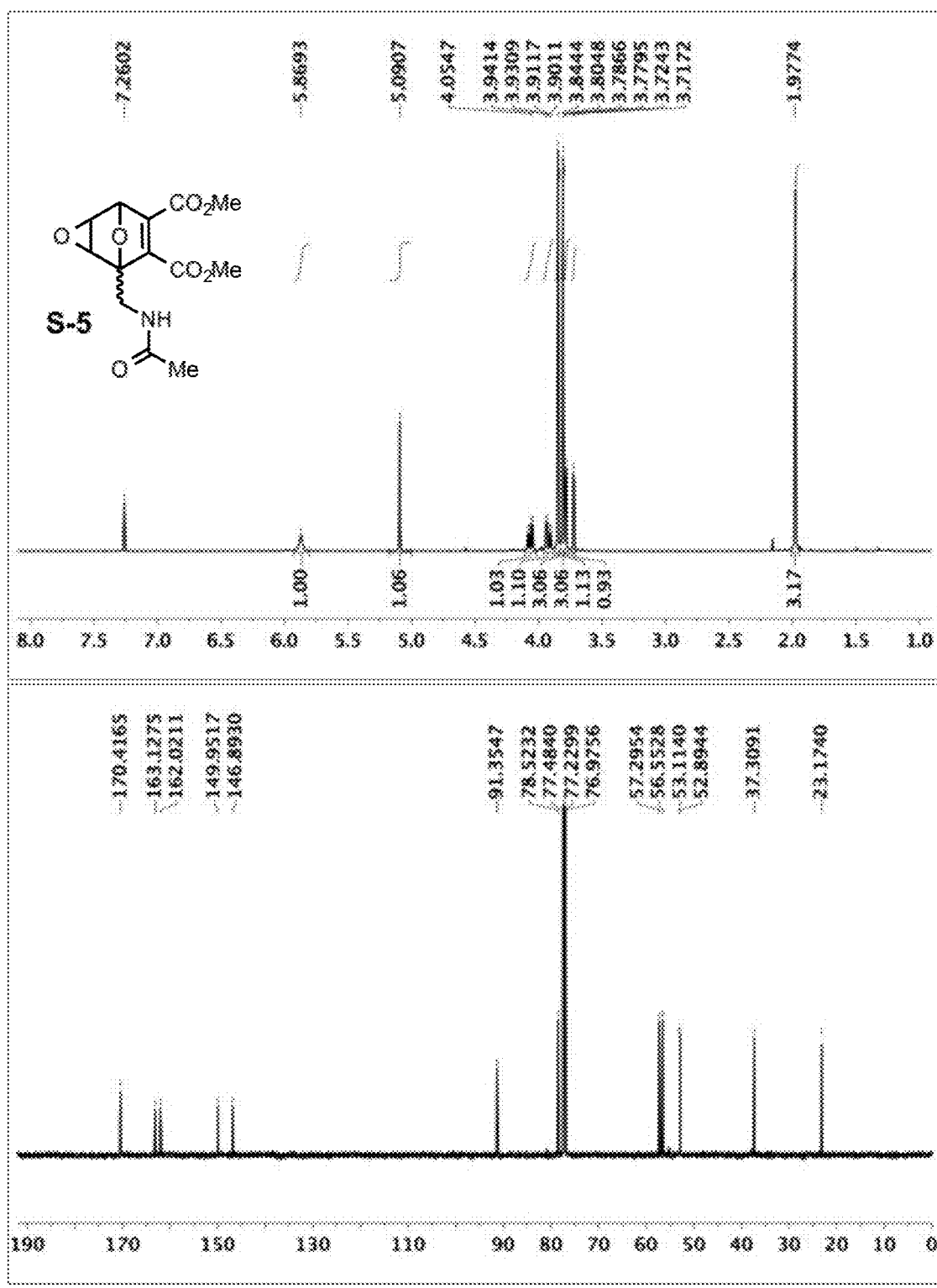
FIG. 39 depicts $^1$H NMR spectra of S-5.
Figure 40:
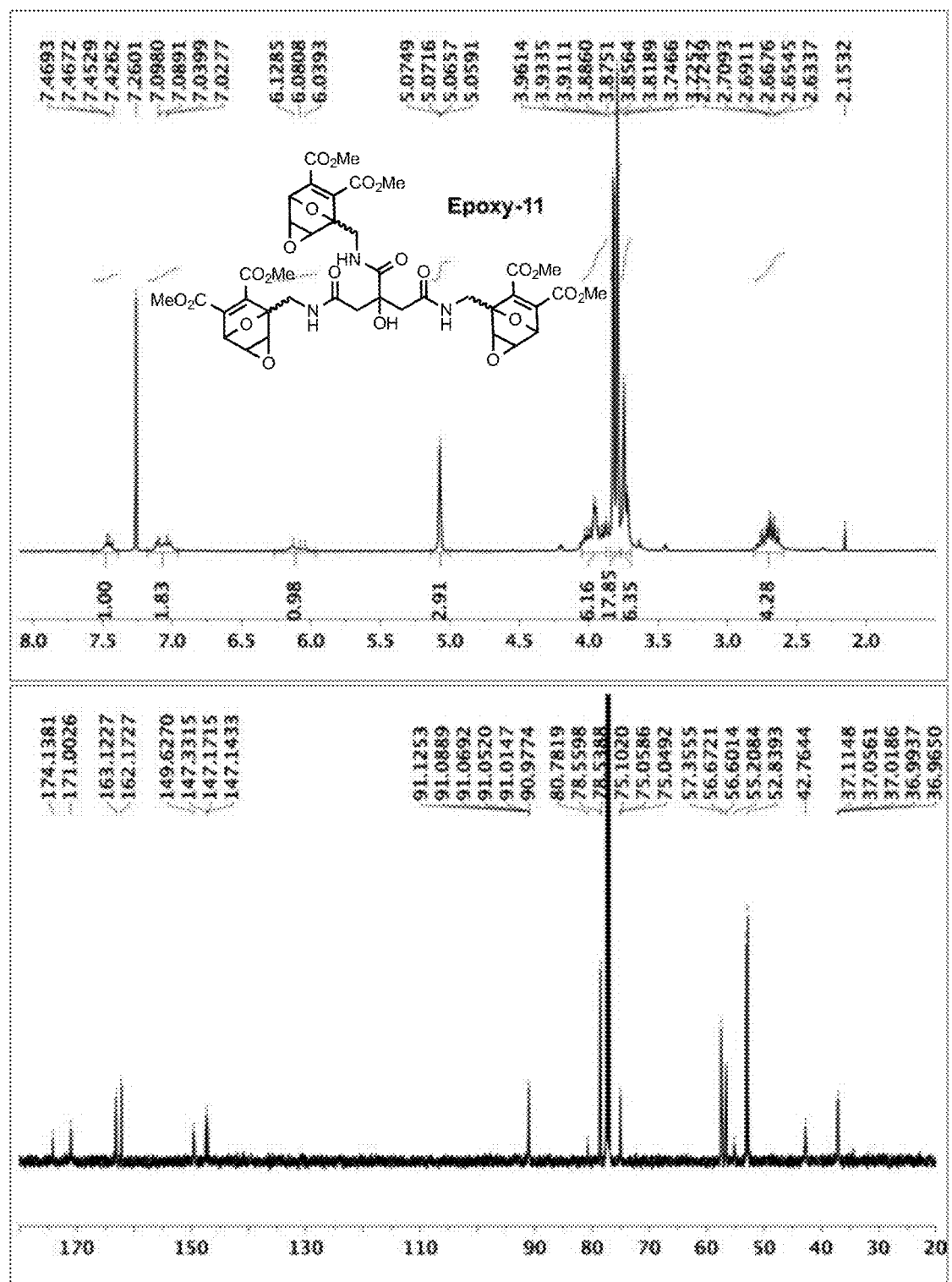
FIG. 40 depicts $^1$H NMR spectra of Epoxy-11.

Bovine serum albumin with ~0.4 thiols per protein present during entrainment/gelation produced hydrogels that released a fraction of protein cargo by diffusion, and the remaining fraction was found to be associated with the gel network. For non-degradable gels derived from bis-OND 8, approximately 20% of the input BSA did not diffuse from the hydrogel (FIG. 21A). Similarly, roughly 20% of BSA in gels derived from linker 7b was found be released with a slow rate similar to that observed in experiments with erosion-probe labeled macromers. This behavior may be useful in tuning the release rate of substrates that would otherwise diffuse freely from the network, as is observed in the case of BSA that is capped with N-ethylmaleimide before entrainment.

What is claimed is:

1. A degradable material comprising:
the reaction product of
an oxanorbornadiene crosslinker or derivative thereof; and
a multivalent nucleophile-terminated compound;

wherein the reaction product is a degradable elastic solid capable of entraining cargo.

2. The degradable material of claim 1,
wherein the oxanorbornadiene crosslinker or derivative thereof is multivalent, and
wherein the multivalent nucleophile-terminated compound comprises a multivalent nucleophile-terminated monomer.

3. The degradable material of claim 1, wherein the multivalent nucleophile-terminated compound comprises a thiol-terminated multivalent polyethylene glycol.

4. The degradable material of claim 1, wherein the multivalent nucleophile-terminated compound has a valency of 4, 5, 6, or 8.

5. The degradable material of claim 1, wherein the multivalent nucleophile-terminated compound comprises endgroups labeled with a probe or cargo.

6. The degradable material of claim 1, further comprising a macromer comprising endgroups labeled with a probe or cargo.

7. The degradable material of claim 1, further comprising an additive, wherein the additive comprises a buffer, catalytic base, or combination thereof.

8. The degradable material of claim 1, wherein the multivalent nucleophile-terminated compound is present in a concentration of 2.5 wt % to 80 wt % of a solution including the multivalent nucleophile-terminated compound, wherein the solution becomes a gel.

9. The degradable material of claim 1, wherein the reaction product is post-functionalized with a second oxanorbornadiene crosslinker or derivative thereof.

10. The degradable material of claim 1, wherein the degradable material is a hyperbranched crosslinked and polymeric material, an elastic hydrogel, an organogel, or a combination thereof.

11. A method for producing a degradable material, the method comprising:
combining a solution of a multivalent nucleophile-terminated compound and an oxanorbornadiene crosslinker to yield elastic solids capable of entraining cargo,
wherein the reaction between the multivalent nucleophile-terminated compound and oxanorbornadiene trigger programmed fragmentation of adducts, and
wherein the programmed fragmentation of adducts causes the material to degrade.

12. The method of claim 11, wherein the combining takes place at a temperature from 20° C. to 40° C.

13. The method of claim 11, wherein the combining takes place at a pH from 6 to 8.

14. The method of claim 11, wherein the programmed fragmentation of adducts takes place at a half-life of adduct fragmentation of 30 seconds to 4 months.

15. The method of claim 14, wherein the half-life of adduct fragmentation is from 12 hours to 1 month.

16. The method of claim 11, wherein the multivalent nucleophile-terminated compound has a valency of 4, 5, 6, or 8.

* * * * *